United States Patent
Ruggeri et al.

(10) Patent No.: US 9,340,559 B2
(45) Date of Patent: May 17, 2016

(54) PROTEASOME INHIBITOR DELANZOMIB FOR USE IN THE TREATMENT OF LUPUS

(75) Inventors: Bruce A. Ruggeri, West Chester, PA (US); Matthew M. Seavey, Secane, PA (US)

(73) Assignee: Cephalon, Inc., Frazer, PA (US)

( * ) Notice: Subject to any disclaimer, the term of this patent is extended or adjusted under 35 U.S.C. 154(b) by 264 days.

(21) Appl. No.: 14/002,249

(22) PCT Filed: Mar. 2, 2012

(86) PCT No.: PCT/US2012/027440
§ 371 (c)(1),
(2), (4) Date: Aug. 29, 2013

(87) PCT Pub. No.: WO2012/119056
PCT Pub. Date: Sep. 7, 2012

(65) Prior Publication Data
US 2013/0345174 A1    Dec. 26, 2013

Related U.S. Application Data

(60) Provisional application No. 61/448,743, filed on Mar. 3, 2011.

(51) Int. Cl.
*A61K 31/69* (2006.01)
*A61K 45/06* (2006.01)
*C07F 5/02* (2006.01)
*C07F 5/04* (2006.01)

(52) U.S. Cl.
CPC ............... *C07F 5/025* (2013.01); *A61K 31/69* (2013.01); *A61K 45/06* (2013.01); *C07F 5/04* (2013.01)

(58) Field of Classification Search
CPC ............................. A61K 31/69; A61K 45/06
See application file for complete search history.

(56) References Cited

U.S. PATENT DOCUMENTS

2008/0132678 A1    6/2008   Adams et al.

FOREIGN PATENT DOCUMENTS

| DE | 10 2008 019916 A1 | 10/2009 |
| WO | WO 2010/114982 | * 10/2010 |
| WO | WO 2010/138101 A1 | 12/2010 |
| WO | WO 2012/119056 A1 | 9/2012 |

OTHER PUBLICATIONS

Aringer, M. and J. S. Smolen "Tumour Necrosis Factor and Other Proinflammatorycytokines in Systemic Lupus Erythematosus: A Rationale for Therapeutic Intervention." Lupus, May 2004, 13(5), 344-347.

Bertsias, G. and D. T. Boumpas "Update on the Management of Lupus Nephritis: Let the Treatment Fit the Patient." Nat. Clin. Pract. Rheumatol, Sep. 2008, 4(9), 464-72.

Boumpas, D. T., R. Furie, et al. "A Short Course of BG9588 (anti-CD40 ligand antibody) Improves Serologic Activity and Decreases Hematuria in Patients With Proliferative Lupus Glomerulonephritis." *Arthritis Rheumatism,* Mar. 2003, 48(3), 719-727.

Chevrier, S., C. Genton, et al. "CD93 is Required for Maintenance of Antibody Secretion and Persistence of Plasma Cells in the Bone Marrow Niche.", Proc. Natl. Acad. Sci. US A Mar. 2009,106(10), 3895-900.

Chauhan D, Anderson KC. "Mechanisms of Cell Death and Survival in Multiple Myeloma (MM): Therapeutic Implications." Apoptosis, Aug. 2003, 8,337-43.

Chun, et al. "Cytokine IL-6 and IL-10 as Biomarkers in Systemic Lupus Erythematosus." J. Clin. Immunol., Sep. 2007, 27(5), 461-6, Epublication Jun. 21, 2007.

Demo et al., "Antitumor Activity of PR-171, a Novel Irreversible Inhibitor of the Proteasome." Cancer Res., Jul. 2007, 67(13), 6383-6391.

Egner, W. "The Use of Laboratory Tests in the Diagnosis of SLE." J. Clin. Pathol, Jun. 2000, 53(6), 424-32.

Espeli, M., S. Bokers, et al. "Local Renal Autoantibody Production in Lupus Nephritis.",J. Am. Soc. Nephrol., Feb. 2011, 22(2), 296-305, Epublication Nov. 18, 2010.

Fairhurst, A.M., A. E. Wandstrat, et al. "Systemic Lupus Erythematosus: Multiple Immunological Phenotypes in a Complex Genetic Disease.", 2006, Adv. Immunol:, 1-69.

Frohlich, K., Holle, J.U., et al. "Successful Use of Bortezomib in a Patient With Systemic Lupus Erythematosus and Multiple Myeloma." Ann. Rheum. Dis. Dec. 2010, doi:10.1136/ard.2010. 133256 (published online ahead of print article).

Fu, et al. "Association of Elevated Transcript Levels of Interferon-Inducible Chemokines With Disease Activity and Organ Damage in Systemic Lupuserythematosus Patients." 2008, *Arthritis Res Ther.,* 10(5), R112, Epublication Sep. 15, 2008.

Kiss, et al. "Anti-Nuscleosome Antibody, A Reliable Indicator for Lupus Nephritis." Aug. 2009, Autoimmunity, 42(5), 393-398.

(Continued)

*Primary Examiner* — Sreeni Padmanabhan
*Assistant Examiner* — Sahar Javanmard
(74) *Attorney, Agent, or Firm* — Baker & Hostetler LLP

(57) ABSTRACT

The present invention provides a method for treating lupus in a subject, comprising the step of administering to the subject Compound A.

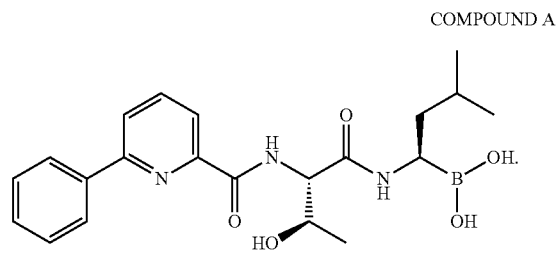

COMPOUND A

10 Claims, 53 Drawing Sheets

(56) References Cited

OTHER PUBLICATIONS

Lee, S.W. and Kim, B.S. "Comparison of Therapeutic Efficacy Between Bortezomib and Combination Treatment of Prednisolone and Mycophenolate Mofetil on Nephritis in NZB/WF1 Mice." May-Jun. 2010, Clin. Exp. Rheumatol., 28(3), 393-396. Epublication Jun. 23, 2010.

Morel, L. "Genetics of SLE: Evidence From Mouse Models." Nat. Rev. Rheumatol, Jun. 2010, 6(6), 348-57, Epublication May 4, 2010.

Morimoto, S., Y. Tokano, et al. "The Increased Interleukin-13 in Patients With Systemic Lupus Erythematosus: Relations to Other Th1-, Th2-related Cytokines and Clinical Findings." 2001, Autoimmunity 34(1),19-25.

Muller, S., J. Dieker, et al. "Pathogenic Anti-nucleosome Antibodies." Lupus, May 2008, 17(5), 431-436.

Neubert, K., S. Meister, et al. "The Proteasome Inhibitor Bortezomib Depletes Plasma Cells and Protects Mice With Lupus-Like Disease From Nephritis." Nat. Med., Jul. 2008, 14(7), 748-755.

Niewold, T. B., J. Hua, et al. "High Serum Ifn-Alpha Activity Is a Heritable Risk Factor for Systemic Lupus Erythematosus." Genes and Immunity, Sep. 2007, 8(6), 492-502.

Piva et al. "CEP-18770: A Novel Orally-Active Proteasome Inhibitor With a Tumor-Selective Pharmacological Profile Competitive With Bortezomib." Blood, Mar. 2008, 111(5), 2765-75.

Sanz, I. and F. E. Lee "B Cells as Therapeutic Targets in SLE." Nat. Rev. Rheumatol, Jun. 2010, 6(6): 326-37.

Seavey et al, "Novel, Orally Active, Proteasome Inhibitor, Delanzomib (DEP-18770), Ameliorates Disease Symptoms and Glomerulonephritis in Two Preclinical Mouse Models of SLE", International Immunopharmacology, Jan. 2012, 12(1), 257-270, Epublication Dec. 13, 2011.

Smith, D. L., and X. Dong, et al. "A Female Preponderance for Chemically Induced Lupus in SJL/J mice." Clin. Immunol., Jan. 2007, 122(1), 101-107.

Smith-Bouvier, and D. L., A. A. Divekar, et al. "A Role for Sex Chromosome Complement in the Female Bias in Autoimmune Disease.", J. Exp. Med., May 2008, 205(5), 1099-108, Epublication Apr. 28, 2008.

Tucci, M., L. Lombardi, et al. "Overexpression of Interleukin-12 and T Helper 1 Predominance in Lupus Nephritis." Clin. Exp. Immunol., Nov. 2008, 1(2), 247-54.

* cited by examiner

Experimental Design: COMPOUND A versus Bortezomib, Treatment of Lupus in the MRL/lpr Mouse Model Body Weight Progression for MRL/lpr Mice across Treatment Groups for the Study Duration Survival for MRL/lpr Mice across Treatment Groups for the Study Duration Lymphomegaly for MRL/lpr Mice across Treatment Groups for the Study Duration Splenomegaly for MRL/lpr Mice across Treatment Groups for the Study Duration Serum IL-12p40/p70 Concentration Over Course of Disease Treatment in MRL/lpr Mice Serum IL-1β Concentration Over Course of Disease Treatment in MRL/lpr Mice Serum TNFα Concentration Over Course of Disease Treatment in MRL/lpr Mice Frequency of Anti-smith Antigen and Anti-dsDNA Antibody Secreting Cells in the Spleens of Treated MRL/lpr Mice Frequency of Anti-Chromatin Antibody Secreting Cells in the Spleens of Treated MRL/lpr Mice Anti-chromatin Anti-nuclear Antibody Concentrations in Treated MRL/lpr Mice Over Time Anti-Smith Antigen Antinuclear Antibody Concentrations in Treated MRL/lpr Mice Over Time Anti-dsDNA Antinuclear Antibody Concentrations in Treated MRL/lpr Mice Over Time Proportion of CD138^hi Spleen Plasma Cells from Treated MRL/lpr Mice Total Urine Protein (Proteinuria) Over Time in Treated MRL/lpr Mice Presence of Urine Leukocytes (Leukoria) in MRL/lpr Mice

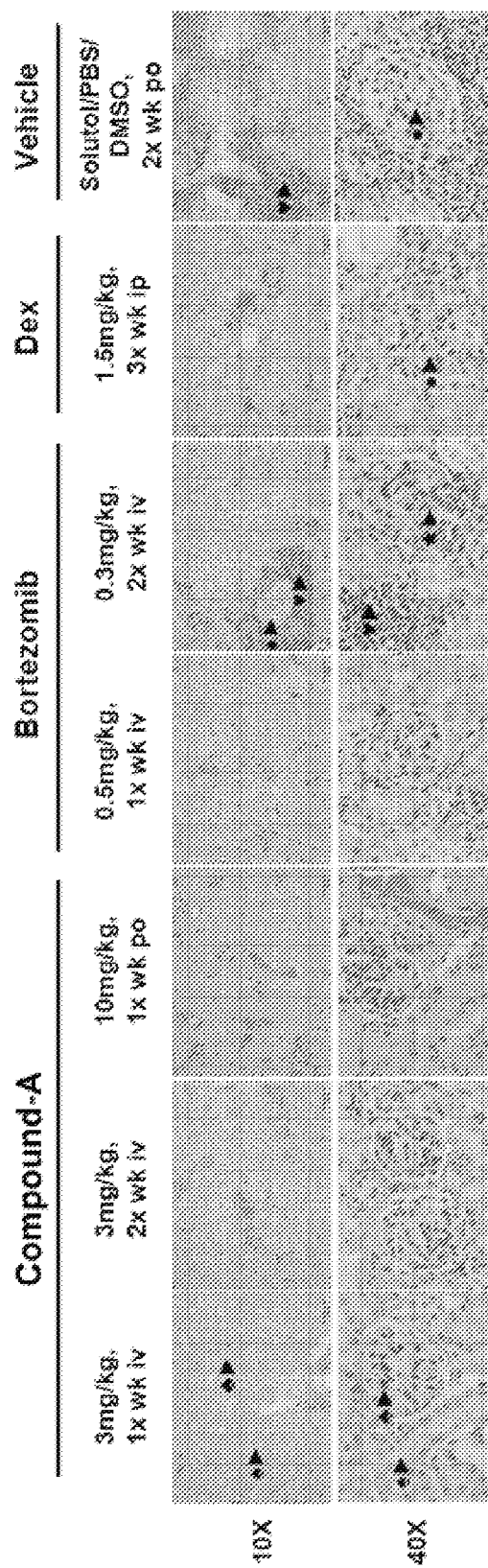

Fig. 17

Renal Histopathology Results from 25 Week Old, Treated MRL/lpr Mice iv=intravenous, po=oral by mouth; ip=intraperitoneal;

♠▲, Normal kidney, no inflammation/pathology; ✱▲, Normal glomerulus and size, no pathology; ◆▲, Vasculitis, ateriosclerosis; ▼▲, Interstitial infiltration, glomerulonephritis; ☐▲, Glomerular hypercellularity, parietal cell hyperplasia/hypertrophy; ✱▲, Glomerular deposits, enlarged glomerulus, membranous nephropathy Activity of the 20S Proteasome in Spleen of MRL/lpr Mice Phospho-IκBα Cellular Accumulation 3 Hours Post Drug Treatment in Kidney of MRL/lpr Mice Experimental Design: COMPOUND A Versus Bortezomib Treatment of Progressive Lupus in the NZM Lupus Nephritis Mouse Model Body Weight Progression for NZM Mice Across Treatment Groups for the Study Duration Splenomegaly for NZM Mice Across Treatment Groups for the Study Duration Total Urine Protein (proteinuria) in Treated NZM Mice Anti-chromatin Antinuclear Antibody Concentrations in Serum of Treated NZM Mice Anti-smith Antigen Antinuclear Antibody Concentrations in Treated NZM Mice Anti-dsDNA Antinuclear Antibody Concentrations in Treated NZM Mice Serum IL-12p40/p70 Concentration Over Course of Disease Treatment in NZM Mice

- Compound-A 3 mg/kg 1x wk ip
- Compound-A 3 mg/kg 2x wk ip
- Bortezomib 0.3 mg/kg 1x wk ip
- Bortezomib 0.3 mg/kg, 2x wk ip
- Cyclophosphamide, 50 mg/kg, 1x wk, ip
- Dexamethasone, 1.5 mg/kg, 3x wk, ip
- Vehicle (Solutol/PBS/DMSO), 1x wk, ip Serum IP-10 Concentration in Treated NZM Mice Serum IL-13 Concentration in Treated NZM Mice Serum TNFα concentration in Treated NZM Mice Serum IL-17A Concentration in Treated NZM Mice Frequency of Anti-chromatin Antibody Secreting Cells in the Spleens of Treated NZM Mice Frequency of Total IgG Antibody Secreting Cells in the Spleens of Treated NZM Mice Serum C3 Complement Levels in Treated NZM Mice Serum Concentration of Collagen Type I Cross-linker in Treated NZM Mice

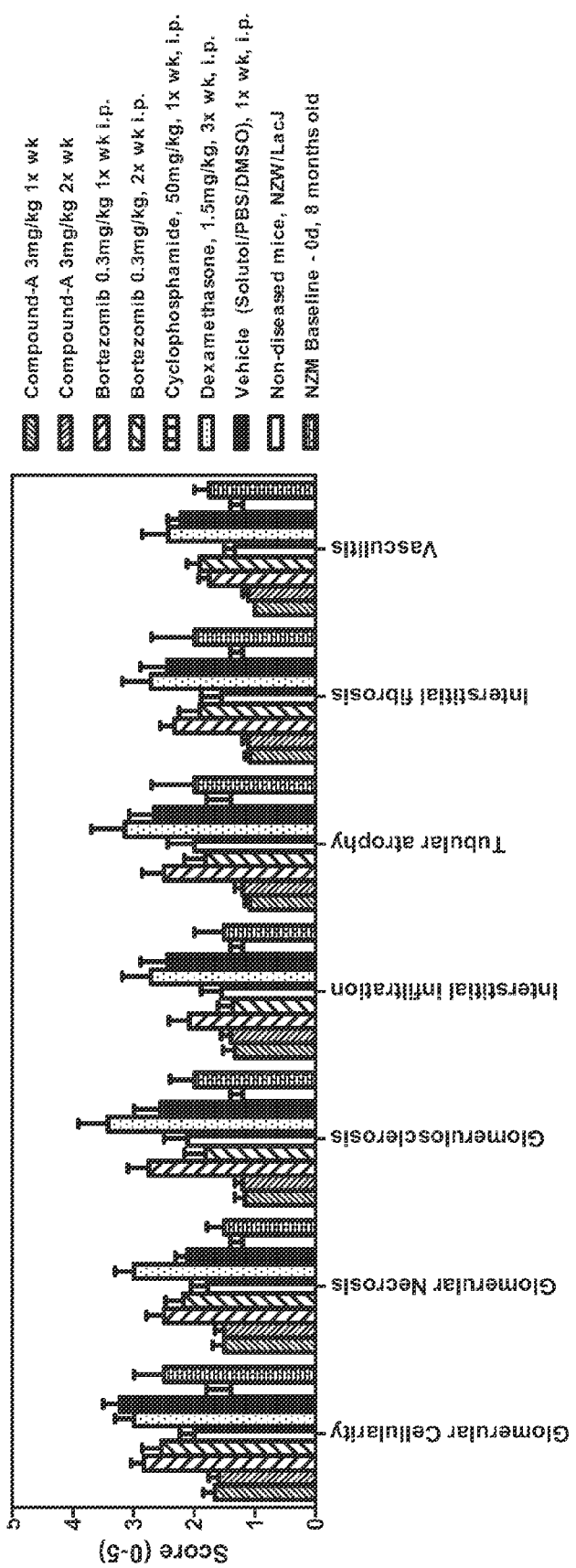

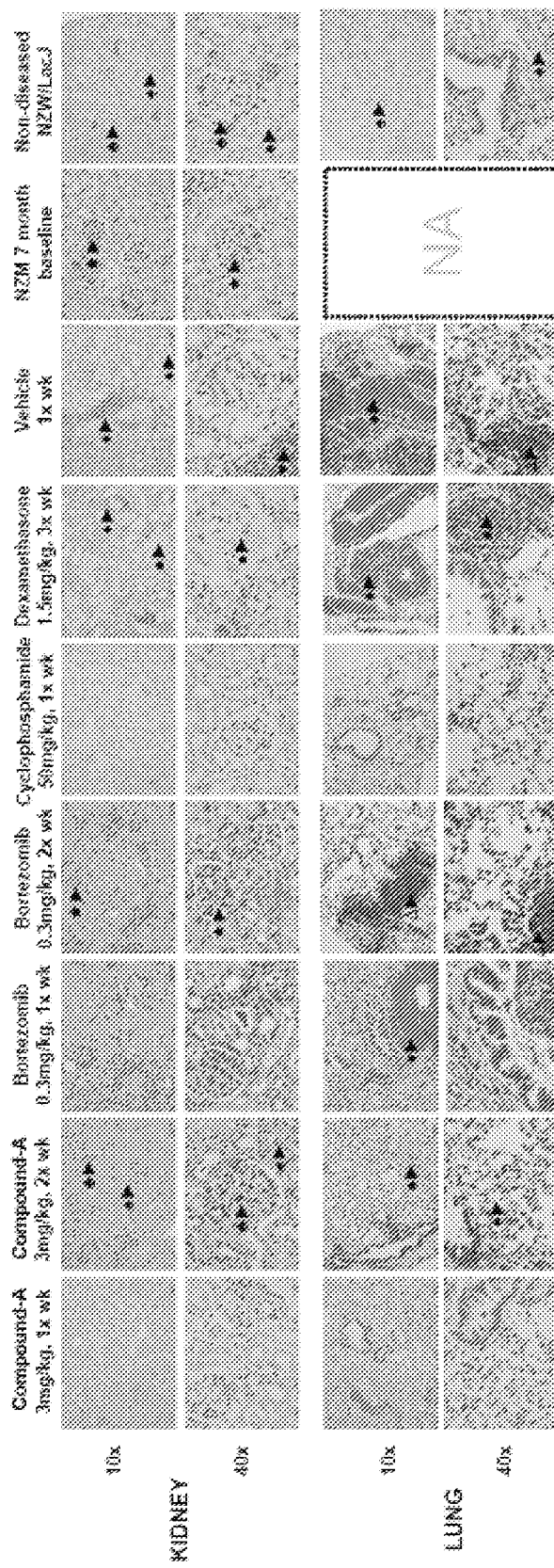

Fig. 39

Renal and Pulmonary Histopathology Results from 40 Week Old, Treated NZM Mice

Kidney:
▲, Normal kidney, no inflammation/pathology; ▲, Normal glomerulus and size, no pathology; ◆▲, Vasculitis, ateriosclerosis; ▼▲, Interstitial infiltration, glomerulonephritis; □ ▲, Glomerular hypercellularity, parietal cell hyperplasia/hypertrophy; ●▲, Glomerular depositis, enlarged glomerulus, membranous nephropathy.

Lung:
▲, Normal lung, no inflammation/pathology; ◆ ▲ Severe pathology - vasculitis, perivascular infiltrations, subpleural lymphocyte infiltrates with Mott cells; △▲, focal solid pulmonary epithelial adenoma.

Inhibition of the 20S Proteasome in Spleens of Treated NZM Mice

Kidney IκBα Accumulation 3 Hours Post Dosing of NZM Mice

Experimental Design: COMPOUND A Versus Bortezomib Treatment
of Progressive Lupus in the NZM Lupus Nephritis Mouse Model Body Weight for NZM Mice at End of Study Day 91

Survival for NZM Mice Across Treatment Groups for the Study Duration

Total Urine Protein (proteinuria) in Treated NZM Mice

Anti-smith Antigen Antinuclear Antibody Concentrations in Treated NZM Mice

Anti-dsDNA Antinuclear Antibody Concentrations in Treated NZM Mice

Levels of Cytokine IL-12 in Treated NZM Mice at Day 91

Frequency of Anti-Smith Antibody Secreting Cells in the Spleens of Treated NZM Mice Frequency of Anti-dsDNA Antibody Secreting Cells in the Spleens of Treated NZM Mice Frequency of Spleen CD38/CD138+ Plasma Cells of Treated NZM Mice Combined Average Renal Histopathology Scores From Treated NZM Mice Spleen and Kidney IκBα Accumulation 3 Hours Post Dosing of NZM Mice

PROTEASOME INHIBITOR DELANZOMIB FOR USE IN THE TREATMENT OF LUPUS

CROSS-REFERENCE TO RELATED APPLICATIONS

This application is the National Stage of International Application No. PCT/US2012/027440, filed Mar. 2, 2012, which claims the benefit of U.S. application Ser. No. 61/448,743, filed Mar. 3, 2011, the disclosures of which are incorporated herein by reference in their entireties.

TECHNICAL FIELD

Lupus therapy.

BACKGROUND

Lupus (systemic lupus erythematosus, SLE) is a chronic autoimmune disease characterized by the presence of activated T and B cells, autoantibodies and chronic inflammation that attacks various parts of the body including the joints, skin, kidneys, CNS, cardiac tissue and blood vessels. In severe cases, antibodies are deposited in the cells (glomeruli) of the kidneys, leading to inflammation and possibly kidney failure, a condition known as lupus nephritis.

Although the cause of lupus remains unknown, manifestations of the disease have been linked to genetic polymorphisms, environmental toxins and pathogens (Morel 2010; Fairhurst, Wandstrat et al. 2006). In addition, gender, hormonal influences and cytokine dysregulation have been tightly linked to the development of lupus (Aringer and Smolen 2004; Smith-Bouvier, Divekar et al. 2008). Lupus affects nine times as many women as men. It may occur at any age, but appears most often in people between the ages of 10 and 50 years. African Americans and Asians are affected more often than people from other races.

There is no cure for lupus. Current treatments for lupus are aimed at controlling symptoms and are limited to toxic and immunosuppressive agents with severe side-effects such as high dose glucocorticoids and/or hydroxchloroquine. Severe disease (e.g., patients that have signs of renal involvement) require more aggressive drugs including mycophenolate mofetil (MMF), azathioprine (AZA) and/or cyclophosphamide (CTX) (Bertsias and Boumpas 2008). CTX, AZA and MMF are very toxic and immunosuppressive, and only 50% of treated patients enter complete remission, with relapse rates up to 30% over a 2-year period.

Proteasome inhibitors have shown some potential as treatments for lupus. In recent studies, bortezomib—the only FDA approved proteasome inhibitor (marketed by Millennium Pharmaceuticals under the trade name Velcade® for multiple myeloma)—markedly prolonged survival of lupus prone NZB/W F1 mice as compared to vehicle, and also significantly reduced proteinuria and improved renal pathology (Neubert, Kirsten et al., 2008; Lee, S. W. and Kim, B. S., 2010). In a more limited study (6 control animals, 5 on drug), bortezomib also significantly improved survival of MRL/lpr mice (p=0.03) (Neubert, Kirsten et al., 2008). In a case study of a woman with both multiple myeloma and lupus, bortezomib combined with prednisolone improved the patient's lupus symptoms (Fröhlich, Karen et al., 2010). An impediment to using bortezomib as a treatment for lupus is that bortezomib is associated with serious side effects such as polyneuropathy, thrombocytopenia and gastrointestinal complications (Lee, S. W. and Kim, B. S., 2010; Fröhlich, Karen et al., 2010).

A need exists for new treatments for lupus, including lupus nephritis.

SUMMARY

Provided are methods for treating lupus in a subject comprising the step of administering to the subject COMPOUND A.

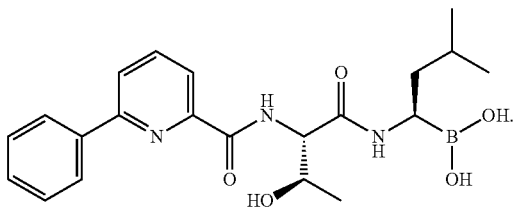

COMPOUND A

In one embodiment, the subject is a human. In one embodiment, the COMPOUND A is administered as a prodrug. In one embodiment, the prodrug is a boronic ester of COMPOUND A. In one embodiment, the prodrug is COMPOUND B

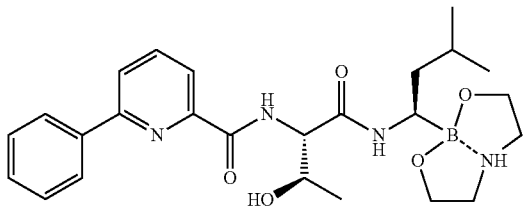

COMPOUND B

In one embodiment, the COMPOUND A is administered once per week. In one embodiment, the COMPOUND A is administered at a dose of about 0.5 mg/m$^2$ to about 5 mg/m$^2$. In one embodiment, the COMPOUND A is administered at a dose of about 1 mg/m$^2$ to about 3 mg/m$^2$. In one embodiment, the COMPOUND A is administered at a dose of about 2 mg/m$^2$.

In one embodiment, the subject experiences a decrease in one or more serum cytokines during treatment. In one embodiment, the subject experiences a decrease in IL-12 during treatment. In one embodiment, the subject experiences a decrease in one or more serum antinuclear antibodies during treatment. In one embodiment, the subject experiences a decrease in serum anti-chromatin IgG during treatment. In one embodiment, the subject experiences a decrease in serum anti-Smith Ag IgG during treatment. In one embodiment, the subject experiences a decrease in serum anti-dsDNA IgG during treatment. In one embodiment, the subject experiences a decrease in proteinuria during treatment. In one embodiment, the subject experiences an increase in serum C3 during treatment.

BRIEF DESCRIPTION OF THE DRAWINGS

FIG. 17 depicts renal histopathology results from MRL/lpr mice (H&E stained paraffin wax embedded kidney tissue sections from 25 week old mice). Images show most severely affected area of tissue sections selected blindly by the pathologist.

FIG. 38 depicts renal histopathology scores from NZM mice.

FIG. 39 depicts renal and pulmonary histopathology results from 40 week old NZM mice (H&E stained paraffin wax embedded kidney tissues sections from 25 week old mice). Images show worst affected area of section selected blindly by the pathologist.

DETAILED DESCRIPTION OF ILLUSTRATIVE EMBODIMENTS

Figure 1:
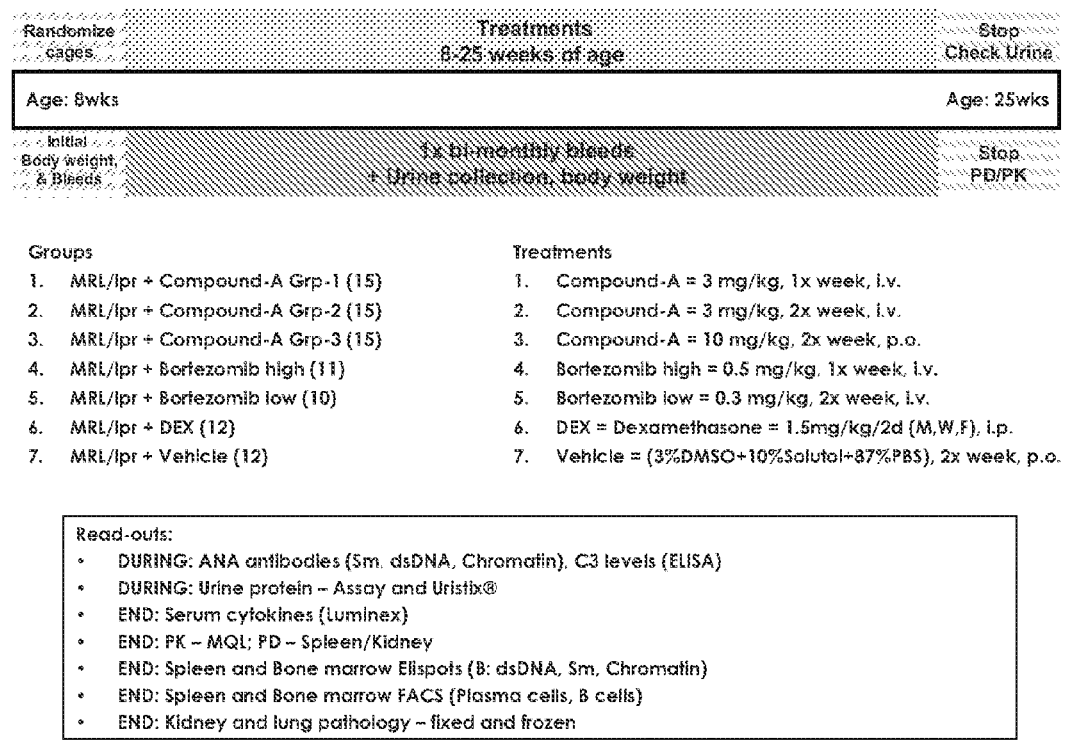
FIG. 1 depicts an overview of the experimental design for testing COMPOUND A and bortezomib in the acute lupus MRL/lpr mouse model.

The term "about" as used herein when referring to a measurable value such as an amount, a temporal duration, and the like, is meant to encompass reasonable variations of the value, such as, for example, ±10% from the specified value. For example, the phrase "about 50%" encompasses reasonable variations of 50%, such as ±10% of the numerical value 50, or from 45% to 55%.

As used herein, the term "subject" includes warm blooded animals, preferably mammals, including humans. In a preferred embodiment, the subject is a primate. In an even more preferred embodiment, the subject is a human.

Provided are methods for treating lupus in a subject by administering to the subject COMPOUND A. COMPOUND A is a proteasome inhibitor with the chemical name [(1R)-1-[[(2S,3R)-3-hydroxy-2-[6-phenyl-pyridine-2-carbonyl) amino]-1-oxobutyl]amino]-3-methylbutylboronic acid (see Bernardini, et al., U.S. Pat. No. 7,576,206). COMPOUND A has the following structure:

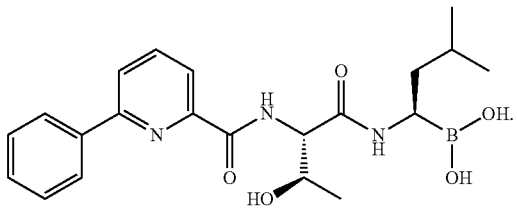

We have found that COMPOUND A is superior to bortezomib in the treatment of lupus. This is surprising because COMPOUND A and bortezomib are both reversible boronic acid proteasome inhibitors that induce cell death through activation of the extrinsic and intrinsic apoptotic signaling pathways (Chauhan D, Anderson K. C. 2003; Piva R, Ruggeri B, et al. 2008). Furthermore, both agents primarily target the proteasome's chymotrypsin-like catalytic activity, with minor inhibition of the caspase-like and little inhibition of the trypsin-like activities (Piva R, Ruggeri B et al. 2008; Demo S D, Kirk C J et al. 2007). Thus, COMPOUND A and bortezomib appear to have similar mechanisms of action. In addition, the compounds have very similar chemical structures. Thus, the mechanism by which COMPOUND A provides enhanced efficacy against lupus as compared to bortezomib is unknown.

The COMPOUND A used in the present invention may be administered in any suitable chemical form, including as a prodrug. Suitable prodrugs include pharmaceutically acceptable ester forms of the parent compound. Preferably, the prodrug converts to the parent compound (I.e., COMPOUND A) after administration. As used herein, "pharmaceutically acceptable ester" refers to a derivative of the parent compound in which the boronic acid residue is modified by making an ester thereof. Preferably, the prodrug is a boronic ester. More preferably, the prodrug is a cyclic boronic ester. Examples of cyclic boronic esters include, but are not limited to, diethanolamine boronic ester, diisopropanolamine boronic ester, aminodiacetic acid boronic ester, pinanediol boronic ester, pinacol boronic ester, 1,2-ethanediol boronic ester, 1,3-propanediol boronic ester, 1,2-propanediol boronic ester, 2,3-butanediol boronic ester, 1,1,2,2-tetramethylethanediol boronic ester, 1,2-diisopropylethanediol boronic ester, 5,6-decanediol boronic ester, 1,2-dicyclohexylethanediol boronic ester, bicyclohexyl-1,1'-diol, and 1,2-diphenyl-1,2-ethanediol boronic ester. Preferably, the prodrug is a diethanolamine boronic ester, diisopropanolamine boronic ester, or aminodiacetic acid boronic ester. More preferably, the prodrug is a diethanolamine boronic ester or diisopropanolamine boronic ester. More preferably, the prodrug is a diethanolamine boronic ester—i.e., COMPOUND B

COMPOUND B

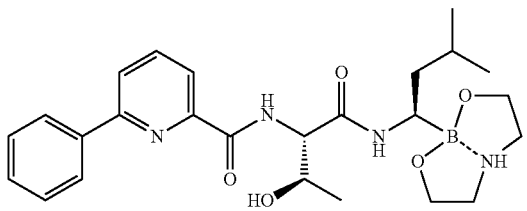

Therefore, in certain embodiments the COMPOUND A is administered as a prodrug. In one embodiment, the COM- POUND A is administered as a boronic ester derivative of COMPOUND A. In one embodiment, the COMPOUND A is administered as a cyclic boronic ester derivative of COMPOUND A. In one embodiment, the COMPOUND A is administered as the cyclic boronic ester COMPOUND B

COMPOUND B

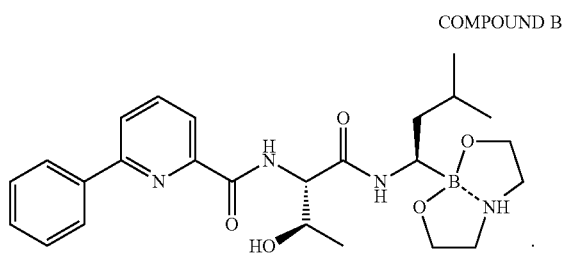

Any suitable method of administration may be used. Examples include injection (subcutaneous, intravenous, parenteral, intraperitoneal, intrathecal, etc.), oral, rectal, transmucosal, inhalation, and transdermal. When administered by injection, the injection can be bolus or continuous infusion. COMPOUND A is preferably administered by intravenous (IV) injection, subcutaneous (SQ) injection, or orally, such as in a tablet or capsule. More preferably, COMPOUND A is administered by intravenous (IV) injection or subcutaneous (SQ) injection. For example, the COMPOUND A may be provided as a sterile lyophilized powder, which may be reconstituted with, e.g., sterile Water for Injection, aqueous saline (NaCl), or aqueous mannitol before injection. Therefore, in one embodiment the COMPOUND A is administered by injection. In another embodiment, the COMPOUND A is administered by IV injection. In another embodiment, the COMPOUND A is administered by SQ injection. In another embodiment, the COMPOUND A is administered orally. In one embodiment, the COMPOUND A is administered orally in a tablet. In another embodiment, the COMPOUND A is administered orally in a capsule.

The COMPOUND A used in the present invention is typically administered to the subject as a pharmaceutical composition. Pharmaceutical compositions of COMPOUND A typically contain, in addition to COMPOUND A and/or a prodrug thereof, at least one pharmaceutically acceptable excipient. Such excipients enable the preparation of solutions, tablets, pills, dragees, powders, capsules, liquids, gels, syrups, slurries, suspensions, emulsions, and the like.

Pharmaceutical preparations for oral use can be obtained by combining COMPOUND A and/or a prodrug thereof with a solid excipient, optionally grinding the resulting mixture, and processing the mixture of granules, after adding suitable auxiliaries, if desired, to obtain tablets or dragee cores. Suitable excipients include fillers or diluents, binders, disintegrants, lubricants, antiadherents, glidants, wetting and surface active agents, colors and pigments, flavoring agents, sweeteners, adsorbents, and taste-maskers.

Diluents are typically added to a small amount of the active drug to increase the size of a tablet. The most common diluent is lactose, which exists in two isomeric forms, alpha-lactose or beta-lactose, and can be either crystalline or amorphous. Various types of lactose include spray dried lactose monohydrate (such as Super-Tab™), alpha-lactose monohydrate (such as Fast Flo®), anhydrous alpha-lactose, anhydrous beta-lactose, and agglomerated lactose. Other diluents include sugars, such as compressible sugar NF, dextrose excipient NF, and dextrates NF. A preferred diluent is lactose monohydrate (such as Fast Flo®). Other preferred diluents include microcrystalline cellulose (such as Avicel® PH, and Ceolus™), and microfine cellulose (such as Elcema®). Diluents may include starch and starch derivatives. Starches include native starches obtained from wheat, corn, rice and potatoes. Other starches include pregelatinized starch NF, and sodium starch glycolate NF. Starches and starch derivatives also function as disintegrants. Other diluents include inorganic salts, such as dibasic calcium phosphate USP (such as Di-Tab® and Emcompress®), tribasic calcium phosphate NF (such as Tri-Tab® and Tri-Cafos®), and calcium sulfate NF (such as Compactrol®). Such polyols as mannitol USP, sorbitol NF, and xylitol NF may also serve as diluents. Many diluents also function as disintegrants and binders, and these additional properties must be taken into account when developing a formulation.

Disintegrants are included in tablet formulations to break the tablets into particles of the active pharmaceutical ingredient and excipients which will facilitate dissolution of the active ingredient and enhance bioavailability of the active ingredient. Starch and starch derivatives, including cross-linked sodium salt of a carboxymethyl ether of starch (such as sodium starch glycolate NF, Explotab®, and Primogel®) are useful disintegrants. A preferred disintegrant is pregelatinized starch, such as Starch 1500®. Another preferred disintegrant is cross-linked sodium carboxymethyl cellulose (such as Croscarmellose Sodium NF, Ac-Di-Sol®). Other disintegrants include cross-linked polyvinylpyrrolidone (such as Crospovidone NF), microcrystalline cellulose (such as Avicel® PH).

Binders are used as wet granulation excipients to agglomerate the active pharmaceutical ingredient and the other excipients. A binder is selected to improve powder flow and to improve compactibility. Binders include cellulose derivatives such as microcrystalline cellulose NF, methylcellulose USP, carboxymethycellulose sodium USP, hydroxypropyl methylcellulose USP, hydroxyethyl cellulose NF, and hydroxypropyl cellulose NF. Other binders include polyvidone, polyvinyl pyrrolidone, gelatin NF, natural gums (such as acacia, tragacanth, guar, and pectin), starch paste, pregelatinized starch NF, sucrose NF, corn syrup, polyethylene glycols, and sodium alginate, ammonium calcium alginate, magnesium aluminum silicate, polyethylene glycols. A preferred binder is polyvinyl pyrrolidone, in particular, Povidone USP, and preferably, povidone K-29/32.

Lubricants are used in tablet formulations to prevent sticking of the tablet to the punch faces and to reduce friction during the compression stages. Lubricants typically include vegetable oils (such as corn oil), mineral oils, polyethylene glycols (such as PEG-4000 and PEG-6000), salts of stearic acid (such as calcium stearate and sodium stearyl fumarate), mineral salts (such as talc), inorganic salts (such as sodium chloride), organic salts (such as sodium benzoate, sodium acetate, and sodium oleate) and polyvinyl alcohols. A preferred lubricant is magnesium stearate.

Dragee cores may be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the COMPOUND A and/or a prodrug thereof in admixture with filler such as lactose, binders such as starches, and/or lubricants such as talc or magnesium stearate and, optionally, stabilizers. In soft capsules, the COMPOUND A and/or a prodrug thereof may be dissolved or suspended in suitable liquids, such as fatty oils, liquid paraffin, or liquid polyethylene glycols. In addition, stabilizers may be added. All formulations for oral administration should be in dosages suitable for such administration.

The COMPOUND A and/or a prodrug thereof may be formulated for parenteral administration by injection, e.g., by bolus injection or continuous infusion. Formulations for injection may be presented in unit dosage form, e.g., in ampoules or in multi-dose containers, optionally with an added preservative. The compositions may take such forms as suspensions, solutions or emulsions in oily or aqueous vehicles, and may contain excipients such as suspending, stabilizing and/or dispersing agents.

Pharmaceutical formulations for parenteral administration include aqueous solutions of the COMPOUND A and/or prodrug thereof in water-soluble form. Additionally, suspensions of the COMPOUND A and/or prodrug thereof may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the COMPOUND A to allow for the preparation of highly concentrated solutions.

The COMPOUND A and/or prodrug thereof may be in powder form for constitution with a suitable vehicle, e.g., sterile Water for Injection, before use. For example, the pharmaceutical composition may be a lyophilized powder. Preferably, the lyophilized powder is reconstituted, for example using 0.9% NaCl, and administered by injection. Lyophilized powders suitable for use in the present invention are disclosed in WO 2010/114982.

Excipients for lyophilized powders include bulking agents that have "generally regarded as safe" (GRAS) status from the United States Food and Drug Administration (FDA). Such bulking agents are well known in the art of pharmaceutical lyophilization, tend to strengthen the structure of the resulting lyophilized cake, and may be used in the present invention. Preferred bulking agents include saccharides, preferably monosaccharides or oligosaccharides, amino acids, sugar alcohols, and mixtures thereof. More preferred bulking agents include saccharides, preferably monosaccharides or oligosaccharides, sugar alcohols, and mixtures thereof. More preferably, bulking agents used in the present invention include sucrose, dextrose, maltose, lactose, sorbitol, glycine, and dextran. A most preferred bulking agent is mannitol.

Cyclodextrins may also be used in lyophilized powder pharmaceutical compositions. Preferred cyclodextrins include the naturally occurring cyclodextrins, methyl-β-cyclodextrin, dimethyl-β-cyclodextrin, trimethyl-β-cyclodextrin, 2-hydroxymethyl-β-cyclodextrin, hydroxyethyl-β-cyclodextrin, 2-hydroxypropyl-β-cyclodextrin, 3-hydroxypropyl-β-cyclodextrin, β-cyclodextrin sulfate, β-cyclodextrin sulfonate, or β-cyclodextrin sulfobutyl ether. Most of these are commercially available from such suppliers as Aldrich Chemical Company, Milwaukee Wis. and Wacker Chemicals, New Canaan, Conn. Preferred cyclodextrins include β-cyclodextrin, hydroxypropyl-β-cyclodextrin and β-cyclodextrin sulfobutyl ether. Preferably, the cyclodextrin is hydroxypropyl β cyclodextrin, hydroxypropyl γ cyclodextrin, sulfobutyl ether β-cyclodextrin, or a mixture thereof. Preferred cyclodextrins include hydroxypropyl-β-cyclodextrin and β-cyclodextrin sulfobutyl ether. In one embodiment, the cyclodextrin is β-cyclodextrin sulfobutyl ether. In another embodiment, the cyclodextrin is hydroxypropyl-β-cyclodextrin. A particularly preferred cyclodextrin is KLEPTOSE® HPB, available from Roquette Frères, France.

The pharmaceutical composition preferably contains from 1% to 95% (w/w) of the active compound (I.e., compound of the present invention). More preferably, the pharmaceutical composition contains from 5% to 70% (w/w) of the active compound.

Preferably, the pharmaceutical composition contains at least one unit dose of the active compound. In general, the unit dose of COMPOUND A and/or prodrug thereof is from about 0.1 mg/m$^2$ to about 10 mg/m$^2$ for a typical subject. More preferably, the unit dose of COMPOUND A and/or prodrug thereof is from about 0.5 mg/m$^2$ to about 5 mg/m$^2$. More preferably, the unit dose is from about 1 mg/m$^2$ to about 5 mg/m$^2$. More preferably, the unit dose is from about 2 mg/m$^2$ to about 4 mg/m$^2$. More preferably, the unit dose is from about 1 mg/m$^2$ to about 3 mg/m$^2$. More preferably, the unit dose is from about 2 mg/m$^2$ to about 3 mg/m$^2$. More preferably, the unit dose is from about 2 mg/m$^2$ to about 2.5 mg/m$^2$. More preferably, the unit dose is about 2 mg/m$^2$.

The COMPOUND A is administered in an amount effective to treat lupus, i.e., an amount effective to prevent, alleviate, or ameliorate symptoms of the disease, prolong survival of the subject being treated, and/or favorably impact lupus-related biomarkers in the subject. Determination of the effective amount of COMPOUND A is well within the capability of those skilled in the art in light of the detailed disclosure and examples provided herein. The effective amount can vary depending on such factors as the size of the subject, the severity of the lupus disease, the frequency of administration, the bioavailability of the compound, the health and co-morbid conditions of the subject, and the quantity and nature of any concurrent treatment (e.g., glucocorticoids). For example, the effective amount of COMPOUND A for monotherapy may be a higher dose than the amount of COMPOUND A that is effective when COMPOUND A is used together in combination with other lupus therapies. Effective doses can be extrapolated from dose-response curves derived from in vitro or animal model test systems, and may be based on the surface area or weight of the subject.

Treatment can be initiated with smaller dosages which are less than the optimum dose of the compound. Thereafter, the dosage can be increased by small increments until the optimum effect under the circumstances is reached. The total daily dosage may be divided and administered in portions during the day if desired. To optimize the dosing regimen, the effectiveness of COMPOUND A can be monitored by monitoring the effect of treatment on various biomarkers in a subject undergoing treatment. Useful biomarkers include those listed in the Examples section herein (e.g., antinuclear antibodies, cytokines such as IL-12, proteinuria, serum complement, etc.). Two especially convenient biomarkers for monitoring the effectiveness of lupus treatment are proteinuria and antinuclear antibodies. An effective dose of COMPOUND A preferably alters the biomarker(s) in the desired way as compared to the biomarker level prior to treatment (e.g., decrease proteinuria, decrease antinuclear antibodies, increase serum C3, etc.). Thus, an effective dose of COMPOUND A can be optimized by starting at a low dose, and then titrating up whilst monitoring one or more of these biomarkers. In general, it is preferable to obtain the initial assessment of the biomarker(s) (e.g., proteinuria or antinuclear antibodies) from the patient prior to beginning therapy and one or more additional assessments at different time points during treatment. In such a use, a baseline determination prior to therapy is determined and then changes in biomarker(s) (e.g., proteinuria or antinuclear antibodies) are determined during the course of therapy and the dose adjusted as needed. Alternatively, two or more successive determinations can be made during treatment without the need of a pre-treatment baseline measurement. In such a use, the first assessment of biomarker(s) (e.g., proteinuria or antinuclear antibodies) should be made from the subject as a baseline level for determining whether the level is increasing or decreasing and the dose adjusted or maintained accordingly.

In preferred embodiments, the subject undergoing treatment with COMPOUND A experiences a desirable change in one or more biomarkers associated with lupus disease. Suitable biomarkers associated with lupus include lymphomegaly, splenomegaly, serum IL-12, serum C3, serum antinuclear antibodies, anti-chromatin IgG, anti-Smith Ag IgG, serum anti-dsDNA antinuclear antibodies, serum IFNα, proteinuria, serum IL-17A, serum IL-6, serum CCL3/MIP-1α, serum CXCL10/IP-10, serum CXCL9/MIG, serum IL-4, serum IL-13, serum IL-1β, serum TNFα, serum KC/IL-8, and serum CTx. Therefore, in one embodiment the subject experiences a decrease in lymphomegaly during treatment with COMPOUND A. In another embodiment, the subject experiences a decrease in splenomegaly during treatment with COMPOUND A. In another embodiment, the subject experiences a decrease in serum IL-12 during treatment with COMPOUND A. In another embodiment, the subject experiences an increase in serum C3 during treatment with COMPOUND A. In another embodiment, the subject experiences a decrease in serum antinuclear antibodies during treatment with COMPOUND A. In another embodiment, the subject experiences a decrease in anti-chromatin IgG during treatment with COMPOUND A. In another embodiment, the subject experiences a decrease in anti-Smith Ag IgG during treatment with COMPOUND A. In another embodiment, the subject experiences a decrease in serum anti-dsDNA antinuclear antibodies during treatment with COMPOUND A. In another embodiment, the subject experiences a decrease in serum IFNα during treatment with COMPOUND A. In another embodiment, the subject experiences a decrease in proteinuria during treatment with COMPOUND A. In another embodiment, the subject experiences a decrease in serum IL-17A during treatment with COMPOUND A. In another embodiment, the subject experiences a decrease in serum IL-6 during treatment with COMPOUND A. In another embodiment, the subject experiences a decrease in serum CCL3/MIP-1α during treatment with COMPOUND A. In another embodiment, the subject experiences a decrease in serum CXCL10/IP-10 during treatment with COMPOUND A. In another embodiment, the subject experiences a decrease in serum CXCL9/MIG during treatment with COMPOUND A. In another embodiment, the subject experiences a decrease in serum IL-4 during treatment with COMPOUND A. In another embodiment, the subject experiences a decrease in serum IL-13 during treatment with COMPOUND A. In another embodiment, the subject experiences a decrease in serum IL-1β during treatment with COMPOUND A. In another embodiment, the subject experiences a decrease in serum TNFα during treatment with COMPOUND A. In another embodiment, the subject experiences a decrease in serum KC/IL-8 during treatment with COMPOUND A. In another embodiment, the subject experiences a decrease in serum CTx during treatment with COMPOUND A.

The COMPOUND A may be administered to the subject at any suitable dose. In one embodiment, the COMPOUND A dose is in the range of about 0.1 mg/m$^2$ to about 10 mg/m$^2$. In another embodiment, the COMPOUND A dose is about 0.5 mg/m$^2$ to about 5 mg/m$^2$. In another embodiment, the COMPOUND A dose is about 1 mg/m$^2$ to about 5 mg/mg$^2$. In another embodiment, the COMPOUND A dose is about 0.5 mg/m$^2$ to about 3 mg/m$^2$. In another embodiment, the COMPOUND A dose is about 1 mg/m$^2$ to about 4 mg/mg$^2$. In another embodiment, the COMPOUND A dose is about 2 mg/m$^2$ to about 4 mg/m$^2$. In another embodiment, the COMPOUND A dose is about 1 mg/m$^2$ to about 3 mg/mg$^2$. In another embodiment, the COMPOUND A dose is about 1.5 mg/m$^2$ to about 3 mg/m$^2$. In another embodiment, the COMPOUND A dose is about 2 mg/m$^2$ to about 3 mg/m$^2$. In another embodiment, the COMPOUND A dose is about 2 mg/m$^2$ to about 2.5 mg/m$^2$. In another embodiment, the COMPOUND A dose is about 2 mg/m$^2$. Preferred COMPOUND A doses include, but are not limited to, 1.1 mg/m$^2$, 1.5 mg/m$^2$, 1.8 mg/m$^2$, 2.1 mg/m$^2$, 2.4 mg/m$^2$, 2.7 mg/m$^2$, and 3.0 mg/m$^2$. More preferably, the COMPOUND A dose is 1.8 mg/m$^2$, 2.1 mg/m$^2$, 2.4 mg/m$^2$, or 2.7 mg/m$^2$. More preferably, the COMPOUND A dose is 2.1 mg/m$^2$ or 2.4 mg/m$^2$. The preceding doses are suitable for any method of COMPOUND A administration, and are especially suitable for subcutaneous or intravenous dosing. Oral doses of COMPOUND A will typically be at the high end of the preceding ranges, such as about 1 mg/m$^2$ to about 7 mg/m$^2$. In one embodiment, the oral dose of COMPOUND A is about 2 mg/m$^2$ to about 6 mg/m$^2$, such as about 3 mg/m$^2$ to about 5 mg/m$^2$. Exemplary oral COMPOUND A doses include, but are not limited to, 2 mg/m$^2$, 3 mg/m$^2$, 4 mg/m$^2$, 5 mg/m$^2$ and 6 mg/m$^2$.

The regimen of administration of each COMPOUND A dose can vary depending on such factors as the pharmacokinetics of the dosage form, the type of lupus symptoms being treated or inhibited, the size of the subject, and the severity of the lupus disease.

The timing of administration of the COMPOUND A can be readily varied by the treating physician to optimize efficacy and minimize side effects in light of the above considerations and the present detailed disclosure. There is wide flexibility in the dosing schedules for COMPOUND A according to present invention.

The COMPOUND A may be administered at the above-described doses according to any suitable schedule. The COMPOUND A dose amounts may be constant or varied within the dosing schedule. Preferably, the COMPOUND A dose is maintained at a constant level during the schedule unless significant drug-related toxicity is observed, in which case subsequent doses can be reduced, for example by about 20-30%. A suitable COMPOUND A schedule will typically range from once-daily dosing to once-weekly dosing or even once-monthly dosing. Preferably, the COMPOUND A is administered less frequently than once-daily, such as one dose every 2-14 days. Preferably, the COMPOUND A is administered every 3 to 28 days, such as every 3 to 14 days. For example, the COMPOUND A may be administered twice per week. In another example, COMPOUND A may be administered once per week. In another example, COMPOUND A may be administered once every two weeks. The schedule may include, after treatment with COMPOUND A for one or more weeks, such as 2, 3, or 4 weeks, a period of at least 5 days during which COMPOUND A is not administered, such as a period of about 7 to 21 days. In one embodiment, the rest period is about 10 to 17 days, such as about 10 days or about 17 days. For example, the COMPOUND A can be administered on days 1, 4, 8 and 11 of a 21 day cycle, wherein days 12-21 are a rest period. In another embodiment, the COMPOUND A can be administered on days 1, 4, 8, and 11 of a 28 day cycle, wherein days 12-28 are a rest period. In another embodiment, the COMPOUND A can be administered on days 1, 8 and 15 of a 28 day cycle, wherein days 16-28 are a rest period. In another embodiment, the COMPOUND A can be administered on days 1 and 8 of a 21 day cycle, wherein days 12-21 are a rest period. In another embodiment, the COMPOUND A can be administered on days 1 and 8 of a 28 day cycle, wherein days 12-28 are a rest period. In another embodiment, the COMPOUND A can be administered on days 1 and 15 of a 21 day cycle. In another embodiment, the COMPOUND A can be administered on days 1 and 15 of a 28 day cycle. The scheduled dosing cycles can be repeated one or more times. For example, the scheduled cycle may be repeated until maximum response is observed, plus one or two additional cycles. As another example, the scheduled cycle may be repeated for 6 to 12 cycles. Optionally, after the initial cycles are completed, a "maintenance schedule" may be used in which the COMPOUND A is administered less frequently and/or at a lower dose than in the initial schedule, such as once per week, once every two weeks, once every three weeks, or once every four weeks. The maintenance schedule may be continued either for a fixed period of time, generally 1-2 years, or indefinitely as long as the patient is continuing to show no signs of progressive disease and is tolerating the treatment without significant toxicity. In certain embodiments, the dosing schedules can be adapted from COMPOUND A dosing schedules suitable for the treatment of other diseases, such as multiple myeloma. For example, COMPOUND A is currently being investigated for the treatment of multiple myeloma by administering COMPOUND A (about 2 mg/m$^2$) on days 1, 8, and 15 of a repeating 28 day cycle.

One or more additional lupus treatments can be used in combination with the administration of the COMPOUND A. Such treatments include, but are not limited to, glucocorticoids, hydroxchloroquine, mycophenolate mofetil (MMF), azathioprine (AZA), and cyclophosphamide (CTX). Appropriate doses of these agents are well known in the art.

Materials and Methods

Compounds

COMPOUND A may be obtained as a solid off-white powder by a procedure analogous to that reported herein. Bortezomib may be obtained by a procedure analogous to that reported herein. Dexamethasone (DEX, 10 mg/mL, liquid, Lot #089016) may be purchased from Hanna's Pharmaceuticals (Wilmington, Del.). Cyclophosphamide (CTX; Hanna's Pharmaceuticals, Wilmington, Del.) is used at 50 mg/kg, once weekly injection, ip. Vehicle used for the suspension of COMPOUND A and bortezomib is 87% PBS, 3% DMSO, 10% Solutol (Mutchler Inc., Solutol HS 15).

COMPOUND A and bortezomib are stored in 75 µL of DMSO at −80° C. in single use aliquots. These aliquots are diluted to final concentrations via the addition of 87% PBS plus 10% Solutol to equal a final concentration of 3% DMSO per formulation.

SYNTHESES

Preparation 1

(1R)-1-[(3aS,4S,6S,7aR)-Hexahydro-3a,5,5-trimethyl-4,6-methano-1,3,2-benzodioxaborol-2-yl]-3-methylbutylamine hydrochloride salt A 20 liter Chemglass® jacketed reactor equipped with overhead stirring, nitrogen sweep, thermocouple with temperature readout, a 1 liter addition funnel, sub-surface gas dispersion tube and auxiliary heater/chiller is charged with 8.0 liters of anhydrous methyl tert-butyl ether. The chiller is set to −40° C. The solvent is cooled to −31.3° C. with agitation. Next, 714.4 g (19.71 mol, 5.0 eq) of HCl(g) is added subsurface over 1.75 hours while maintaining the temperature between −25.7 and −10.0° C. Next, 1.6235 kg (3.964 mol) of N,N-Bis(trimethylsilyl)-(1R)-1-[(3 aS,4S,6S,7aR)-hexahydro-3a,5,5-trimethyl-4,6-methano-1,3,2-benzodioxaborol-2-yl]-3-methylbutylamine (obtained by a method similar to that disclosed in U.S. Patent Publication No. 2005/0240047 (Pickersgill et al.), is dissolved in 2.1 liters of methyl tert-butyl ether. Next, the solution is added to the HCl solution over 40 minutes while maintaining the reaction temperature between −25 and −10° C. After addition is complete the reaction is warmed to ambient temperature and the chiller is turned off. The reaction is allowed to warm to ambient temperature and is stirred overnight. Next, the reaction is concentrated on the rotary evaporator to a volume of 1-2 liters. 3 liters of heptanes are added to the mixture and the distillation continued to remove 3 more liters of distillate. Next, 6 more liters of heptanes are added portion wise while removing 1 more liter of distillate. The product mixture is transferred to the 20 liter Chemglass® jacketed reactor equipped as previously described and allowed to slowly stir overnight at ambient temperature. The next morning the mixture is cooled to about −15° C. to −10° C. and allowed to agitate for 1 hour. The product is filtered through a medium glass sintered filter funnel equipped with a #1 Whatman® filter paper. The product cake is washed with 2 liters of cold (0° C.) heptane and dried in an oven under vacuum (29 mmHg) at 35° C. and purged with nitrogen. The yield is 996.0 g (84%) with a purity of 93.9 A %, and a diastereomer ratio of 98.75:1.25 (d.e.=97.5%).

Preparation 2

6-(2S,3R)—N-[(1R)-1-(1,3,6,2-Dioxazaborocan-2-yl)-3-methylbutyl}-3-hydroxy-2-{(6-phenylpyridin-2-yl)formamido]butanamide (i.e., COMPOUND B)

Step A. Preparation of 6-Phenyl-pyridine-2-carbonyl chloride. A 2-L three neck round bottomed flask equipped with an overhead stirrer, thermocouple, heating mantle with digital temperature controller, condenser and nitrogen inlet/outlet is charged with 100.0 g (0.502 mol) of 6-phenyl-2-pyridinecarboxylic acid and 1500 mL of toluene (Kf<0.02 wt %) then warmed to 40° C. Thionyl chloride (110 mL; 1.51 mol, 3 eq) is then added to the thin slurry via addition funnel over 20 minutes. The thin slurry is heated to 75° C. and stirred overnight (about 10-16 hr), until it becomes a clear solution. After cooling the reaction mixture to room temperature the solvent and excess thionyl chloride are removed in vacuo as follows: Reaction mixture is stripped under full vacuum at 40° C. (bath temperature) to approximately ⅓ its original volume (~500 mL) and then (1000 mL) of fresh toluene is added. Concentration is continued, again stripping to ⅓ original volume (~500 ml) followed by re-dilution with 1000 mL of fresh toluene. The total amount of toluene removed is ~2000 mL.

Step B. Preparation of (2S,3R)-3-Hydroxy-2-[oxo-2-(6-phenyl-pyridin-2-yl)-ethyl}-butyric acid. A 3-L three neck round bottomed flask is equipped with an overhead stirrer, thermocouple, pressure equalizing dropping funnel, nitrogen inlet/outlet and ice/water cooling bath. L-threonine, 62.8 g (0.53 mol) is added, followed by 117 g (1.1 mol) of sodium carbonate and 1500 mL of deionized water. The aqueous solution is cooled to 10.0° C. During this time the addition funnel is charged with the acid chloride/toluene solution prepared in Step A. This toluene solution is added dropwise to the aqueous reaction over approximately 10 minutes at ~10° C. Once the addition is complete, the reaction is warmed to room temperature (~22-25° C.) and vigorously stirred until it is shown to be complete by HPLC analysis (typically ~3 hr). The reaction mixture is then transferred to a separatory funnel and the two layers are separated. The lower aqueous phase is then recharged to the reaction flask. Methanol (800 mL) is then added to the mixture followed by pH adjustment (target pH=1-2) with 2.5M HCl (~850 mL), keeping the temperature at 15-20° C. Some off-gassing typically occurs at ~pH=5, followed by precipitation of the product at pH=3. The slurry is allowed to stir at room temperature for 30 minutes post pH adjustment. The white solid is collected by vacuum filtration, (mother liquor losses <2 mg/mL), washed with deionized water (2×500 ml) then dried in a vacuum oven at 40° C. with a nitrogen sweep to a constant weight to provide 141 g (0.471 mol, 94%) of the title compound with an HPLC purity of 99 A % (95 wt %). $^1$H NMR (d6-DMSO, 400 MHz) δ 12.9 (s, 1H, b), 8.71 (d, 1H, J=9.16 Hz), 8.23 (d, 1H, J=7.24 Hz), 8.1 (m, 3H), 8.03 (d, 1H, J=7.0 Hz), 7.55 (m, 3H), 5.34 (s, 1H, b), 4.46 (dd, 1H, J=2.52, 9.16 Hz), 4.34 (dd, 1H, J=1.92, 6.24 Hz), 1.15 (d, 3H, J=6.4 Hz).

Step C. Preparation of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide. A 10 liter jacketed reaction vessel equipped with a thermocouple, stirring shaft with impeller, addition funnel, and low temperature recirculating bath is charged with 156.1 g (0.52 mol, 1.0 eq) of (2S,3R)-3-hydroxy-2-[oxo-2-(6-phenyl-pyridin-2-yl)-ethyl]-butyric acid, 218.8 g (0.575 mol, 1.1 eq) of O-(7-azabenzotriazol-1-yl)-N,N,N'N'-tetramethyluronium hexafluorophosphate (HATU), 157.7 g (0.522 mol, 1.0 eq) of (1R)-1-[(3aS,4S,6S,7aR)-hexahydro-3a,5,5-trimethyl-4,6-methano-1,3,2-benzodioxaborol-2-yl]-3-methylbutylamine hydrochloride salt (98.8:1.2 mixture of isobutyl diastereomers (R:S)), and 2355 mL of N,N-dimethylformamide (DMF). Agitation is begun to dissolve the solids before cooling the reaction mixture to <–25.0° C. Diisopropylethylamine (218.6 mL, 162.2 g, 1.25 mol, 2.4 eq) is charged to the addition funnel and then added dropwise to the reaction mixture over ~30 minutes at –25° C. to –30° C. Once addition is complete the reaction is stirred at –30° C. for six hours. In a separate twenty-two liter four-neck reaction flask equipped with an overhead stirrer and thermocouple is charged 3925 mL of DI water and 3925 mL of ethyl acetate. The reaction mixture is transferred to this flask over five minutes at RT. The lower aqueous layer is separated and discarded. A solution of 393 g of sodium phosphate monobasic, monohydrate in 3925 mL of DI water is prepared and the organic phase is washed with this solution. The lower aqueous phase is again removed and discarded. A solution of 376.9 g of sodium bicarbonate in 4710 mL of DI water is prepared and the organic phase is washed with this solution after splitting into two portions. Once again the lower aqueous phase is separated and discarded. A saturated sodium chloride solution is prepared using 481.4 g of sodium chloride in 3140 mL of DI water and the organic phase is washed with this solution, the layers are separated and the lower aqueous phase discarded. Norit GAC 1240+ carbon (157 g) is added to the organic phase and the suspension is stirred at RT overnight (13.8 hours). The carbon is removed by vacuum filtration through Whatman GF/C glass fiber filter paper, then washed with 350 mL of ethyl acetate. The filtrate is concentrated to a foam on a rotary evaporator under vacuum with a 33-44° C. bath temperature to provide 231.5 g (0.422 mol, 80.9%) of the title compound as a foam with a chemical purity of 96.4%. The level of threonine isomer is 1.16 A %. %. $^1$H NMR (d6-DMSO, 400 MHz) δ 8.98 (d, b, 1H, J=2.99 Hz), 8.76 (d, 1H, J=8.55 Hz), 8.2 (m, 3H), 8.11 (t, 1H, J=7.71 Hz), 8.02 (d, 1H, J=7.54 Hz), 7.54 (m, 3H), 5.26 (d, 1H, J=4.95 Hz), 4.49 (dd, 1H, J=4.22, 8.52 Hz), 4.13 (m, 2H), 2.6 (m, b, 1H), 2.19 (m, b, 1H), 2.02 (m, b, 1H), 1.83 (t, 1H, J=5.38 Hz), 1.75 (s, b, 1H), 1.68 (m, b, 1H), 1.62 (d, 1H, J=13.9 Hz), 1.36 (d, 1H, J=10.05 Hz), 1.3 (m, b, 3H), 1.22 (d, 6H, J=11.65 Hz), 1.12 (d, 3H, J=6.26 Hz), 0.84 (d, 6H, J=6.57 Hz), 0.79 (s, 3H).

Step D. Preparation of 6-(2S,3R)—N-[(1R)-1-(1,3,6,2-dioxazaborocan-2-yl}-3-methylbutyl}-3-hydroxy-2-{(6-phenylpyridin-2-yl)formamido]butanamide (i.e., COMPOUND B).

Option 1—Two Step Procedure: A twelve liter four neck round bottom flask is equipped with an overhead stirrer, thermocouple and nitrogen outlet before being charged with a solution of 229.8 g (0.42 mol, 1 eq) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide in 2310 mL of methanol. To this is added 3465 mL of n-heptane, 108 g (1.06 mol, 2.5 eq) of (2-methylpropyl)boronic acid and a solution of 70 mL (84 g, 0.85 mol, 2.0 eq) of 37% hydrochloric acid in 353 mL of DI water. Agitation is begun and the two phase mixture is stirred at RT for 16 hours. The reaction mixture is transferred in portions to a four liter reparatory funnel and the lower methanolic phase is separated and returned to the reaction flask. The upper heptane layer is discarded. A fresh charge of 3465 mL of n-heptane is added to the reaction and the reaction is agitated at RT for an additional two hours. Agitation is stopped and the phases are separated and the lower methanolic layer is extracted with n-heptane (2×4600 mL). The heptane phases are discarded and the methanolic phase is concentrated in vacuo with a bath temperature of 40° C. Ethyl acetate (4620 mL) is charged to the evaporation flask and the sticky yellow residue is dissolved before transferring to a twelve-liter reaction flask. A solution of 665.4 g of sodium bicarbonate in 7650 mL of DI water is prepared and used to wash the ethyl acetate layer in two portions (1×4000 mL and 1×3850 mL). A solution of 1059.7 g of sodium chloride in 2700 mL of DI water is prepared and then used to wash the ethyl acetate phase.

After separation of layers the ethyl acetate layer is treated with 47.3 g (0.45 mol, 1.1 eq) of diethanolamine. The mixture is allowed to stir at RT overnight. Precipitated solids are collected by vacuum filtration using a closed filtration flask and the wet cake is washed with 500 mL of ethyl acetate. The sealed filter funnel is transferred to a glove box where it is opened and the 481.8 g of wet cake is transferred to two pyrex drying trays which are then placed into a vacuum oven. The product is dried to a constant weight at 23.5 in of Hg and 50° C. over 27 hours to provide 179.7 g (0.372 mol, 88.8%) of the title compound with a chemical purity of 98.6% and a chiral purity of 98.8% de. $^1$H NMR (d6-DMSO, 400 MHz) δ 8.8 (d, 1H, J=8.52 Hz), 8.2 (m, 3 H), 8.1 (t, 1H, J=7.68 Hz), 8.0 (dd, 1H, J=6.7, 0.9 Hz), 7.5 (m, 3H), 7.2 (d, 1H), 6.5 (t, b, 1H), 5.1 (d, 1H, J=4.92 Hz), 4.5 (dd, 1H), 4.2 (m, 1H), 3.6 (m, 2H), 3.5 (m, 2H), 3.1 (m, 1H), 3.0 (m, 2H), 2.7 (m, 2H), 1.6 (m, 1 H), 1.3 (m, 1H), 1.2 (m, 1H), 1.1 (d, 3H, J=6.32 Hz), 0.8 (2d, 6H, J=6.68, 6.52 Hz).

Option 2—One Step Procedure: A 50 mL three neck round bottom flask is equipped with a thermocouple, stir bar, nitrogen inlet/outlet, heating mantle and temperature controller. The flask is charged with 2.0 g (3.65 mmol, 1.0 eq) of N-[(1S, 2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide and 20 mL of MTBE. The reaction mixture is stirred for approximately 10 minutes until all the solids dissolved. Diethanolamine (0.44 mL, 0.48 g, 4.57 mmol, 1.25 eq) is charged via syringe, along with 2 drops of methanesulfonic acid, to the light yellow solution and the mixture is heated to 50° C. After approximately 30 minutes a white precipitate begins to form. Stirring is continued overnight before cooling to room temperature. The solids are collected by vacuum filtration, washed with MTBE (1×20 mL) then dried under vacuum at 60° C. overnight to give 0.92 g (1.9 mmol, 52%) of the title compound as a white solid with a chemical purity of 91.9% and a chiral purity of >99.5% de.

Step E (optional). Purification of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (COMPOUND B). A two liter four neck round bottom flask is equipped with an overhead stirrer, thermocouple, condenser, heating mantle, temperature controller and nitrogen outlet before being charged with 175 g (0.363 mol) of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide and 1400 mL (8 volumes) of 95% ethanol. Agitation is begun and the resultant suspension is heated to 75.7° C. over 21 minutes. Once at temperature the solution is stirred for 80 minutes at 74.9-75.8° C. before cooling to 2.7° C. over 80 minutes. The reaction slurry is then stirred at 2.2-6.0° C. overnight (17 hours) to fully crystallize the product. Precipitated solids are collected by vacuum filtration using a closed filtration flask and the wet cake is washed with 350 mL of 95% ethanol. The sealed filter funnel is transferred to a glove box where it is opened and the 203.8 g of wet cake is transferred to a pyrex drying tray which is then placed into a vacuum oven. The product is dried to a constant weight at 23.5 in of Hg and 50° C. over 19 hours to provide 147.3 g (0.306, mol, 84.2%) of the title compound with a chemical purity of 99.76% and an optical purity of >99.8% de.

Preparation 3

[(1R)-1-[[(2S,3R)-3-Hydroxy-2-[[(6-phenylpyridin-2-yl)carbonyl]amino]-1-oxobutyl]amino]-3-methylbutyl]boronic acid (i.e., COMPOUND A)

A 50 mL three neck round bottom flask equipped with a thermocouple, stir bar and nitrogen outlet is charged with 1.65 g (3.4 mmol) of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (chemical purity=99.5%, chiral purity >99.5% de), 17 mL of methyl isobutyl ketone and 1.7 mL of 2N hydrochloric acid. The mixture is stirred overnight. The layers of the reaction are separated and the organic layer is dried over magnesium sulfate, filtered and evaporated to dryness in vacuo. The residue is triturated in pentane and the resultant white solid is collected by vacuum filtration before drying in a vacuum oven overnight at 60° C. to give 1.26 g (3.1 mmol, 90%) of the title compound. HPLC indicates a purity of 99.6 A %. Chiral purity >99.5% de. $^1$H NMR (d4-MeOD, 400 MHz) δ 8.17 (m, 2H), 8.13 (m, 1H), 8.05 (m, 2H), 7.5 (m, 3H), 4.75 (d, 1H, J=3.04 Hz), 4.42 (dq, 1H, J=2.92, 6.4), 2.7 (t, b, 1H), 1.61 (m, 1H), 1.35 (t, 2H, J=7.48 Hz), 1.29 (d, 3H, J=6.36 Hz), 0.89 (d, 6H, J=6.52 Hz).

Preparation 4

(2S)—N-[(1R)-1-(1,3,6,2-dioxazaborocan-2-yl)-3-methylbutyl]-3-phenyl-2-(pyrazin-2-ylformamido) propanamide (i.e., diethanolamine ester of bortezomib)

Step A. Preparation of pyrazine-2-carbonyl chloride. A 500 ml three neck round bottomed flask equipped with a stir bar, thermocouple, heating mantle with digital temperature controller, condenser and nitrogen inlet/outlet is charged with 15 g (0.12 mol) of pyrazine carboxylic acid, 225 mL of toluene (Kf<0.02 wt %) and 26.4 ml (43 g, 0.36 mol) of thionyl chloride. The thin slurry is heated to 75° C. and stirred overnight (10-16 hr). After cooling the reaction mixture to room temperature the solvent and excess thionyl chloride are removed in vacuo as follows: Reaction mixture is stripped under full vacuum at 60° C. (bath temperature) to approximately ⅓ its original volume and then (175 ml) of fresh toluene is added. Concentration is continued, again stripping to ⅓ original volume followed by re-dilution with 225 ml of fresh toluene to provide the pyrazine acid chloride in a toluene solution.

Step B. Preparation of (S)-3-phenyl-2[(pyrazine-2-carbonyl)-amino]-propionic acid. A second 500 ml three neck round bottomed flask is equipped with a stir bar, thermocouple, pressure equalizing dropping funnel, nitrogen inlet/outlet and ice/water cooling bath. L-Phenylalanine, 20.2 g (0.122 mol) is added, followed by 28.2 g (0.266 mol) of sodium carbonate and 225 mL of deionized water. The aqueous solution is cooled to 10.0° C. During this time the addition funnel is charged with the acid chloride/toluene solution prepared in Step A (~125 mL). This toluene solution is added dropwise to the aqueous reaction over approximately 10 minutes at ~10° C. Once the addition is complete, the reaction is warmed to room temperature (~22-25° C.) and vigorously stirred for 3 h. The reaction mixture is then transferred to a reparatory funnel and the two layers are separated. The lower aqueous phase is then recharged to the reaction flask. Methanol (125 mL) is then added to the red solution followed by pH adjustment (target pH=1-2) with 3.0 M HCl (~175 mL), keeping the temperature at 15-20° C. Some off-gassing occurs at ~pH=5, followed by precipitation of the product at pH=3. The slurry is allowed to stir at room temperature for 30 minutes at ambient temperature post pH adjustment. The resulting pink solid precipitate is collected by vacuum filtration, (mother liquor losses <2 mg/mL), washed with deionized water (1×50 ml) then dried in a vacuum oven at 40° C. with a nitrogen sweep to a constant weight to provide 11.92 g (0.43.9 mmol, 36%) of the title compound with an HPLC purity of 99 A %. $^1$H NMR (d6-DMSO, 400 MHz) δ 13.04 (s, 1H), 9.14 (d, 1H, J=1.44 Hz), 8.88 (dd, 2H, J=2.48, 6.16 Hz), 8.75 (dd, 1H, J=1.52, 2.4 Hz), 7.25 (m, 4H), 7.18 (m, 1H), 4.75 (dt, 1H, J=5.48, 8.08 Hz), 3.2 (dd, 2H, J=1.79, 5.32 Hz).

Step C. Preparation of N-[(1S)-1[[[(1R)-1-[3aS,4S,6S,7aR)-hexahydro-3a,5,5-trimethyl-4,6-methano-1,3,2-benzodioxaborol-2-yl]-3-methylbutyl]amino]carbonyl]-2-benzyl] 2-pyrazine carboxamide. A 500 ml three neck round bottomed flask equipped with a stir bar, addition funnel, thermocouple, nitrogen inlet/outlet and cooling bath is charged with 11 g (99.9 mmol) of (S)-3-phenyl-2-[(pyrazine-2-carbonyl)-amino]-propionic acid, 15.5.0 g (40.6 mmol) of 0-(7-azabenzotriazol-1-yl)-N,N,N'N'-tetramethyluronium hexafluorophosphate (HATU), 12.2 g (40.6 mmol) of (1R)-1-[(3aS,4S,6S,7aR)-hexahydro-3a,5,5-trimethyl-4,6-methano-1,3,2-benzodioxaborol-2-yl]-3-methylbutylamine hydrochloride salt (87:13 mixture of isobutyl diastereomers (R:S)) and 165 mL of N,N-dimethylformamide (DMF). The pale yellow reaction solution is cooled to −35° C. where 12.6 g (17 mL, 97.3 mmol) of N,N-di-isopropyl ethyl amine is added dropwise over six minutes at −34° C. to −35° C. The resulting solution is then stirred overnight at −40 to −11° C. The reaction mixture is quenched onto 600 ml of a 1:1 cold water/ethyl acetate mixture. After transferring into a reparatory funnel the layers are separated. The organic phase is then washed successively with 10% aqueous sodium hydrogen phosphate (1×200 mL), 8% aqueous sodium bicarbonate (2×200 mL) and saturated sodium chloride (1×200 mL). The product solution is dried over magnesium sulfate then filtered. The filtrate is evaporated to dryness in vacuo to give 19.57 g (37.7 mmol, 93%) of the title compound as a light brown foam with an HPLC purity of 92 A %. $^1$H NMR (d6-DMSO, 400 MHz) δ 9.15 (d, 1H, J=1.44 Hz), 8.87 (d, 1H, J=2.48 Hz), 8.7 (m, 3H), 7.25 (m, 4H), 7.18 (m, 1H), 4.89 (q, 1H, J=6.88, 15.4 Hz), 4.13 (dd, 1H, J=1.8, 8.56 Hz), 3.15 (d, 2H, J=6.88 Hz), 2.7 (m, b, 1H), 2.22 (m, b, 1H), 2.05 (m, b, 1H), 1.87 (t, 1H, J=5.40 Hz), 1.81 (s, b, 1H), 1.67 (d, b, 1H), 1.52 (m, b, 1H), 1.13-1.33 (m, 9H), 0.83 (dd, 6H, J=2.48, 6.56 Hz), 0.80 (s, 3H).

Step D. Preparation of (2S)—N-[(1R)-1-(1,3,6,2-dioxazaborocan-2-yl)-3-methylbutyl]-3-phenyl-2-(pyrazin-2-ylformamido)propanamide (i.e., diethanolamine ester of bortezomib). A one liter four neck round bottomed flask is equipped with an overhead stirrer, thermocouple and nitrogen inlet/outlet then charged with 19.0 g (36.6 mmol) of N-[(1S)-1[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-benzyl]2-pyrazine carboxamide 9.32 g (91.5 mmol) of isobutylboronic acid, 190 mL of methanol, 34.7 mL (69.4 mmol) of 2M aqueous hydrochloric acid and 285 mL of heptane. The two phase reaction is stirred at room temperature overnight until an IPC showed <2% starting material remaining by area. The reaction mixture is transferred to a separatory funnel and the layers are separated. The lower methanol layer is washed with heptanes (2×250 mL) before being removed to a one-liter round bottomed flask and evaporating to dryness in vacuo. The resulting residue is dissolved in 300 mL of ethyl acetate which is washed with 8% aqueous sodium bicarbonate (2×200 mL) and brine (1×300 mL), before transferring to a clean one liter three neck round bottom flask equipped as above.

To the ethyl acetate solution is added 4.1 g (38.4 mmol) of diethanolamine and the mixture is stirred at room temperature for about 10 to 100 hours. The resulting solids are collected by vacuum filtration, washed with ethyl acetate (1×30 mL) then dried in a vacuum oven at 50° C. overnight to provide the title compound as a white solid (15.8 g, 34.9 mmol, 95.2%), which is shown by HPLC to be a 91:9 mixture of diastereomers (i.e., 82% de).

Step E (optional). Purification of (2S)—N-[(1R)-1-(1,3,6,2-dioxazaborocan-2-yl)-3-methylbutyl]-3-phenyl-2-(pyrazin-2-ylformamido)propanamide (i.e., diethanolamine ester of bortezomib). (2S)—N-[(1R)-1-(1,3,6,2-dioxazaborocan-2-yl)-3-methylbutyl]-3-phenyl-2-(pyrazin-2-ylformamido)propanamide is charged to a 250 ml three round bottom flask equipped with a stir bar, thermocouple, heating mantle, controller, condenser and nitrogen inlet/outlet. Ethanol (absolute, 128 mL) is then charged to the flask and heated to reflux. Undissolved solids (which are enriched about (2:8) in the undesired isomer) are removed by vacuum filtration. The filtrate is returned to the round bottom flask and cooled to room temperature to crystallize the product which is isolated by vacuum filtration, washed with cold absolute ethanol (1×50 ml), and dried in a vacuum oven at 50° C. overnight to provide 11.6 g (25.6 mmol, 70%) of the title compound as a 94:6 mixture of diastereomers (i.e., 88% de). The chemical purity is >99.9 A %. $^1$H NMR (d6-DMSO, 400 MHz) δ 9.10 (d, 1H, J=1.4 Hz), 8.88 (d, 1H, J=2.48 Hz), 8.83 (d, 1H, J=8.84 Hz), 8.75 (dd, 1H, J=1.52, 2.32 Hz), 7.3 (m, 5H), 6.55 (s, b, 1H), 4.75 (m, 1H), 3.65 (m, 2H), 3.55 (m, 1H), 3.45 (m, 1H), 2.9-3.2 (m, 4H), 2.8 (m, 1H), 2.7 (m, 2H), 1.56 (m, 1H), 1.33 (dt, 1H, J=4.04, 13.80 Hz), 1.18 (dt, 1H, J=3.48, 9.88 Hz), 0.8 (dd, 6H, J=6.64, 12.56 Hz).

Preparation 5. Bortezomib

A 100 ml three neck round bottom flask is equipped with a stir bar, thermocouple and nitrogen inlet/outlet then charged with 5.0 g (10.4 mmol) of (2S)—N-[(1R)-1-(1,3,6,2-dioxazaborocan-2-yl)-3-methylbutyl]-3-phenyl-2-(pyrazin-2-ylformamido)propanamide (i.e., diethanolamine ester of bortezomib), 50 ml of methanol and 10.4 ml of 2N aqueous hydrochloric acid. The reaction is stirred at room temperature overnight before removing the solvent in vacuo at 40° C. The resulting residue is dissolved in 50 ml of ethyl acetate and washed with saturated sodium bicarbonate (1×50 mL) before once again concentrating the organic layer to dryness in vacuo. The residue is then triturated overnight at room temperature with 50 mL of pentane under nitrogen. The resulting free flowing solids are collected by vacuum filtration, washed with pentane (1×20 ml) then dried in a vacuum oven at 30° C. overnight to provide 3.29 g (8.56 mmol, 82.3%) of the title compound as a white solid with chemical purity >99.8 A % and a 93.5:6.5 ratio of diastereomers (i.e., 87% de). $^1$H NMR (d4-MeOH, 400 MHz) δ 9.15 (d, 1H, J=1.36 Hz), 8.77 (d, 1H, J=2.48 Hz), 8.68 (dd, 1H, J=1.52, 2.44 Hz), 7.27 (m, 4H), 7.21 (m, 1H), 5.05 (t, 1H, J=7.68 Hz), 3.2 (m, 2H), 2.66 (t, 1H, J=7.56 Hz), 1.39 (m, 1H), 1.17 (t, 2H, J=7.12 Hz), 0.83 (dd, 6H, J=5.32, 6.40 Hz).

Preparation 6

6-Phenyl-pyridine-2-carboxylic acid {(1S,2R)-1-[(R)-1-(4,8-dimethyl-[1,3,6,2-dioxaborocan-2-yl)-3-methylbutylcarbamoyl}-2-2-hydroxypropyl}amide (i.e., diisopropanolamine ester of COMPOUND A)

A 50 mL four neck round bottom flask is equipped with a stir bar, thermocouple, heating mantle with temperature controller, condenser and nitrogen inlet then charged with 2.0 g (3.65 mmol) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (chemical purity=95.7%, chiral purity about 97.5% de (based on the fact that the (1R)-1-[(3aS,4S,6S,7aR)-hexahydro-3a,5,5-trimethyl-4,6-methano-1,3,2-benzodioxaborol-2-yl]-3-methylbutylamine used to make the N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide has a 97.5% de)), 30 mL of t-butyl methyl ether (MTBE) and 0.61 g (94.56 mmol, 1.25 eq) of diisopropanolamine. The resultant yellow solution is stirred at 20-25° C. for 16 hours. An additional 1.2 g (9 mmol, 2.5 eq) of diisopropanolamine is charged and the mixture heated at 40° C. for 16 hours before cooling to room temperature. The white solid is collected by vacuum filtration, washed with 15 mL of MTBE then dried under vacuum overnight at 33° C. to yield 1.31 g (2.55 mmol, 70%) of the desired product based on ¹H NMR. The chemical purity is 96.8 A % and no diastereomer is detected by HPLC (>99.8% de).

Acute Systemic Lupus Erythematosus (SLE) Model

Animals

Six week old lupus-prone, female, MRL/lpr (Jackson Labs, #000485) and non-lupus prone control MRL/MpJ (Jackson Labs, #000486) mice are obtained from Jackson Laboratories (Bar Harbor, Me.) at 6-weeks of age. All mice are maintained on a 24 hour light/dark cycle, with food and water available ad libitum. All experimental animal procedures are approved by and in accordance to the regulations of the Institutional Animal Care and Use Committee (IACUC) of Cephalon, Inc; approved IACUC protocol #03-040 and #03-03-041.

MRL/lpr mice develop a rapid lymphoproliferative disease due to an inactive Fas molecule preventing the proper apoptosis of self-reactive T and B cells in primary and secondary lymphoid tissues (deficiency in both central and peripheral tolerance mechanism). Due to this impaired tolerance mechanism, a percentage of all T and B cells that enter the periphery have a high likelihood of responding to self protein/tissues and thus initiate autoimmunity early in life. The MRL/lpr model mice develop several chronic inflammatory disease-like symptoms that are characteristic of early and late lupus including the generation of anti-nuclear antibodies, arthritis, dermatological manifestations, immunocomplex-mediated glomerulonephritis leading to proteinuria and eventual death. Lesser characterized phenomenon are CNS and cardiac manifestations, both of which are more common in humans. Previous optimization and validation studies clearly showed that disease only manifests in diseased MRL/lpr animals and not the control mice, MRL/Mp, and that antinuclear antibodies (ANAs) rapidly form between weeks 4-12 leading to the onset of lupus nephritis around weeks 18-25 with the presence of proteinuria. Mortality is higher in the females and occurs around 25 weeks of age, renal disease includes glomerulonephritis, glomerular infiltrates, sclerosis and vasculitis. Both splenomegaly and lymphomegaly associated with dermatitis can also be observed.

Antinuclear Antibody (ANA) ELISA Assays

The measurement of serum anti-dsDNA and anti-Smith antigen antibodies is done by an in-house generated custom ELISA assay. Chromatin coated plates are purchased from Inova Diagnostics, Inc. Purified bovine thymus dsDNA (Sigma, St. Louis, Mich.) or purified bovine Smith antigen (GenWay, San Diego, Calif.) are used as coating antigen for the detection of anti-dsDNA and anti-Smith Ag antibodies respectively. Coated plates are washed with Borate Sulfate Saline (BSS) and blocked with BSS containing 1% Bovine Serum Albumin (BSA) and 0.1% Tween-20 detergent. Standard curves are generated using mouse anti-chromatin antibody (Sigma, 2B1) or 25 week old MRL/lpr serum. Mouse anti-dsDNA antibody (Abcam, Cambridge, Mass.), or mouse anti-Smith antigen antibody (Abcam) are used as standards for each assay. Secondary antibody is purchased from Abcam (goat anti-mouse pAb-HRP), the substrate is purchased from Rockland (Gilbertsville, Pa.) (TMB), and stop reaction buffer is generated using 1 mL of concentrated sulfuric acid into 20 mL of dH$_2$O. Developed plates are read using a Victor-X4 spectrophotometer reading at 450 nM with a reference wavelength of 570 nM. For all ANA ELISA assays, values below the limit of detection set by the lowest point along the standard or set by the manufacturer are considered out of range and are not estimated, but assumed the lowest point along the standard curve for that particular assay.

Antibody Secreting B-Cell Elispot Assays

B-cell Elispot components are ordered from MabTech (Nacka Strand, Sweden) and nitrocellulose IP filter plates are ordered from Millipore (Billerica, Mass.). Elispot wells are coated with either purified bovine thymus dsDNA (Sigma), purified bovine Smith antigen (GenWay) or boiled filtered purified chicken chromatin from lysed chicken red blood cells (Rockland, Gilbertsville, Pa.) at 10 µg/mL. Spleens are processed using glass homogenization, filtered through a 60 µm sterile cell strainer and red blood cells (RBCs) lysed using BioLegend (San Diego, Calif.) lysis buffer. Processed splenocytes are added to each well in culture medium. To avoid skewing of true ex vivo frequencies of antibody secreting cell types (ASCs), cells are not stimulated with a polyclonal mitogen like LPS, but rather incubated in media alone to allow monitoring of genuine ex vivo antibody release. Anti-mouse pan-IgG is used as a positive control for total IgG producing ASCs and is used to normalize results. Frequencies for each antigen are identified in an initial test phase for each model. For chromatin and total IgG only, 30,000 splenocytes are added to each well; for Smith antigen and dsDNA, 500,000 cells are added to each well. Different numbers of splenocytes are added for different antigens due to saturation limits of spot frequencies per well. These limits are previously established. B-cell Elispots are incubated overnight at 37° C. To develop each assay, secondary antibody is added to each well, incubated, washed and alkaline phosphatase strepavidin is used as the conjugate; substrate used is BCIP-NBT. Plates are developed until spots are visible. All Elispot analyses are performed using an Immunospot C.T.L. scanner and Biospot software (Cellular Technology Ltd., Shaker Heights, Ohio). Results are shown as values from which media and cells only wells are subtracted. Some values are negative due to high background.

Flow Cytometry

Washed, RBC-lysed splenocytes are stained for plasma cell markers as previously used in published reports (Neubert, Meister et al. 2008). As used herein the term "plasma cell" will refer to the following immunophenotype definition: Plasma cells are defined as live CD19-negative, CD138-positive, intracellular kappa light chain-positive events. A total of 200,000-500,000 events are collected per tube/sample. Flow staining protocol is as follows, briefly, cells are suspended in complete medium (defined below) and 2.5 µg of anti-CD16/CD32 (FcBlock) with anti-CD19-FITC and anti-CD138-APC antibodies. After 20 minutes of staining on ice, samples are washed then fixed and permeabilized using a BD intracellular staining kit. Samples are stained with anti-kappa Ig light chain-PE in permeabilization buffer for at least 1 hour, washed twice in permeabilization buffer then finally washed in medium and prepared for flow analysis on ice. All samples are replicated with appropriate, matched isotypes as described below.

BD Trucount Tubes (Beckman Dickson, San Diego, Calif., cat #340334, Lot #63050, Bead count=50,979) are used for all flow cytometry based counting. Antibodies used for flow cytometry consist of anti-mouse CD138-APC (eBioscience, San Diego, Calif.), anti-mouse CD19-FITC (eBioscience, San Diego, Calif.), anti-mouse kappa light chain-PE (eBioscience, San Diego, Calif.), Rat IgG$_1$-APC isotype control (eBioscience, San Diego, Calif.), Rat IgG$_{2a}$-PE isotype control (eBioscience, San Diego, Calif.). All samples are analyzed using an Accuri C6 Flow Cytometer (Accuri Cytometers, Ann Arbor, Mich.). Complete media (R10) is used for all experiments involving the ex vivo culture of splenocytes for all Elispot experiments. Complete media consists of RPMI1640 (Cellgro, Manassas, Va.), plus 1% Pen-Strep (Cellgro, Manassas, Va.), 1% L-Gln (Cellgro, Manassas, Va.), 1% NEAA (Cellgro, Manassas, Va.), β-ME (Cellgro, Manassas, Va.), plus 10% fetal bovine serum (FBS) (Cellgro, Manassas, Va.).

Luminex Analysis of Serum Cytokine Samples

For the processing of serum samples for cytokine analysis, frozen plasma at −80° C. is thawed on ice, vortexed, and centrifuged for 10 minutes to remove debris and aggregates. A total of 25-50 µL of serum is used for Luminex® assays following the manufacturer's instructions. Ten different mouse cytokines are measured using the mouse cytokine 10-plex bead kit (Invitrogen, Carlsbad, Calif., no. LMC0001). Briefly, filter plates (Millipore, Billerica, Mass., no. MAIPSWU10), are pre-wet with 200 µL of wash solution (kit component) and 25 µL of beads are added per well. Serum samples are diluted and a total volume of 50 µL is added per well (ie, 25 µL of sample serum plus 25 µL of assay diluent as provided by the manufacturer). Plates with beads are incubated for 2 hours at room temperature (RT) on an orbital shaker in the dark. At the end of the incubation, plate(s) are washed twice in kit buffer, secondary biotinylated antibody is added at a 1:10 dilution (100 µL) in biotin diluent provided with the kit. Plates are incubated at RT for 1 hour in the dark then washed twice in kit buffer. Strepavidin in assay diluent is added at 100 µL per well, then incubated for 30 minutes at RT in the dark. The plates are washed 3 times then 100 µL of kit wash solution is added and agitated for 2-3 minutes at RT in the dark. Plates are run immediately following this incubation period on a Luminex xMAP 200 unit with data acquisition and analysis software (Invitrogen, San Diego, Calif., no. MAP0200). All bead washing is performed using a vacuum manifold unit (Pall, Ann Arbor, Mich. no. 5017). For all cytokine Luminex assays, values below the limit of detection set by the lowest point along the standard or set by the manufacturer are considered out of range and are not estimated, but assumed the lowest point along the standard curve for that particular assay.

Urinalysis

Urine samples are acid precipitated for total protein recovery and analysis. Samples for which enough urine remained are used for Uristix® leukouria analysis. Briefly, a standard protein solution is prepared from normal mouse sera and is used as a standard for mouse urinary protein assay by turbidity. Standard preparation is as follows: 0, 5, 10, 15, 20, 30, 40, and 50 µL of a 4 mg/mL mouse sera standard protein solution as provided in the kit are added in duplicate into two columns. PBS is added to individual wells to adjust the final volume to 50 µL. For urine sample preparation, urine samples are centrifuged at 9880×g for 3 minutes using a tabletop microcentrifuge. Urine supernatant (1-50 µL) is added in duplicate. PBS is added to adjust the volume to 50 µL total. For the turbidity assay: 25 µL of 0.1 N HCl is added into blank columns and 250 µL of 3% sulfosalicyclic acid into the test columns. The microplate is incubated for 10 minutes at RT and plates are read using an ELISA reader with single beam at 450 nm. For the Uristix® strip assay, strips are laid out and labeled. Twenty microliters of urine are placed onto each test strip square and incubated for at least 30 seconds before the result is recorded. For all total urine analysis plate-based assays, values below the limit of detection set by the lowest point along the standard or set by the manufacturer are considered out of range and are not estimated, but assumed the lowest point along the standard curve for that particular assay.

Histology

For histological analyses, the left kidney from each animal is removed and fixed in 10% buffered neutral 10% formalin (EMD) for 48 hours on an orbital rocker at 25° C., then washed overnight with running $dH_2O$ and stored in 70% ethanol at 4° C. until ready to be processed. Kidney stains used for histological analyses included hematoxylin and eosin (H&E), Periodic Acid Schiff (PAS) and Trichrome stains (Wistar Institute, Philadelphia, Pa.). All 3 stained sections are used by the pathologist for scoring purposes. All histological scoring is performed blinded and by an independent board certified veterinary medical pathologist (Julie Engiles, VMD, DACVP). Multiple stains are used to determine score values. Images in FIG. 17 show worst affected area of section selected blindly by the pathologist.

Kidney IC-GN Scoring Method (Smith, Dong et al. 2007):
1. Glomerular cellularity—Score 1-5: Null, low, moderate, high, severe
2. Glomerular necrosis—Score 1-5: Null, low, moderate, high, severe
3. Glomerulosclerosis—Score 1-5: Null, low, moderate, high, severe
4. Interstitial infiltration—Score 1-5: Null, low, moderate, high, severe
5. Tubular atrophy—Score 1-5: Null, low, moderate, high, severe
6. Interstitial fibrosis—Score 1-5: Null, low, moderate, high, severe
7. Vasculitis—Score 1-5: Null, low, moderate, high, severe Specific Pathologist Definitions:

Necrosis is defined by the presence of nuclear debris/pyknosis within the glomerular tuft indicative of "necrosis." In many samples, this is a very mild, rare finding within only a very few segments of the glomerular tuft. Also consider effacement of the glomerular tuft by PAS positive, Trichrome negative material necrosis.

Glomerular sclerosis is defined by increased fibroplasia or fibrosis within the glomerular tuft or capsule. Sometimes glomerular sclerosis is considered an "end-stage" glomerular change, but here it is classified as those demonstrating "active" progressive fibrosis as glomerular "sclerosis."

Tubular atrophy is classified by increased luminal diameter and/or flattening of renal tubular epithelium, or drop-out of tubules.

Interstitial infiltration is considered as inflammatory infiltrates.

Vasculitis—A more loose definition of vasculitis to take into account non-inflammatory (degenerative/proliferative) vascular pathology. Most of the vascular changes are mild and could be considered "arteriosclerosis" characterized by proliferation of the smooth muscle cells, and hyalinization of the extracellular matrix. This change may reflect hypertension secondary to glomerular pathology. In very few animals is there overt "vasculitis." Most inflammatory changes are within the walls of the blood vessels, with little to no damage to the endothelium, and no overt hemorrhage/fibrin leakage. Many also have perivascular rims of fibroblasts.

Pharmacodynamic (PD) Analysis

Spleen and kidney are collected on day 118 three hours post final dose administration and snap frozen on dry ice with cooled isopentene and stored at −80° C. Lysed spleen and kidney are processed using the following protocol. Seven hundred microliters "tissue extraction buffer" generated by combining protease inhibitor cocktail (Calbiochem, no. 539136) and Halt phosphatase inhibitor cocktail (Thermo scientific, no. 78420) or Roche phosphatase inhibitor cocktail (Roche, no. 04906837001) in tissue extraction reagent I (Invitrogen, no. FNN0071) are added to each sample. Samples are homogenized frozen using a PT 10-35 Polytron homogenizer (VWR, no. 97036-082). After homogenization the sample is centrifuged at 4° C. for 2000×g for 10 minutes, supernatant is re-centrifuged at 4° C. at maximum speed, 14,000×g, for 15 minutes. Supernatants are carefully removed to avoid picking up the top layer of lipids/adipose debris. Protein concentration is adjusted to 3 mg/ml using a BCA protein assay (Pierce, no. 83228). Spleen proteasome activity is analyzed using 20S fluorogenic assay (Cayman Chemical Company, Cat #10008041, Lot #0414698-1) and modulation of proteasome activity in the kidney is analyzed using the I$\kappa$B$\alpha$ accumulation ELISA assay (Cell Signaling, Cat #7355, Lot #17). Both assays are performed per manufacture's instructions.

Spontaneous Progressive Lupus Nephritis Model

Animals

Spontaneous SLE-prone NZBWF1/J (NZM) (catalog no. 100008) female mice and non-lupus prone (within time from of experiment) NZW/LacJ (catalog no. 001058) female mice are obtained from Jackson Laboratories (Bar Harbor, Me.) at 6 weeks of age. All mice are maintained on a 24 hour light/dark cycle, with food and water available ad libitum. All experimental animal procedures are approved by and in accordance to the regulations of the Institutional Animal Care and Use Committee (IACUC) of Cephalon, Inc; approved IACUC protocol #03-040 and #03-03-041.

The NZM strain acts as a mouse model of genetically-driven, progressive, systemic lupus erythematosus (SLE). The evolution of the disease in NZM mice is characterized by an abnormal polyclonal B cell activation with a high production of various autoantibodies, including those directed against DNA and other nuclear antigens, and against cytoskeleton proteins. Elevated circulating immune complexes can lead to fatal glomerulonephritis in older mice. For experiments, animals are age-matched and studies are initiated at 28 weeks of age and mice are treated up to 40 weeks of age.

Flow Cytometry and Antibodies

Antibodies used for flow cytometry consist of anti-mouse CD138-APC (eBioscience, San Diego, Calif.), anti-mouse CD19-FITC (eBioscience, San Diego, Calif.), anti-mouse CD38-PE (eBioscience, San Diego, Calif.) and anti-mouse CD45R/B220-Cyc (eBioscience, San Diego, Calif.), Rat IgG$_1$-APC isotype control (eBioscience, San Diego, Calif.), Rat IgG$_{2a}$-PE isotype control (eBioscience, San Diego, Calif.). All samples are analyzed using an Accuri C6 Flow Cytometer (Accuri Cytometers, Ann Arbor, Mich.). Complete media is used for all experiments involving the ex vivo culture of splenocytes for all Elispot experiments. Complete media consists of RPMI1640 (Cellgro, Manassas, Va.), plus 1% Pen-Strep (Cellgro, Manassas, Va.), 1% L-Gln (Cellgro, Manassas, Va.), 1% NEAA (Cellgro, Manassas, Va.), $\beta$-ME (Cellgro, Manassas, Va.), plus 10% fetal bovine serum (FBS) (Cellgro, Manassas, Va.).

Antinuclear Antibody (ANA) ELISA Assays

The measurement of serum anti-dsDNA and anti-Smith antigen antibodies is done by an in-house generated custom ELISA assay. Chromatin coated plates are purchased from Inova Diagnostics, Inc. Purified bovine thymus dsDNA (Sigma, St. Louis, Mich.) or purified bovine Smith antigen (GenWay, San Diego, Calif.) are used as coating antigen for the detection of anti-dsDNA and anti-Smith Ag antibodies respectively. Coated plates are washed with Borate Sulfate Saline (BSS) and blocked with BSS containing 1% Bovine Serum Albumin (BSA) and 0.1% Tween-20 detergent. Standard curves are generated using mouse anti-chromatin antibody (Sigma, 2B1) or 25 week old MRL/lpr serum. Mouse anti-dsDNA antibody (Abcam, Cambridge, Mass.), or mouse anti-Smith antigen antibody (Abcam) are used as standards for each assay. Secondary antibody is purchased from Abcam (goat anti-mouse pAb-HRP), the substrate is purchased from Rockland (Gilbertsville, Pa.) (TMB), and stop reaction buffer is generated using 1 mL of concentrated sulfuric acid into 20 mL of dH$_2$O. Developed plates are read using a Victor-X4 spectrophotometer reading at 450 nM with a reference wavelength of 570 nM.

Antibody Secreting B-Cell Elispot Assays

B-cell Elispot components are ordered from MabTech (Nacka Strand, Sweden) and nitrocellulose IP filter plates are ordered from Millipore (Billerica, Mass.). Elispot wells are coated with either purified bovine thymus dsDNA (Sigma), purified bovine Smith antigen (GenWay) or boiled filtered purified chicken chromatin from lysed chicken red blood cells (Rockland, Gilbertsville, Pa.) at 10 µg/mL. Spleens are processed using glass homogenization (frosted slides). Dispersed cell contents are washed in sterile HBSS and RBCs lysed using 1×RBC lysis buffer (BioLegend, Cat #420301). Processed splenocytes are added to each well and are not stimulated with lipopolysaccharide (LPS) to avoid skewing of true ex vivo frequencies of antibody-secreting cell types (ASCs). Anti-mouse pan-IgG is used as a positive control for total IgG producing ASCs and is used to normalize results. Frequencies for each antigen are identified in an initial test phase for each model. For chromatin and total IgG only, 30,000 splenocytes are added to each well; for Smith antigen and dsDNA, 500,000 cells are added to each well. Different numbers of splenocytes are added for different antigens due to saturation limits of spot frequencies per well. B-cell Elispots are incubated overnight at 37° C. To develop each assay, secondary antibody is added to each well, incubated, washed and alkaline phosphatase strepavidin (Jackson ImmunoResearch, West Grove, Pa.) is used as the conjugate; substrate used is BCIP-NBT (MabTech, Cincinnati, Ohio). Plates are developed until spots are visible. All Elispot analyses are performed using an Immunospot C.T.L. scanner and Biospot software (Cellular Technology Ltd., Shaker Heights, Ohio). Results are shown as values from which media and cells only wells are subtracted. Some values are negative due to high background.

Luminex Analysis of Serum Cytokine Samples

For the processing of serum samples for cytokine analysis, frozen plasma at −80° C. is thawed on ice, vortexed, and centrifuged for 10 minutes (10,000×g) to remove debris and aggregates. A total of 25-50 µL of serum is used for Luminex assays following the manufacturer's instructions. Ten different mouse cytokines are measured using the mouse cytokine 20-plex bead kit (Invitrogen, Carlsbad, Calif., no. LMC0006). Briefly, filter plates (Millipore, Billerica, Mass., no. MAIPSWU10), are pre-wet with 200 µL of wash solution (kit component) and 25 µL of beads are added per well. Serum samples are diluted and a total volume of 50 µL is added per well (ie, 25 µL of sample serum plus 25 µL of assay diluent as provided by the manufacturer). Plates with beads are incubated for 2 hours at room temperature (RT) on an orbital shaker in the dark. At the end of the incubation, plate(s) are washed twice in kit buffer, secondary biotinylated antibody is added at a 1:10 dilution (100 µL) in biotin diluent provided with the kit. Plates are incubated at RT for 1 hour in the dark then washed twice in kit buffer. Strepavidin in assay diluent is added at 100 µL per well, then incubated for 30 minutes at RT in the dark. The plates are washed 3 times then 100 µL of kit wash solution is added and agitated for 2-3 minutes at RT in the dark. Plates are run immediately following this incubation period on a Luminex xMAP 200 unit with data acquisition and analysis software (Invitrogen, San Diego, Calif., no. MAP0200). All bead washing is performed using a vacuum manifold unit (Pall, Ann Arbor, Mich. no. 5017). For all cytokine Luminex assays, values below the limit of detection set by the lowest point along the standard or set by the manufacturer are considered out of range and are not estimated, but assumed the lowest point along the standard curve for that particular assay.

Urinalysis

Urine samples are acid precipitated for total protein analysis. For urine sample preparation, urine samples are centrifuged at 10,000 rpm for 3 minutes using a tabletop microcentrifuge. 1-50 μL of urine supernatant is added in duplicate. PBS is added to adjust the volume to 50 μL total. For the turbidity assay: 25 μL of 0.1 N HCl is added into blank columns and 250 μL of 3% sulfosalicyclic acid into the test columns. The microplate is incubated for 10 minutes at RT and plates are read using an ELISA reader with single beam at 450 nm. A standard protein solution is prepared from normal mouse sera and is used as a standard for mouse urinary protein assay by turbidity. Standard preparation is as follows: 0, 5, 10, 15, 20, 30, 40, and 50 μL of a 4 mg/mL mouse sera standard protein solution as provided in the kit are added in duplicate into two columns. PBS is added to individual wells to adjust the final volume to 50 μL. Samples for which enough urine remains are used for Uristix® leukouria analysis. For the Uristix® strip assay, strips are laid out and labeled. Twenty microliters of urine are placed onto each test strip square and incubated for at least 30 seconds before the result is recorded. For all total urine analysis plate-based assays, values below the limit of detection set by the lowest point along the standard or set by the manufacturer are considered out of range and are not estimated, but assumed the lowest point along the standard curve for that particular assay.

Histology

For histological analyses, the left kidney from each animal is removed and fixed in 10% buffered neutral formalin (EMD) for 48 hours on an orbital rocker at 25° C., then washed overnight with running dH$_2$O and stored in 70% ethanol at 4° C. until ready to be processed. Kidney stains used for histological analyses included hematoxylin and eosin (H&E), Periodic Acid Schiff (PAS) and Trichrome stains (Wistar Institute, Philadelphia, Pa.). All 3 stained sections are used by the pathologist for scoring purposes. All histological scoring is performed blinded and by an independent board certified veterinary medical pathologist (Julie Engiles, VMD, DACVP). Multiple stains are used to determine score values. Images in FIG. 39 show worst affected area of section selected blindly by the pathologist.

Kidney IC-GN Scoring Method (Smith, Dong et al. 2007):

1. Glomerular cellularity—Score 1-5: Null, low, moderate, high, severe
2. Glomerular necrosis—Score 1-5: Null, low, moderate, high, severe
3. Glomerulosclerosis—Score 1-5: Null, low, moderate, high, severe
4. Interstitial infiltration—Score 1-5: Null, low, moderate, high, severe
5. Tubular atrophy—Score 1-5: Null, low, moderate, high, severe
6. Interstitial fibrosis—Score 1-5: Null, low, moderate, high, severe
7. Vasculitis—Score 1-5: Null, low, moderate, high, severe Specific Pathologist Definitions:

Necrosis is defined by the presence of nuclear debris/pyknosis within the glomerular tuft indicative of "necrosis." In many samples, this is a very mild, rare finding within only a very few segments of the glomerular tuft. Also consider effacement of the glomerular tuft by PAS positive, Trichrome negative material necrosis.

Glomerular sclerosis is defined by increased fibroplasia or fibrosis within the glomerular tuft or capsule. Sometimes glomerular sclerosis is considered an "end-stage" glomerular change, but here it is classified as those demonstrating "active" progressive fibrosis as glomerular "sclerosis."

Tubular atrophy is classified by increased luminal diameter and/or flattening of renal tubular epithelium, or drop-out of tubules.

Interstitial infiltration is considered as inflammatory infiltrates.

Vasculitis—A more loose definition of vasculitis to take into account non-inflammatory (degenerative/proliferative) vascular pathology. Most of the vascular changes are mild and could be considered "arteriosclerosis" characterized by proliferation of the smooth muscle cells, and hyalinization of the extracellular matrix. This change may reflect hypertension secondary to glomerular pathology. In very few animals is there overt "vasculitis." Most inflammatory changes are within the walls of the blood vessels, with little to no damage to the endothelium, and no overt hemorrhage/fibrin leakage. Many also have perivascular rims of fibroblasts.

Collagen Type-I Cross-Linker (CTx) Bone Resorption Biomarker ELISA

Serum samples are analyzed using a commercial kit (Rat-Laps EIA, Cat #AC-06F1, Lot #4538 IDS, Scottsdale, Ariz.). Assay is performed as instructed by the manufacturer. Briefly, biotinylated ratlaps antigen is first added in each well of a 96-well ELISA plate. This plate is covered and incubated for 30 minutes at RT. Plate is washed five times with washing solution and incubated with standards or unknown samples in appropriate wells followed by primary Ab. Incubate overnight for 18 hours at 4° C. followed by washing with buffer. Secondary incubation includes a peroxidase conjugated goat anti-rabbit IgG added to each well and incubation at RT for 1 hour. Incubation with chromogenic substrate solution for 15 minutes at RT in the dark develops the plate for analysis. Stopping solution halts the reaction, absorbance is measured within 2 hours at 450 nm.

Serum C3 Complement ELISA

Serum samples are analyzed using a commercial kit (GenWay, Cat #40-374-130047, Lot #10E). Assay is performed as instructed by manufacturer. Serum samples are diluted 1 to 50,000 times in dilution buffer. Standard or unknown serum samples are added to each well and the plate is incubated at RT for 20 minutes. Plate is washed four times with wash solution buffer. Diluted enzyme-antibody conjugate is added to each well and incubated at RT for 20 minutes. Plate is washed 4 times with wash solution. TMB substrate solution is added to each well and incubated in the dark at RT for 10 minutes. Stop solution halts the reaction. Plate is read at absorbance 450 nm.

Serum IFNα ELISA

Serum samples are analyzed using a commercial kit (Interferon Source, Cat #42100-1, Lot #LF1318051 PBL, Piscataway, N.J.). Assay is performed as instructed by the manufacturer. Standards or unknown samples are added to each well and incubated for 1 hour at RT. Plate is washed once and antibody solution is added to each well and incubated for 24 hours at RT. Wells are washed 3 times and blotted to semi-dry. HRP-conjugate solution is added to each well and incubated for 1 hour at RT. Plate is then washed and incubated with TMB substrate solution for 15 minutes at RT in the dark. Optical density is determined at 450 nm 5 minutes after addition of the stop solution.

Data Analysis

Data is calculated using Microsoft Excel or Prism Graph-Pad 5.0 which is also used for graphing. Statistical analysis is performed using 1-way, 2-way ANOVA test or Mann-Whitney two-tailed paired student t-test.

Pharmacodynamic (PD) Analysis

Spleen and kidney are collected and snap frozen on dry ice with cooled isopentene and stored at −80° C. Lysis of spleen and kidney is conducted using the following protocol: Seven hundred microliters "tissue extraction buffer" generated by combining protease inhibitor cocktail (Calbiochem, no. 539136) and Halt phosphatase inhibitor cocktail (Thermo scientific, no. 78420) or Roche phosphatase inhibitor cocktail (Roche, no. 04906837001) in tissue extraction reagent I (Invitrogen, no. FNN0071) are added to each sample. Samples are homogenized frozen using a PT 10-35 Polytron homogenizer (VWR, no. 97036-082). After homogenization the sample is centrifuged at 4° C. for 2000×g for 10 minutes, supernatant is re-centrifuged at 4° C. at maximum speed, 14,000×g, for 15 minutes. Supernatants are carefully removed to avoid picking up the top layer of lipids/adipose debris. Protein concentration is adjusted to 3 mg/ml using a BCA protein assay (Pierce, no. 83228). Spleen proteasome activity is analyzed using 20S fluorogenic assay (Cayman Chemical Company, Cat #10008041, Lot #0414698-1) and modulation of proteasome activity in the kidney is analyzed using the IκBα accumulation ELISA assay (Cell Signaling, Cat #7355, Lot #17). Both assays are performed per manufacture's instructions.

EXAMPLES

Example 1

COMPOUND A Effectively Treats Lupus in MRL/lpr Mice

Protocol

MRL/lpr mice are first randomized, initial bleeds collected, and body weights recorded for baseline measurements (FIG. 1). All mice are individually ear tagged and are monitored throughout the entire experiment (e.g., "Group#-Cage letter-Mouse#", so "3B5"=Group 3 (G3), cage B, mouse #5). Mice are age-matched and treatment started at 6-8 weeks of age. Cheek bleeds and urine collection continues weekly throughout the experiment. Mice are individually tracked for several parameters including cytokine and ANA levels, proteinuria, body mass, lymphomegaly, general health, and mortality. All parameters are evaluated bi-monthly except mortality which is monitored daily. All groups consist of a minimum of at least 10-12 mice per group. Ex vivo experiments include flow cytometry analyses for plasma cells, serum complement C3 and ANA levels; urine protein and leukocytes, serum cytokine profiling, renal histo pathology, and determination of compound levels (pharmacokinetics (PK)) in the spleen, kidney and plasma. Mice are tracked on an individual basis. For all data, mice are grouped into populations and data graphed as mean±SEM. End-stage readouts are analyzed as described in the MATERIALS AND METHODS section (above) and in FIG. 1.

As shown in FIG. 1, mice are treated either iv or ip with COMPOUND A or bortezomib, or orally with COMPOUND A. Standard of care agent used is dexamethasone in saline. Vehicle alone is provided orally twice weekly (p.o.). Both proteasome inhibitors are suspended in the vehicle solution. Bi-monthly bleeds and urine are collected and frozen at 80° C. until assayed. End analyses include kidney histology, splenocyte B-cell Elispots, flow cytometry for B and T cell populations, PD markers, serum cytokines, antibody and complement levels. In addition, urine proteinuria is determined for all animals.

Initially the group one (G1) dose of COMPOUND A was 4 mg/kg, iv once weekly. Due to animal mortality (4 out of 15 mice total at day 71) in this group, the dose was modified to 3 mg/kg iv once per week. Animals that died at COMPOUND A 4 mg/kg dose were not included in the analyses. In group two (G2), COMPOUND A was administered at a dose of 3 mg/kg iv twice weekly. In group three (G3), COMPOUND A was administered at a dose of 10 mg/kg p.o. twice weekly. In group four (G4), bortezomib was initially administered at a dose of 0.5 mg/kg iv twice weekly. However, due to animal mortality in this group, the group was split into two groups, G4 and G5, and in the new G4 group bortezomib was administered at a dose of 0.5 mg/kg iv once weekly. In the new group five (G5), bortezomib was administered at a dose of 0.3 mg/kg iv twice weekly. Dexamethasone was administered at a dose of 1.5 mg/kg/2d (M, W, F) ip. Vehicle was 3% DMSO/ 10% Solutol/87% PBS. In those instances in which mice could not be injected via the iv route, agents were administered ip as noted in Table 1.

TABLE 1

Days and Route of Injections

| Day | G1 | G2 | G3 | G4 | G5 | G6 | G7 |
|---|---|---|---|---|---|---|---|
| 1 | IV (4 mg/kg) | IV | PO | IV | | IP | PO |
| 4 | IP (4 mg/kg) | IP | PO | IP | | IP | PO |
| 7 | | | | | | IP | |
| 8 | IV (4 mg/kg) | IV | PO | IV | | IP | PO |
| 11 | | IV | PO | | | IP | PO |
| 14 | IV (4 mg/kg) | IP | PO | IP | IP | IP | PO |
| 16 | | | | | | IP | |
| 17 | | IP | PO | | IP | | PO |
| 18 | | | | | | IP | |
| 21 | IP (4 mg/kg) | IP | PO | IP | IP | IP | PO |
| 23 | | | | | | IP | |
| 24 | | IP | PO | | IP | | PO |
| 25 | | | | | | IP | |
| 28 | IV (4 mg/kg) | IV | PO | IV | IV | IP | PO |
| 29 | | | | | | IP | |
| 31 | | IP | PO | | IP | IP | PO |
| 35 | IP (4 mg/kg) | IP | PO | IP | IP | IP | PO |
| 36 | | | | | | IP | |
| 38 | | IP | PO | | IP | IP | PO |
| 42 | IV (4 mg/kg) | IV | PO | IV | IV | IP | PO |
| 44 | | | | | | IP | |
| 45 | | IP | PO | | IP | | PO |
| 46 | | | | | | IP | |
| 49 | IV (4 mg/kg) | IV | PO | IV | IV | IP | PO |
| 51 | | | | | | IP | |
| 52 | | IP | PO | | IP | | PO |
| 53 | | | | | | IP | |
| 56 | IV (4 mg/kg) | IV | PO | IV | IV | IP | PO |
| 58 | | | | | | IP | |
| 59 | | IP | PO | | IP | | PO |
| 60 | | | | | | IP | |
| 63 | | | | | | IP | |
| 64 | IV (4 mg/kg) | IV | PO | IV | IV | | PO |
| 65 | | | | | | IP | |
| 67 | | IP | PO | | IP | IP | PO |
| 70 | | | | | | IP | |
| 71 | IV (4 mg/kg) | IV | PO | IV | IV | | PO |
| 72 | | | | | | IP | |
| 74 | | IP | PO | | IP | IP | PO |
| 77 | IP (3 mg/kg) | IP | PO | IP | IP | IP | PO |
| 81 | | IP | PO | | IP | IP | PO |
| 83 | | | | | | IP | |

TABLE 1-continued

Days and Route of Injections

| Day | G1 | G2 | G3 | G4 | G5 | G6 | G7 |
|---|---|---|---|---|---|---|---|
| 85 | IV (3 mg/kg) | IV | PO | IV | IV | IP | PO |
| 86 | | | | | | IP | |
| 88 | | IP | PO | | IP | IP | PO |
| 91 | IV (3 mg/kg) | IV | PO | IV | IV | IP | PO |
| 93 | | | | | | IP | |
| 94 | | IP | PO | | IP | IP | PO |
| 98 | IV (3 mg/kg) | IV | PO | IV | IV | IP | PO |
| 100 | | | | | | IP | |
| 101 | | IP | PO | | IP | | PO |
| 102 | | | | | | IP | |
| 105 | | | | | | IP | |
| 106 | IV (3 mg/kg) | IV | PO | IV | IV | | PO |
| 107 | | | | | | IP | |
| 109 | | IP | PO | | IP | IP | PO |
| 113 | IV (3 mg/kg) | IV | PO | IV | IV | IP | PO |
| 114 | | | | | | IP | |
| 116 | | IP | PO | | IP | IP | PO |
| 119 | IP (3 mg/kg) | IP | PO | IP | IP | IP | PO |

Body Weight and Survival

Figure 2:
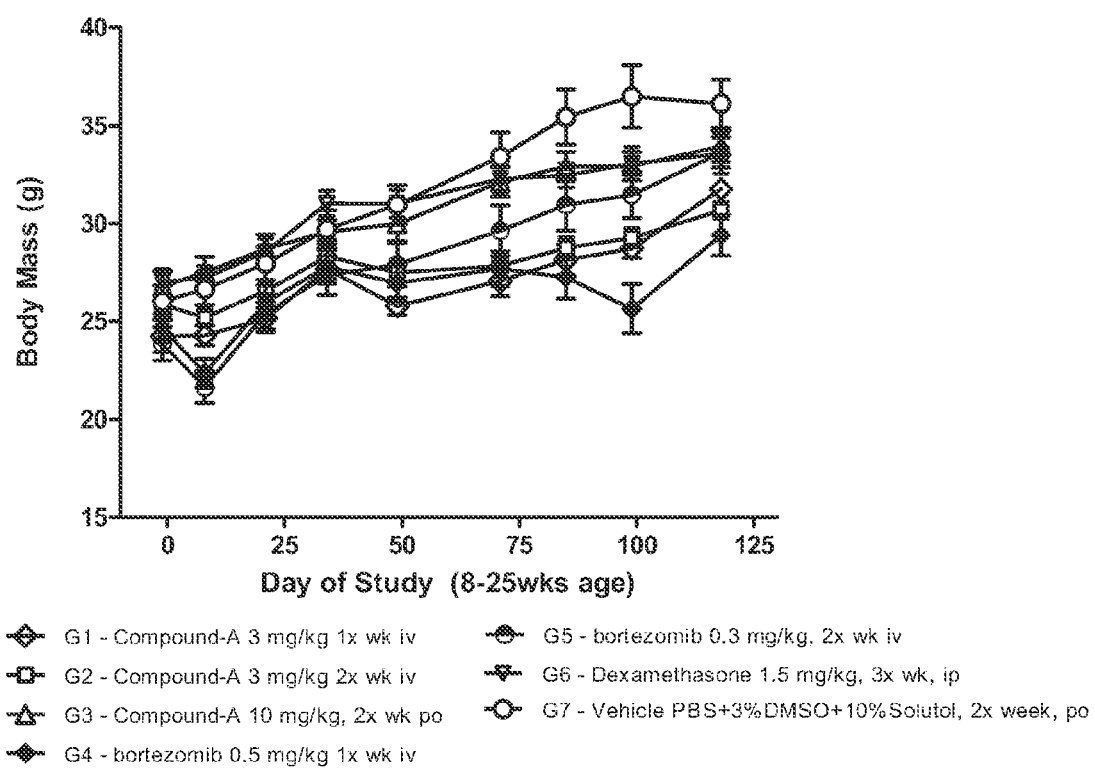
FIG. 2 depicts the body weight progression of MRL/lpr mice across treatment groups for the study duration. MRL/lpr mice were treated as outlined in the legend. Graph shows Mean±SEM body mass for each group the duration of the study.

The body weight of MRL/lpr mice in the treatment groups decreased as compared to vehicle (see FIG. 2 and Tables 2 and 20). Body weight loss was equivalent in all treated animals except for those in the bortezomib (0.5 mg/kg iv once weekly) and COMPOUND A (3 mg/kg iv once weekly) groups which compared to the vehicle group had reduced body mass (17% and 15% decrease respectively; $p<0.05$).

TABLE 2

Statistics for Group Comparisons: Body Weight Progression for MRL/lpr Mice across Treatment Groups for the Study Duration

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G1: COMPOUND A, 3 mg/kg 1× wk iv | NS | NS | NS | $p < 0.05$ |
| G2: COMPOUND A, 3 mg/kg 2× wk iv | NS | NS | NS | NS |
| G3: COMPOUND A, 10 mg/kg 2× wk po | NS | NS | NS | NS |
| G6: Dexamethasone, 1.5 mg/kg 3× wk ip | NS | NS | NA | NS |
| G7: Vehicle, 2× wk po | $p < 0.05$ | NS | NS | NA |

Figure 3:
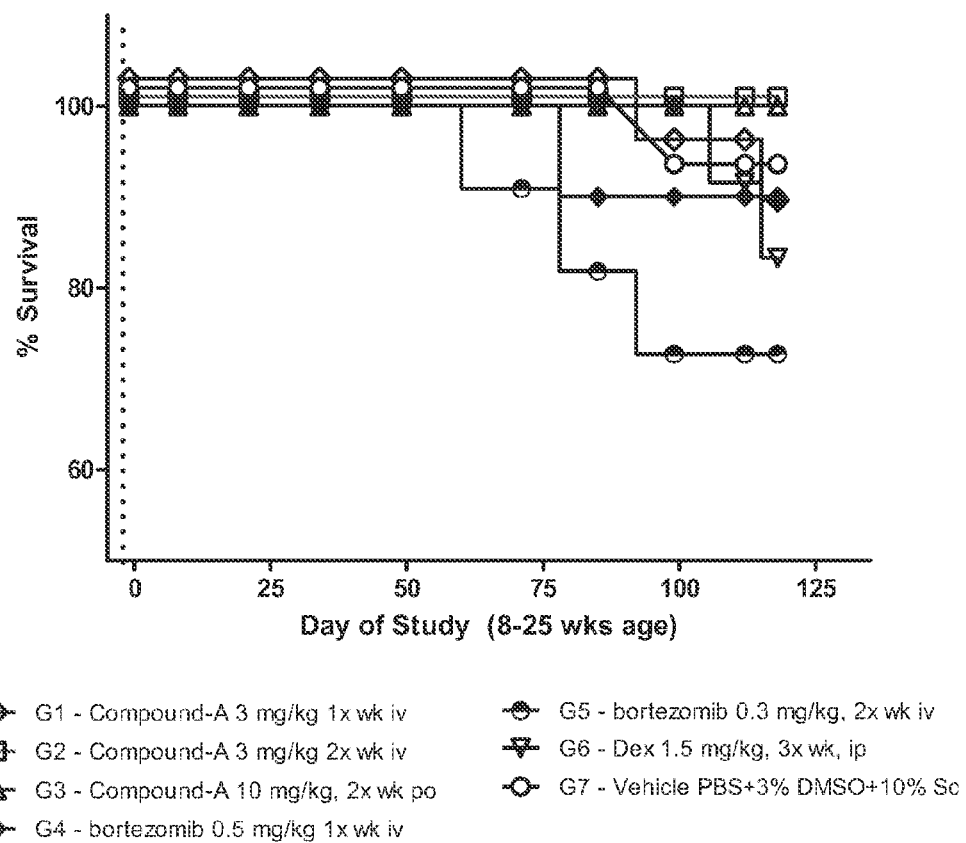
FIG. 3 depicts the survival of MRL/lpr mice across treatment groups for the study duration. MRL/lpr mice were treated as outlined in the legend. Graph shows percent of live mice for each week of the experiment.

Statistics used for comparisons was 1-way ANOVA;
NS = not significant ($p > 0.05$);
NA = not applicable COMPOUND A treatment resulted in a 5% increase in survival for 0.3 mg/kg once weekly regimen and 8.4% increase in survival for 0.3 mg/kg iv and 10 mg/kg oral, twice weekly regimen over that of vehicle (see FIG. 3 and Tables 3 and 20). Bortezomib treatment was associated with unexpected toxicities based upon initial dose range finding studies and resulted in a 2% decrease (0.5 mg/kg iv once weekly) and 19% decrease (0.3 mg/kg iv twice weekly) in survival over that of vehicle at EOS. Increased survival was observed for COMPOUND A-treatment groups relative to both of the bortezomib treatment groups ($p<0.05$) (see FIG. 3 and Tables 3 and 20). Greater mortality in the lower dose of bortezomib combined with the extended survival provided by COMPOUND A treatment suggests that bortezomib is both less effective at preventing disease related mortality and less well tolerated than COMPOUND A.

TABLE 3

Statistics for Group Comparisons: Survival for MRL/lpr Mice across Treatment Groups for the Study Duration

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G1: COMPOUND A, 3 mg/kg 1× wk iv | NS | $p < 0.05$ | NS | NS |
| G2: COMPOUND A, 3 mg/kg 2× wk iv | $P < 0.05$ | $p < 0.05$ | NS | NS |
| G3: COMPOUND A, 10 mg/kg 2× wk po | $P < 0.05$ | $p < 0.05$ | NS | NS |
| G6: Dexamethasone, 1.5 mg/kg 3× wk ip | NS | $p < 0.05$ | NA | NS |
| G7: Vehicle, 2× wk po | NS | $p < 0.05$ | NS | NA |

Figure 4:
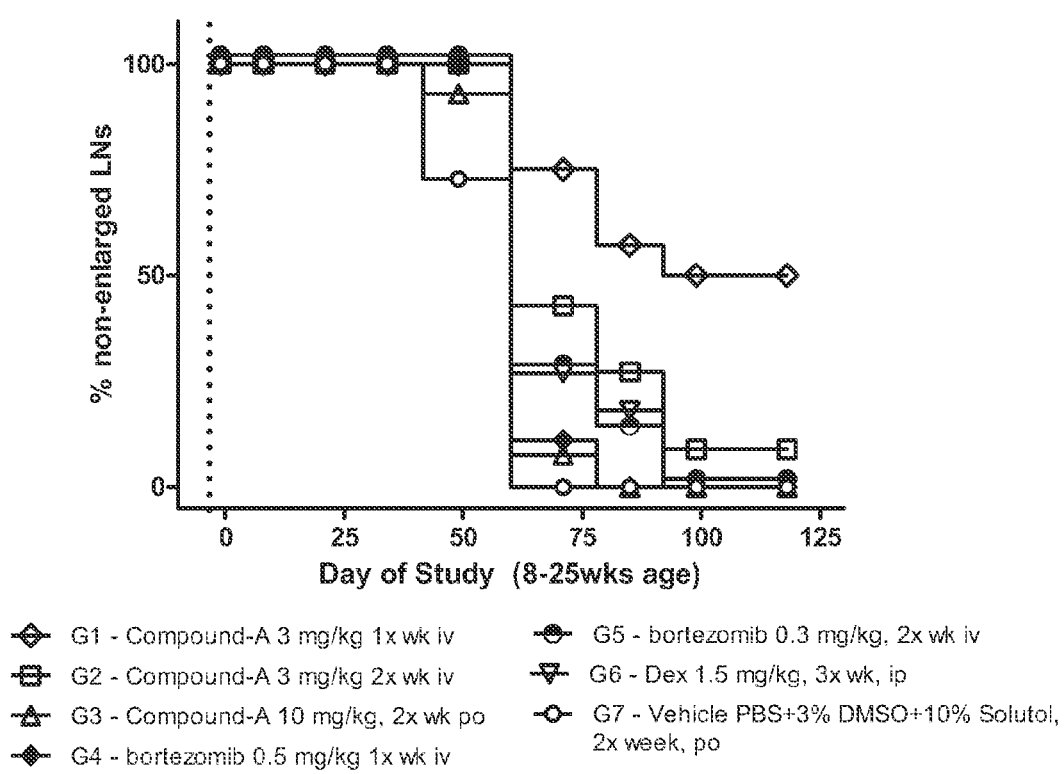
FIG. 4 depicts lymphomegaly for MRL/lpr mice across treatment groups for the study duration. MRL/lpr mice were treated as outlined in the legend. Lymphomegaly or presence of enlarged lymph nodes were observed weekly and noted. Graph shows percent of mice with non-enlarged lymph nodes (LNs).
Figure 5:
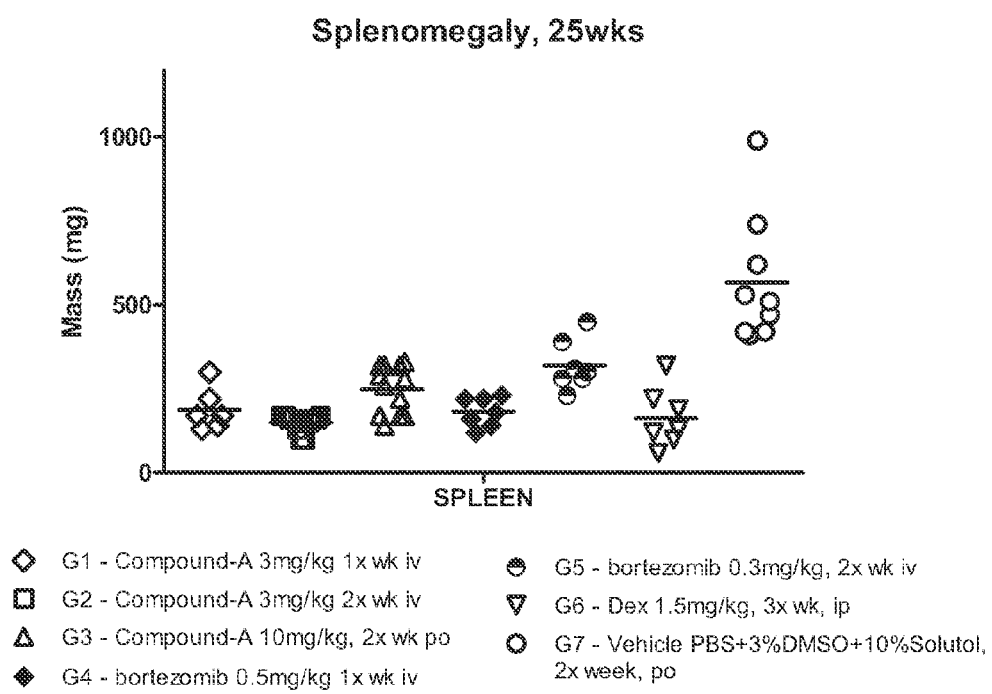
FIG. 5 depicts splenomegaly for MRL/lpr mice across treatment groups for the study duration. MRL/lpr mice were treated as outlined in the legend. The spleen masses for all mice that survived until the end of the experiment are graphed. Each symbol represents the spleen weight for one mouse at 25 weeks of age.

Statistics used for comparisons was a Mann-Whitney two-tailed paired t-test;
NS = not significant ($p > 0.05$);
NA = not applicable Lymphomegaly and Splenomegaly MRL/lpr mice treated iv with COMPOUND A exhibited reduced lymphomegaly (ie presence of swollen cervical lymph nodes) as compared to vehicle (71% and 34% decrease; $p<0.05$) (see FIG. 4 and Tables 4 and 20). Bortezomib treatment did not significantly reduce lymphomegaly. A reduction in splenomegaly (spleen swelling) was observed for all treatment groups as compared to the vehicle treatment group (568 mg down to 150-300 mg by EOS) ($p<0.01$) (see FIG. 5 and Table 5). The greatest decrease was observed for the COMPOUND A 3 mg/kg iv twice weekly treatment groups as compared to the vehicle treatment groups at the end of the study (74% decrease, $p<0.001$) (see Table 20).

TABLE 4

Statistics for Group Comparisons: Lymphomegaly for MRL/lpr Mice across Treatment Groups for the Study Duration

| Group | G4 Bortezomib, 0.5 mg/kg 1× wk i.v. | G5 Bortezomib 0.3 mg/kg, 2× wk i.v. | G6 Dexa-methasone 1.5 mg/kg, 3× wk i.p. | G7 Vehicle, 2× wk p.o. |
|---|---|---|---|---|
| G1: COMPOUND A, 3 mg/kg 1× wk iv | $p < 0.05$ | $p < 0.05$ | $p < 0.05$ | $p < 0.05$ |
| G2: COMPOUND A, 3 mg/kg 2× wk iv | NS | $p < 0.05$ | $p < 0.05$ | $p < 0.05$ |
| G3: COMPOUND A, 10 mg/kg 2× wk po | NS | NS | NS | NS |
| G6: Dexamethasone, 1.5 mg/kg 3× wk ip | NS | NS | NA | NS |
| G7: Vehicle, 2× wk po | NS | NS | NS | NA |

Statistics used for comparisons was a Mann Whitney two-tailed paired t-test;
NS = not significant ($p > 0.05$);
NA = not applicable

TABLE 5

Statistics for Group Comparisons: Splenomegaly for MRL/lpr Mice across Treatment Groups for the Study Duration

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G1: COMPOUND A, 3 mg/kg 1× wk iv | NS | $p < 0.05$ | NS | $p < 0.01$ |

TABLE 5-continued

Statistics for Group Comparisons: Splenomegaly for MRL/lpr
Mice across Treatment Groups for the Study Duration

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G2: COMPOUND A, 3 mg/kg 2× wk iv | NS | p < 0.001 | NS | p < 0.001 |
| G3: COMPOUND A, 10 mg/kg 2× wk po | NS | NS | p < 0.05 | p < 0.001 |
| G6: Dexamethasone, 1.5 mg/kg 3× wk ip | NS | p < 0.05 | NA | p < 0.001 |
| G7: Vehicle, 2× wk po | p < 0.01 | p < 0.01 | p < 0.001 | NA |

Statistics used for comparisons was a two-tailed Mann-Whitney t-test;
NS = not significant (p > 0.05);
NA = not applicable.

These results are important because splenomegaly and lymphomegaly are indicative of lupus disease in MRL/lpr mice. Therefore, the reduction in spleen and lymph node size indicates that COMPOUND A partially controlled systemic autoimmune responses during treatment. Significantly, COMPOUND A was superior to bortezomib in reducing lymphomegaly, and was superior to the twice weekly dose of bortezomib in reducing splenomegaly.

Serum Cytokines

Figure 6:
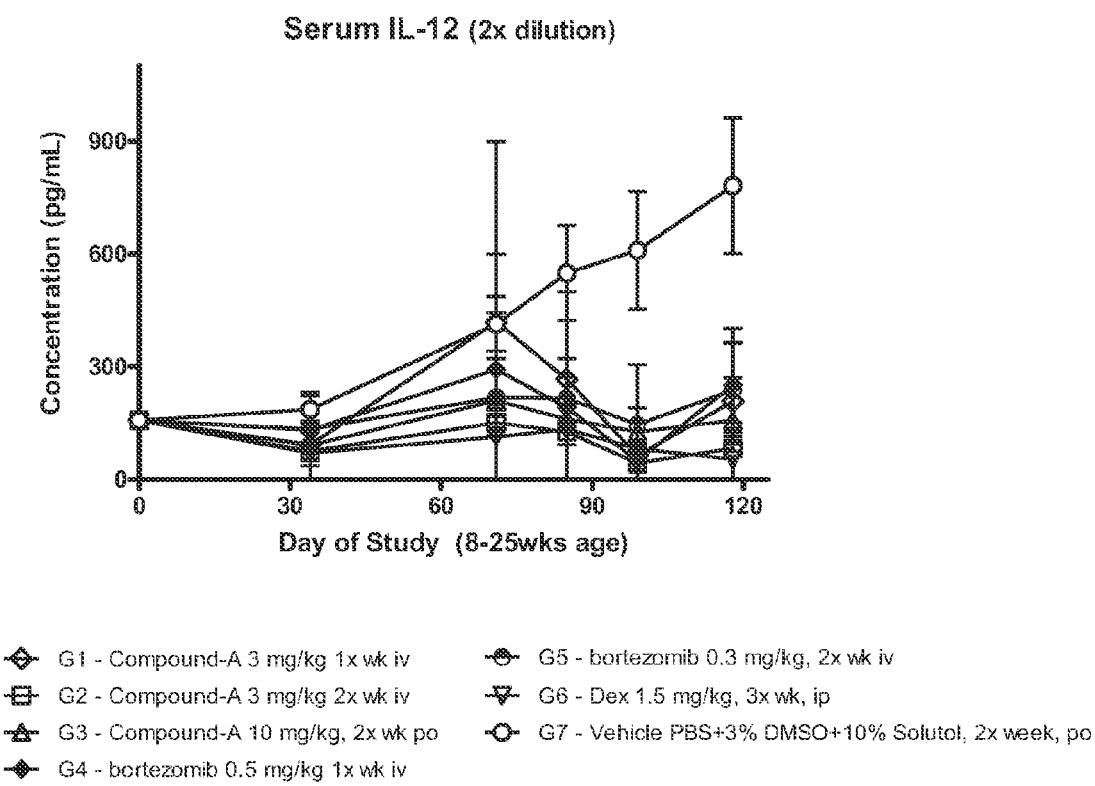
FIG. 6 depicts serum IL-12p40/p70 concentration over course of disease treatment in MRL/lpr mice. MRL/lpr mice were treated as outlined in the legend. Graph shows Mean±SEM for the concentration of mouse serum IL-12p40/p70 from treated MRL/lpr mice. Cytokines were analyzed using Luminex bead kits.
Figure 7:
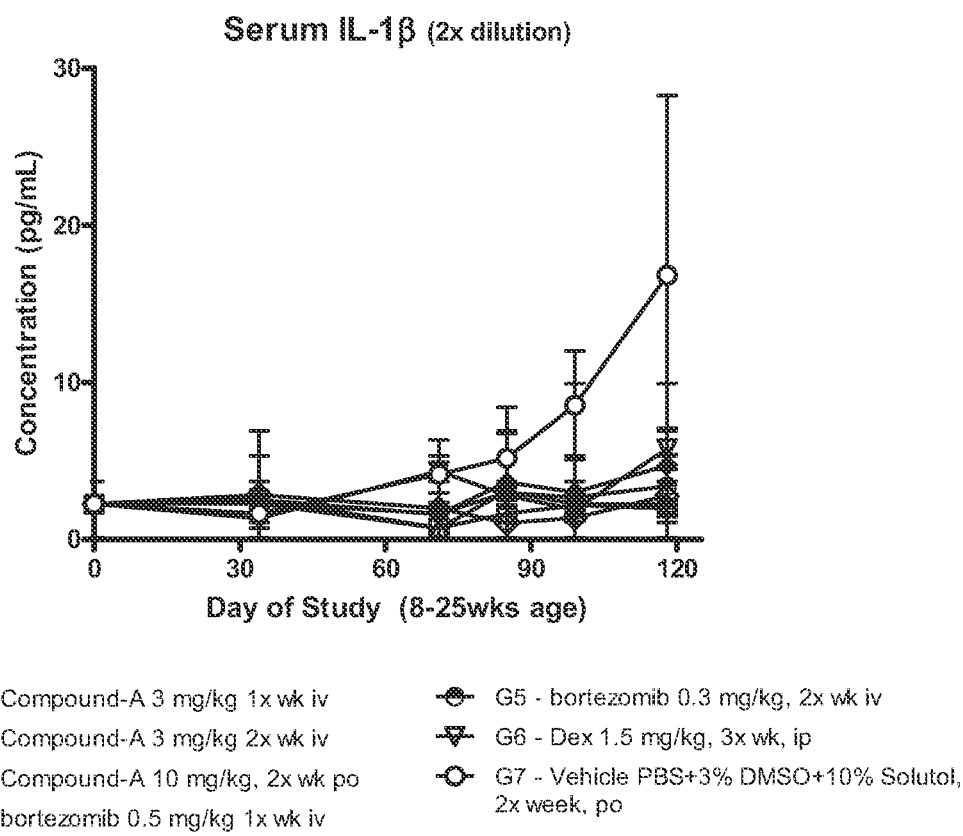
FIG. 7 depicts serum IL-1β concentration over course of disease treatment in MRL/lpr mice. MRL/lpr mice were treated as outlined in the legend. Graph shows Mean±SEM for the concentration of mouse serum IL-1b from treated MRL/lpr mice. Cytokines were analyzed using Luminex bead kits.
Figure 8:
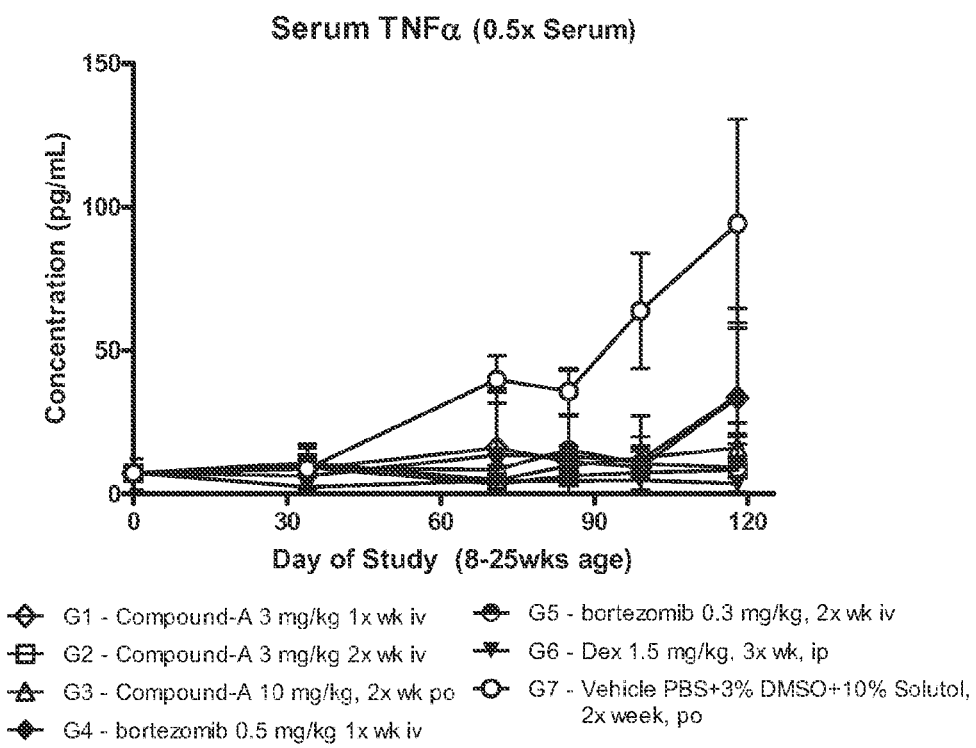
FIG. 8 depicts serum TNFα concentration over course of disease treatment in MRL/lpr mice. MRL/lpr mice were treated as outlined in the legend. Graph shows Mean±SEM for the concentration of mouse serum TNFα from treated MRL/lpr mice. Cytokines were analyzed using Luminex bead kits.

MRL/lpr mice treated with COMPOUND A exhibited reduced levels of several serum cytokines (IL-12p40/p70, TNFα and IL-1β) compared to the vehicle-treated mice (see Table 20). All three COMPOUND A treatment regimens significantly impacted serum IL-12 levels, whereas only the highest dose of bortezomib at 0.5 mg/kg 1× week iv significantly reduced IL-12 levels below vehicle treated animals (p<0.05, see FIG. 6 and Table 6). All treatment groups reduced serum IL-1β as compared to vehicle, but only the COMPOUND A 3 mg/kg twice weekly dose provided a significant reduction (16.8 pg/mL down to 5.7 pg/mL by EOS) (p<0.05) (see FIG. 7 and Table 7). All treatment groups experienced a decrease in serum TNFα as compared to vehicle (see FIG. 8 and Tables 8 and 20).

TABLE 6

Statistics for Group Comparisons: Serum IL-12p40/p70 Concentration Over Course of Disease Treatment in MRL/lpr Mice

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G1: COMPOUND A, 3 mg/kg 1× wk iv | NS | NS | NS | p < 0.05 |
| G2: COMPOUND A, 3 mg/kg 2× wk iv | NS | NS | NS | p < 0.001 |
| G3: COMPOUND A, 10 mg/kg 2× wk po | NS | NS | NS | p < 0.001 |
| G6: Dexamethasone, 1.5 mg/kg 3× wk ip | NS | NS | NA | p < 0.001 |
| G7: Vehicle, 2× wk po | p < 0.001 | NS | p < 0.001 | NA |

Statistics used for comparisons was 1-way ANOVA;
NS = not significant (p > 0.05);
NA = not applicable

TABLE 7

Statistics for Group Comparisons: Serum IL-1β Concentration Over Course of Disease Treatment in MRL/lpr Mice

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G1: COMPOUND A, 3 mg/kg 1× wk iv | NS | NS | NS | NS |
| G2: COMPOUND A, 3 mg/kg 2× wk iv | NS | NS | NS | p < 0.05 |
| G3: COMPOUND A, 10 mg/kg 2× wk po | NS | NS | NS | NS |
| G6: Dexamethasone, 1.5 mg/kg 3× wk ip | NS | NS | NA | NS |
| G7: Vehicle, 2× wk po | NS | NS | NS | NA |

Statistics used for comparisons was 1-way ANOVA;
NS = not significant (p > 0.05);
NA = not applicable

TABLE 8

Statistics for Group Comparisons: Serum TNFα Concentration Over Course of Disease Treatment in MRL/lpr Mice

| Group | G4 Bortezomib, 0.5 mg/kg 1× wk iv | G5 Bortezomib 0.3 mg/kg, 2× wk iv | G6 Dexa-methasone 1.5 mg/kg, 3× wk ip | G7 Vehicle, 2× wk po |
|---|---|---|---|---|
| G1: COMPOUND A, 3 mg/kg 1× wk iv | NS | NS | NS | p < 0.05 |
| G2: COMPOUND A, 3 mg/kg 2× wk iv | NS | NS | NS | p < 0.01 |
| G3: COMPOUND A, 10 mg/kg 2× wk po | NS | NS | NS | p < 0.01 |
| G6: Dexamethasone, 1.5 mg/kg 3× wk ip | NS | NS | NA | p < 0.001 |
| G7: Vehicle, 2× wk po | P < 0.05 | p < 0.01 | p < 0.001 | NA |

Statistics used for comparisons was 1-way ANOVA;
NS = not significant (p > 0.05);
NA = not applicable This data is important because IL-12 and IL-10 are elevated in lupus patients and can be used as prognostic markers of disease progression (Chun et al 2007, Tucci et al 2008). Several of the common pro-inflammatory cytokines are also elevated during the course of lupus disease such as IL-1β and TNFα, (Aringer et al 2004). COMPOUND A was superior to bortezomib in that treatment with COMPOUND A significantly reduced IL-12, but treatment with bortezomib twice weekly was ineffective. In addition, the twice weekly COMPOUND A dose was the only treatment that significantly reduced IL-1β.

C3

MRL/lpr mice treated orally with COMPOUND A exhibited significantly increased serum C3 concentration relative to vehicle (128% increase over vehicle at day 99; p<0.001). COMPOUND A was superior to bortezomib in this respect because the bortezomib treatment groups did not exhibit a significant increase in serum C3 relative to vehicle.

This data is important because the level of C3 in the serum is indirectly correlated to the magnitude or extent of inflammation. SLE patients show reduced levels of C3 and C4 over time, which is indicative of increased systemic inflammation, which results in tissue organ damage. But with treatment these factors rebound, indicating that the treatment is reducing systemic inflammation and thus effectively treating the disease. Therefore, an increase in serum C3 is indicative of lupus disease resolution and treatment (Boumpas, Furie et al. 2003).

Antibody-Secreting Cells

Figure 9:
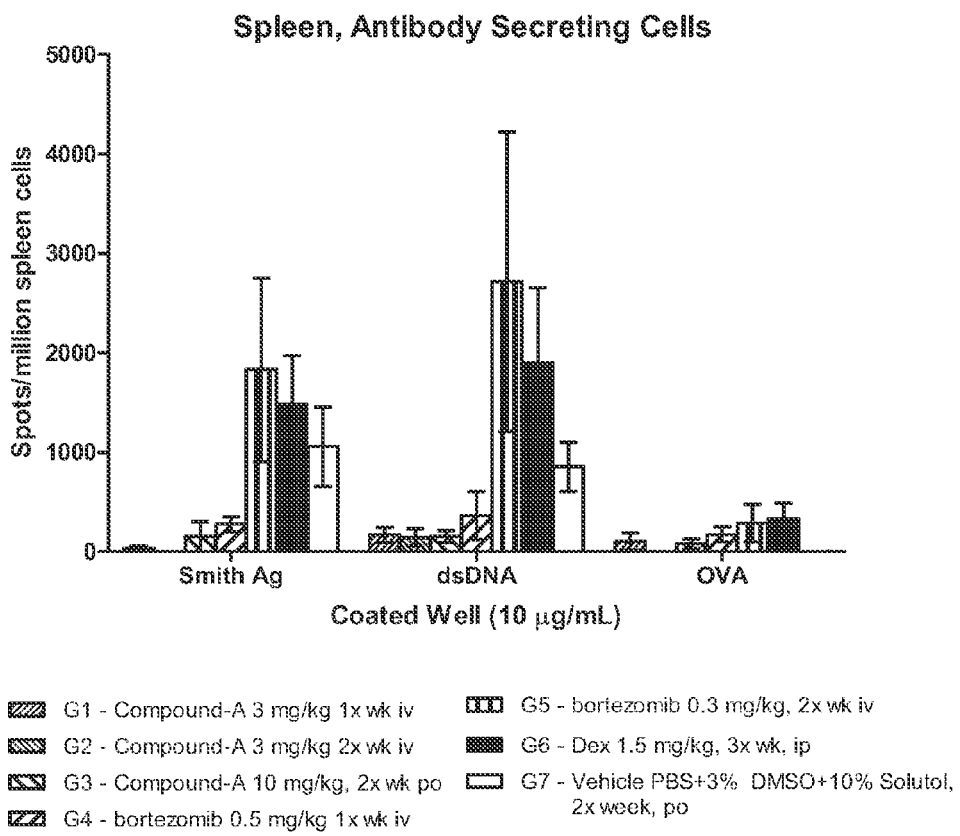
FIG. 9 depicts frequency of anti-Smith antigen and anti-dsDNA antibody secreting cells in the spleens of MRL/lpr mice. MRL/lpr treated mice spleens were processed for splenocytes for ex vivo Elispot assays. Elispot wells were coated with 10 µg/mL of smith antigen, dsDNA or ovalbumin protein. Fresh, whole splenocytes were added to each well at 500,000 cells per well in cell culture medium. Cells were incubated overnight at 37° C. Developed wells provided spots that were counted as frequency of ASCs per million splenocytes. Graph shows Mean±SEM.
Figure 10:
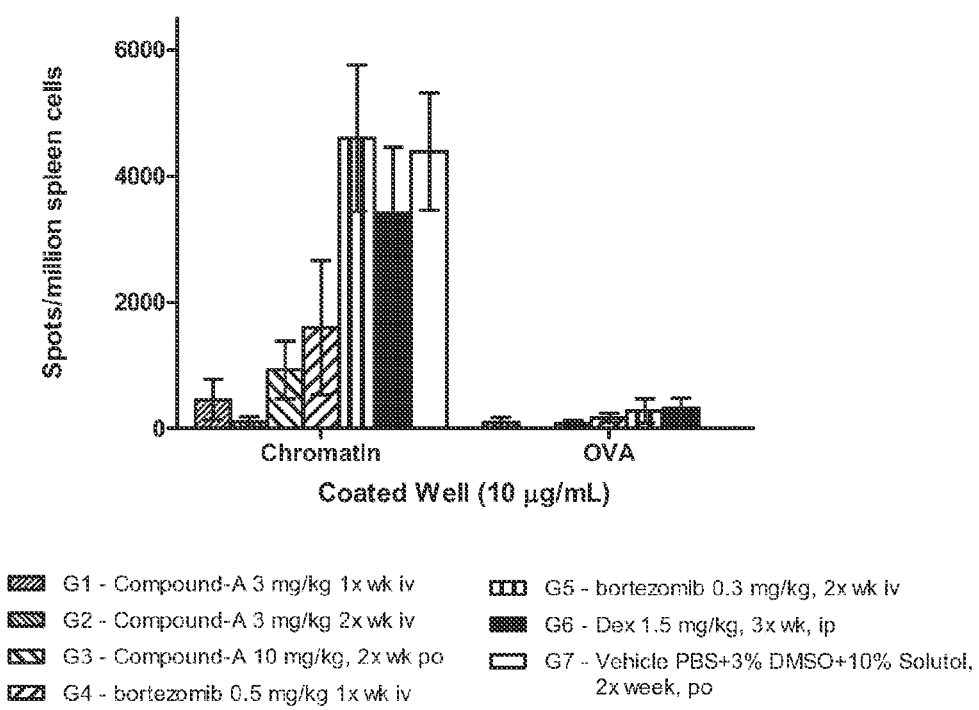
FIG. 10 depicts the frequency of anti-chromatin antibody secreting cells in the spleens of MRL/lpr mice. MRL/lpr treated mice spleens were processed for splenocytes for ex vivo Elispot assays. Elispot wells were coated with 10 µg/mL of boiled chicken chromatin or ovalbumin protein. Fresh, whole splenocytes were added to each well at 50,000 cells per well in cell culture medium. Cells were incubated overnight at 37° C. Developed wells provided spots that were counted as frequency of ASCs per million splenocytes. Graph shows Mean±SEM.

MRL/lpr mice treated with COMPOUND A exhibited a reduced frequency of anti-Smith Ag and anti-dsDNA IgG producing antibody-secreting cells (ASC) as compared to vehicle (97%, 100% and 86% decrease for Smith Ag; 80%, 84%, 82% decrease for dsDNA ASCs for Groups 1-3, respectively) (see FIG. 9 and Tables 9 and 20; p<0.01-p<0.05). MRL/lpr mice treated iv with COMPOUND A exhibited a reduced frequency of anti-Smith Ag ASC as compared to bortezomib (see FIG. 9 and Table 9; p<0.01-p<0.05). MRL/lpr mice treated with COMPOUND A exhibited a reduced frequency of anti-Smith Ag and anti-dsDNA IgG producing ASC as compared to both bortezomib 0.3 mg/kg iv twice weekly and dexamethasone (see FIG. 9 and Table 9; p<0.01-p<0.05). MRL/lpr mice treated with COMPOUND A exhibited a reduced frequency of anti-chromatin IgG-producing spleen ASC below that of bortezomib 0.3 mg/kg iv twice weekly, dexamethasone, and vehicle (see FIG. 10 and Table 10; p<0.01-p<0.05).

This data is important because circulating autoantibody secreting cell types are directly correlative to a poor SLE prognosis (Neubert et al 2008, Sanz et al 2010, Muller et al 2008). Significantly, COMPOUND A was superior to bortezomib in reducing anti-Smith Ag ASC, and the weekly and twice weekly iv doses of COMPOUND A dose were both superior to the twice weekly dose of bortezomib in reducing both anti-dsDNA IgG producing ASC and anti-chromatin IgG-producing spleen ASC.

Antinuclear Antibodies (ANAs)

Figure 11:
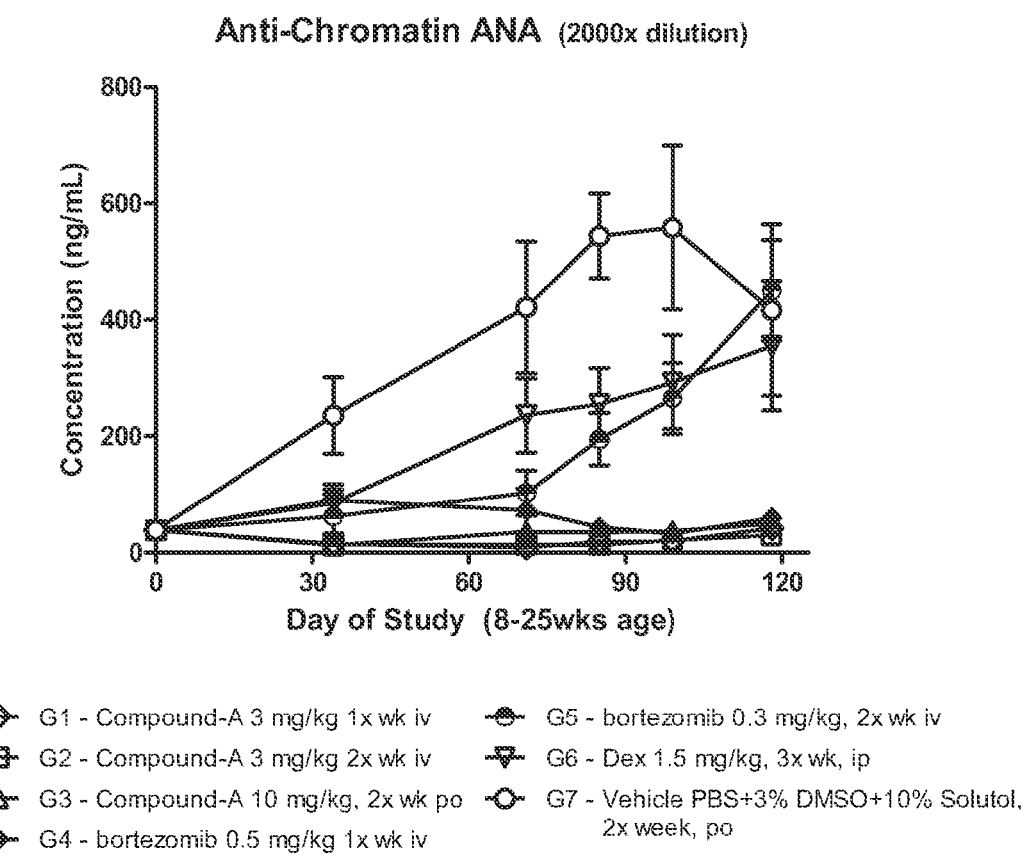
FIG. 11 depicts anti-chromatin anti-nuclear antibody concentrations in MRL/lpr mice over time. Treated MRL/lpr mouse serum samples were analyzed for the presence of anti-chromatin IgG circulating ANAs via ELISA assay (see Materials and Methods). Graph shows Mean±SEM of anti-chromatin ANA concentration in ng/ml, 2000-fold dilution from original stock.
Figure 12:
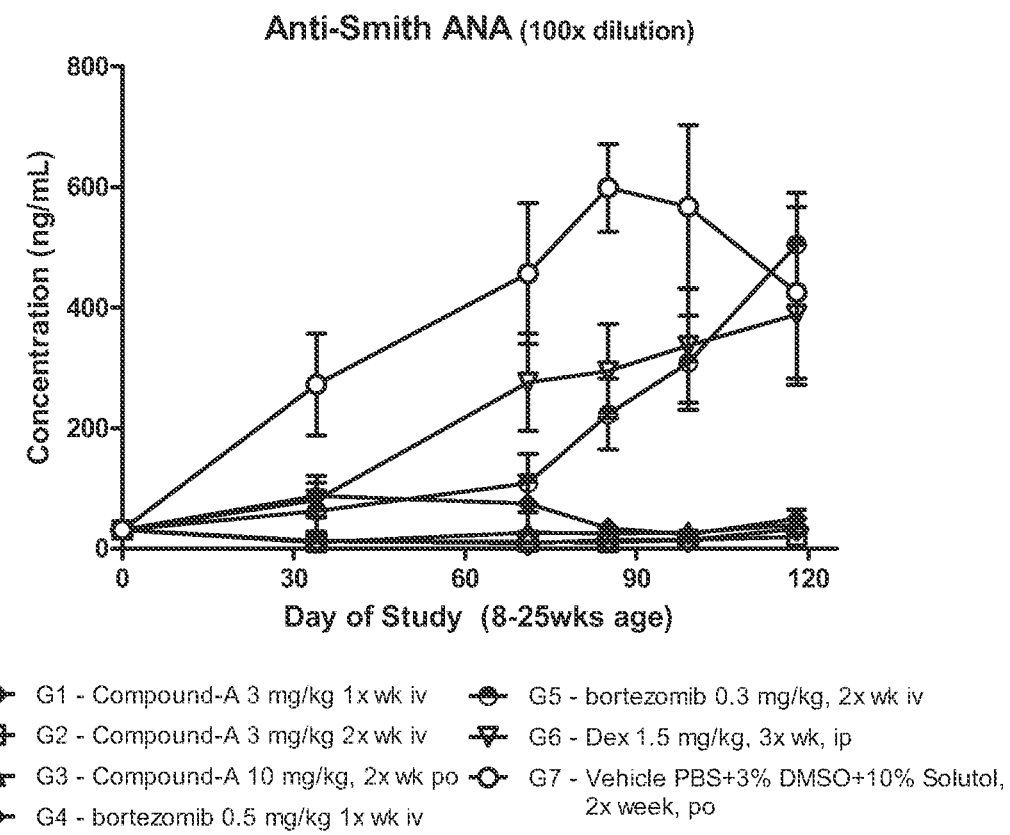
FIG. 12 depicts anti-Smith antigen antinuclear antibody concentrations in MRL/lpr mice over time. Treated MRL/lpr mouse serum samples were analyzed for the presence of anti-smith antigen IgG circulating ANAs via ELISA assay (see Materials and Methods). Graph shows Mean±SEM of anti-smith antigen ANA concentration in ng/mL, 100-fold dilution from original stock.
Figure 13:
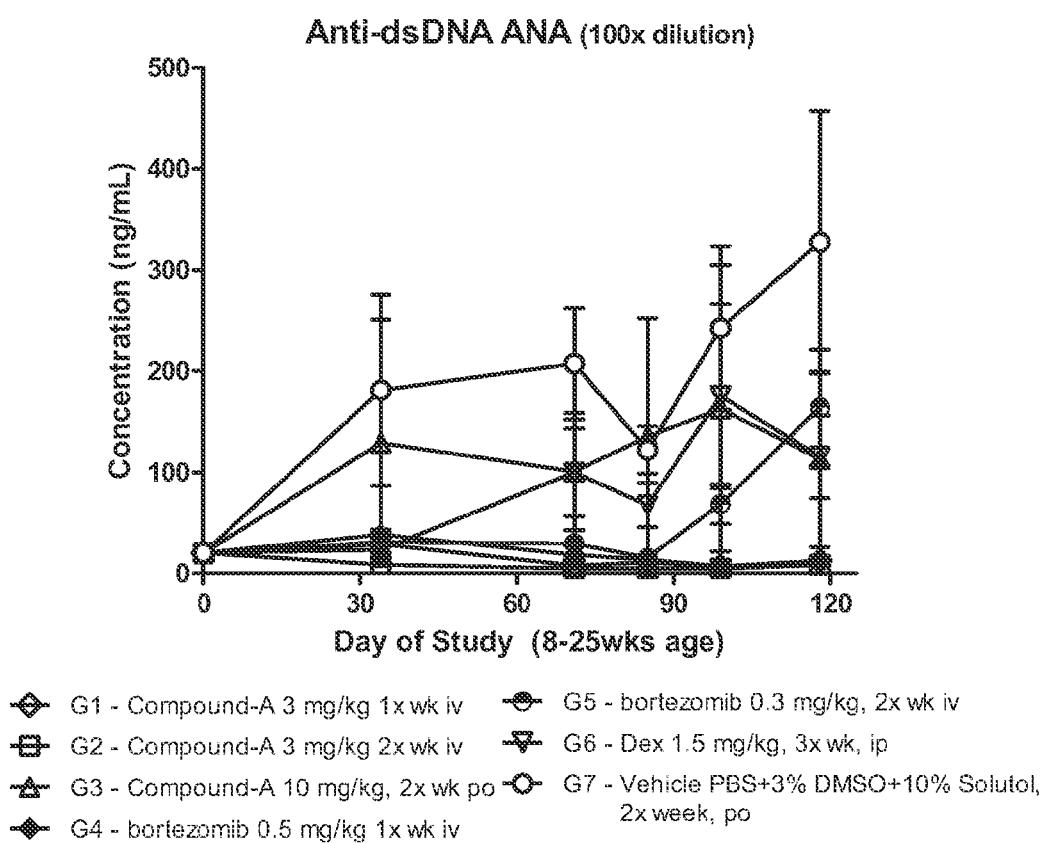
FIG. 13 depicts anti-dsDNA antinuclear antibody concentrations in MRL/lpr mice over time. Treated MRL/lpr mouse serum samples were analyzed for the presence of anti-dsDNA IgG circulating ANAs via ELISA assay (see Materials and Methods). Graph shows Mean±SEM of anti-dsDNA ANA concentration in ng/mL, 100-fold dilution from original stock.

MRL/lpr mice treated with COMPOUND A exhibited reduced levels of anti-chromatin IgG as compared to vehicle (89%, 98%, and 79% for Groups 1-3, respectively) (see FIG. 11 and Tables 11 and 20; p<0.001). Only the weekly bortezomib dose reduced anti-chromatin IgG levels as compared to vehicle (64% decrease) (see FIG. 11 and Table 11; p<0.001 and Table 20). Similar responses were observed for anti-Smith Ag IgG ANA levels (97%, 100%, 86%, and 74% decrease for Groups 1-4 compared to vehicle-treated animal at EOS) (see FIG. 12 and Tables 12 and 20). The iv doses of both COMPOUND A and bortezomib reduced anti-dsDNA IgG ANA as compared to vehicle (80%, 84%, 82%, and 58% decreases for Groups 1, 2, 4 and 5, respectively) (see FIG. 13 and Tables 13 and 20).

TABLE 9

Statistics for Group Comparisons: Frequency of Anti-smith Antigen and Anti-dsDNA Antibody Secreting Cells in the Spleens of Treated MRL/lpr Mice

| Group | Readout | G4 Bortezomib, 0.5 mg/kg 1× wk iv | G5 Bortezomib 0.3 mg/kg, 2× wk iv | G6 Dexamethasone 1.5 mg/kg, 3× wk ip | G7 Vehicle, 2× wk po |
|---|---|---|---|---|---|
| G1: COMPOUND A, 3 mg/kg 1× wk iv - | SMITH Ag | p < 0.05 | p < 0.01 | p < 0.05 | p < 0.01 |
|  | dsDNA | NS | p < 0.01 | p < 0.05 | p < 0.05 |
| G2: COMPOUND A, 3 mg/kg 2× wk iv - | SMITH Ag | p < 0.01 | p < 0.01 | p < 0.05 | p < 0.01 |
|  | dsDNA | NS | p < 0.01 | p < 0.05 | p < 0.05 |
| G3: COMPOUND A, 10 mg/kg 2× wk po - | SMITH Ag | NS | p < 0.01 | p < 0.05 | p < 0.01 |
|  | dsDNA | NS | p < 0.01 | p < 0.05 | p < 0.05 |
| G6: Dexamethasone, 1.5 mg/kg 3× wk ip - | SMITH Ag | p < 0.05 | NS | NA | NS |
|  | dsDNA | NS | NS | NA | NS |
| G7: Vehicle, 2× wk po - | SMITH Ag | p < 0.05 | NS | NS | NA |
|  | dsDNA | NS | NS | NS | NA |

Statistics for comparisons included a two-tailed Mann-Whitney t-test.
Single outlier value greater than 2.5 times the standard deviation in Group-7, vehicle, was excluded from the analysis for both dsDNA and Smith antigen.

TABLE 10

Statistics for Group Comparisons: Frequency of Anti-Chromatin Antibody Secreting Cells in the Spleens of Treated MRL/lpr Mic

| Group | G4 Bortezomib, 0.5 mg/kg 1× wk iv | G5 Bortezomib 0.3 mg/kg, 2× wk iv | G6 Dexamethasone 1.5 mg/kg, 3× wk ip | G7 Vehicle, 2× wk po |
|---|---|---|---|---|
| G1: COMPOUND A, 3 mg/kg 1× wk iv | NS | P < 0.01 | P < 0.05 | P < 0.01 |
| G2: COMPOUND A, 3 mg/kg 2× wk iv | NS | P < 0.01 | P < 0.01 | P < 0.01 |
| G3: COMPOUND A, 10 mg/kg 2× wk po | NS | P < 0.05 | P < 0.05 | P < 0.01 |
| G6: Dexamethasone, 1.5 mg/kg 3× wk ip | NS | NS | NA | NS |
| G7: Vehicle, 2× wk po | P < 0.05 | NS | NS | NA |

Statistics for comparisons included two-tailed Mann-Whitney t-test.

TABLE 11

Statistics for Group Comparisons: Anti-chromatin Anti-nuclear Antibody
Concentrations in Treated MRL/lpr Mice Over Time

| Group | G4<br>Bortezomib, 0.5<br>mg/kg 1× wk iv | G5<br>Bortezomib 0.3<br>mg/kg, 2× wk iv | G6<br>Dexamethasone 1.5<br>mg/kg, 3× wk ip | G7<br>Vehicle,<br>2× wk po |
|---|---|---|---|---|
| G1: COMPOUND A, 3 mg/kg 1× wk iv | NS | NS | NS | p < 0.001 |
| G2: COMPOUND A, 3 mg/kg 2× wk iv | NS | NS | NS | p < 0.001 |
| G3: COMPOUND A, 10 mg/kg 2× wk po | NS | NS | NS | p < 0.001 |
| G6: Dexamethasone, 1.5 mg/kg 3× wk ip | NS | NS | NA | NS |
| G7: Vehicle, 2× wk po | p < 0.001 | NS | NS | NA |

Statistics performed was 1-way ANOVA.

TABLE 12

Statistics for Group Comparisons: Anti-Smith Antigen Antinuclear
Concentrations in Treated MRL/lpr Mice Over Time

| Group | G4<br>Bortezomib, 0.5<br>mg/kg 1× wk iv | G5<br>Bortezomib 0.3<br>mg/kg, 2× wk iv | G6<br>Dexamethasone 1.5<br>mg/kg, 3× wk ip | G7<br>Vehicle,<br>2× wk po |
|---|---|---|---|---|
| G1: COMPOUND A, 3 mg/kg 1× wk iv | NS | NS | NS | p < 0.001 |
| G2: COMPOUND A, 3 mg/kg 2× wk iv | NS | NS | NS | p < 0.001 |
| G3: COMPOUND A, 10 mg/kg 2× wk po | NS | NS | NS | p < 0.001 |
| G6: Dexamethasone, 1.5 mg/kg 3× wk ip | NS | NS | NA | NS |
| G7: Vehicle, 2× wk po | p < 0.001 | NS | NS | NA |

Statistics performed was 1-way ANOVA.

TABLE 13

Statistics for Group Comparisons: Anti-dsDNA Antinuclear Antibody
Concentrations in Treated MRL/lpr Mice Over Time

| Group | G4<br>Bortezomib, 0.5<br>mg/kg 1× wk iv | G5<br>Bortezomib 0.3<br>mg/kg, 2× wk iv | G6<br>Dexamethasone 1.5<br>mg/kg, 3× wk ip | G7<br>Vehicle,<br>2× wk po |
|---|---|---|---|---|
| G1: COMPOUND A, 3 mg/kg 1× wk iv | NS | NS | NS | p < 0.001 |
| G2: COMPOUND A, 3 mg/kg 2× wk iv | NS | NS | NS | p < 0.001 |
| G3: COMPOUND A, 10 mg/kg 2× wk po | NS | NS | NS | NS |
| G6: Dexamethasone, 1.5 mg/kg 3× wk ip | NS | NS | NA | NS |
| G7: Vehicle, 2× wk po | p < 0.001 | p < 0.001 | NS | NA |

Statistics performed was 1-way ANOVA.

This data is important because the presence of anti-dsDNA antibodies is associated with a poor prognosis of lupus and is strongly associated with the development of nephritis, which may be fatal (Egner 2000; Kiss, Lakos et al. 2009). COMPOUND A was superior to bortezomib in that treatment with COMPOUND A significantly reduced both anti-chromatin IgG and anti-Smith Ag IgG ANA levels, but twice weekly treatment with bortezomib failed to significantly reduce serum levels of either ANA.

Plasma Cells

Figure 14:
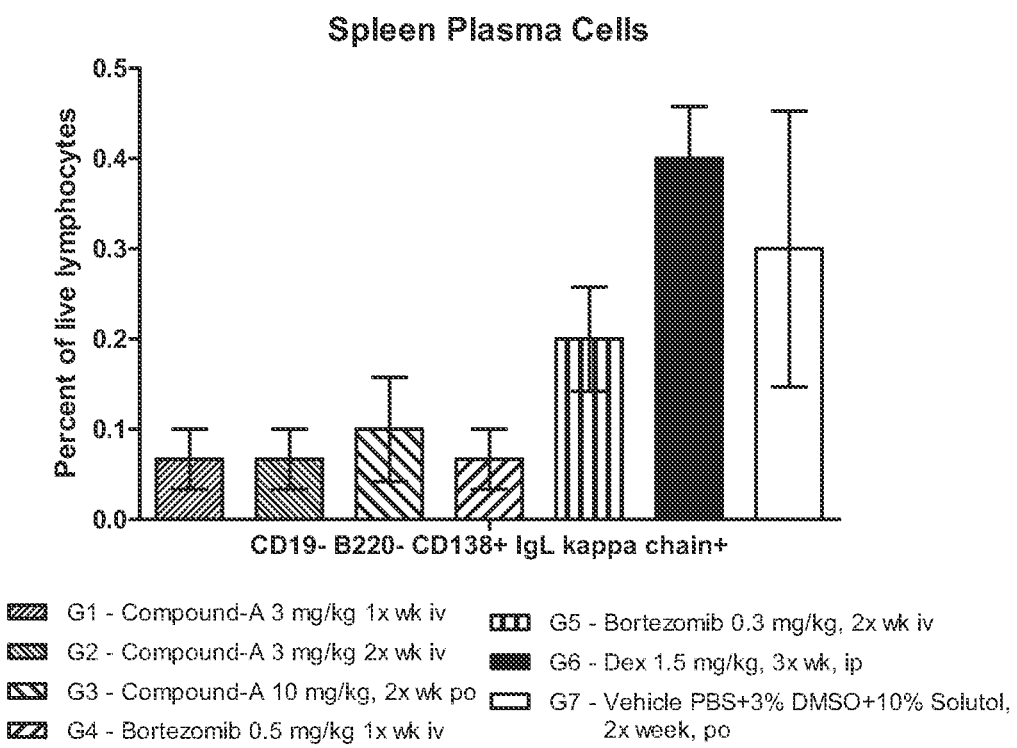
FIG. 14 depicts the proportion of CD138hi spleen plasma cells from MRL/lpr mice. MRL/lpr spleens were removed and processed for leukocytes (RBC lysis). Total spleen leukocytes were stained with anti-CD19-FITC, anti-intracellular IgL kappa light chain-PE and anti-CD138-APC for plasma cell immunophenotype. Plasma cell stains were paired with appropriate isotype controls. Cells were ran on an Accuri C6 sampler flow cytometer and 200,000 events collected and analyzed for $SSC^{mid}$, $FSC^{mid}$ (live size gate), CD19-negative cells that expressed CD138 and were positive for intracellular IgL kappa light chain. Plasma cell frequencies are shown as a percent of live size gated lymphocytes, Mean±SEM shown in graph.

MRL/lpr mice treated with COMPOUND A exhibited decreased spleen plasma cells as compared to vehicle (defined by CD19-CD138+ intracellular IgL kappa light chain+ cells) (67% decreases for Groups 1-3; p<0.05) (see FIG. 14 and Tables 14 and 20).

Similar results were obtained for bortezomib (66% decrease for Group 4 and 33% decrease for Group 5). Treatment with COMPOUND A provided a significant improvement in total spleen plasma cells as compared to dexamethasone, similar to weekly treatment with bortezomib (p<0.05).

TABLE 14

Statistics for Group Comparisons: Proportion of CD138$^{hi}$ Spleen Plasma Cells from Treated MRL/lpr Mice

| Group | G4<br>Bortezomib, 0.5<br>mg/kg 1× wk iv | G5<br>Bortezomib 0.3<br>mg/kg, 2× wk iv | G6<br>Dexamethasone 1.5<br>mg/kg, 3× wk ip | G7<br>Vehicle,<br>2× wk po |
|---|---|---|---|---|
| G1: COMPOUND A, 3 mg/kg 1× wk iv | NS | NS | p < 0.05 | NS |
| G2: COMPOUND A, 3 mg/kg 2× wk iv | NS | NS | p < 0.05 | NS |
| G3: COMPOUND A, 10 mg/kg 2× wk po | NS | NS | p < 0.05 | NS |
| G6: Dexamethasone, 1.5 mg/kg 3× wk ip | p < 0.05 | NS | NA | NS |
| G7: Vehicle, 2× wk po | NS | NS | NS | NA |

A one-tailed Mann-Whitney t-test was used as the statistical test.

This data is important because plasma cells are responsible for the generation of autoantibodies, and long-lived plasma cells are thought to be one of the root propagators of continued lupus pathogenesis in humans (Espeli, Bokers et al. 2011; Neubert, Meister et al. 2008). Long-lived plasma cells (LL-PCs) primarily populate the bone marrow (BM), but can also be found in the spleen at sites of inflammation, and are known to be resistant to cyclophosphamide, one of the few accepted therapies for lupus nephritis (Chevrier, Genton et al. 2009). COMPOUND A was superior to bortezomib in that treatment with COMPOUND A significantly reduced spleen plasma cells as compared to dexamethasone, but treatment with twice weekly bortezomib did not.

Proteinuria and Leukouria

Figure 15:
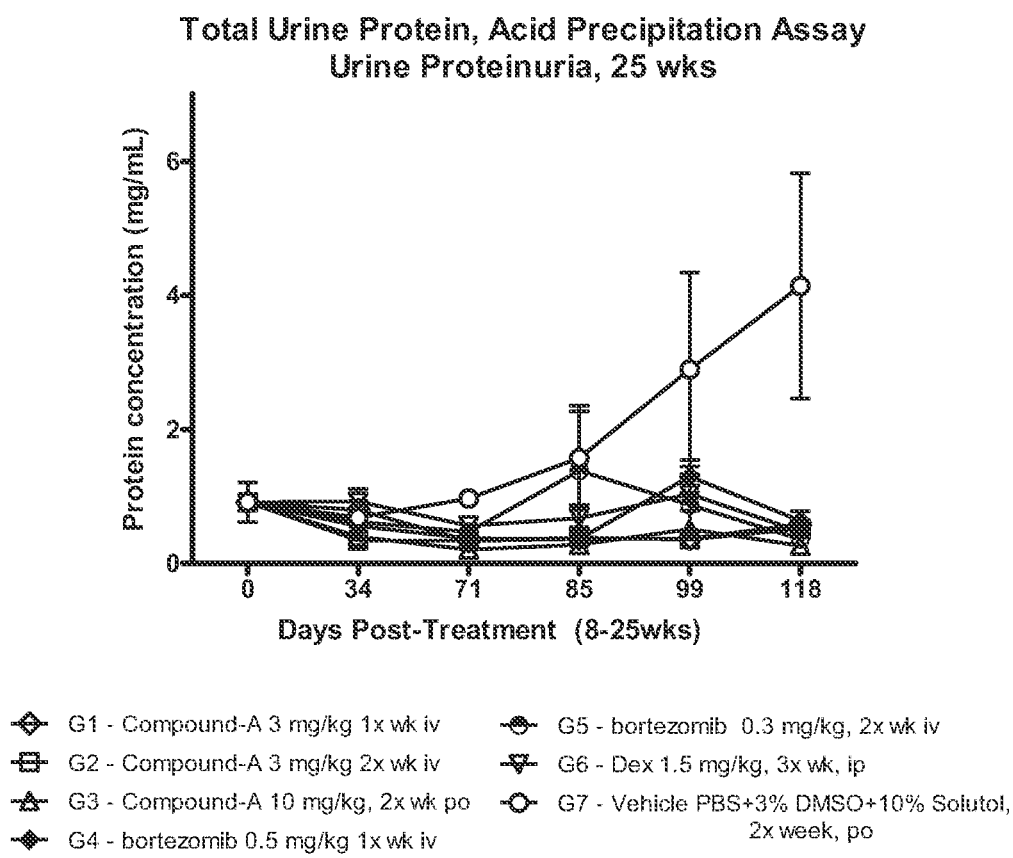
FIG. 15 depicts total urine protein (proteinuria) over time in MRL/lpr mice. Urine collected from treated MRL/lpr mice was analyzed for total protein content using a rat urinalysis kit. Graph shows Mean±SEM of protein concentration in mg/mL.
Figure 16:
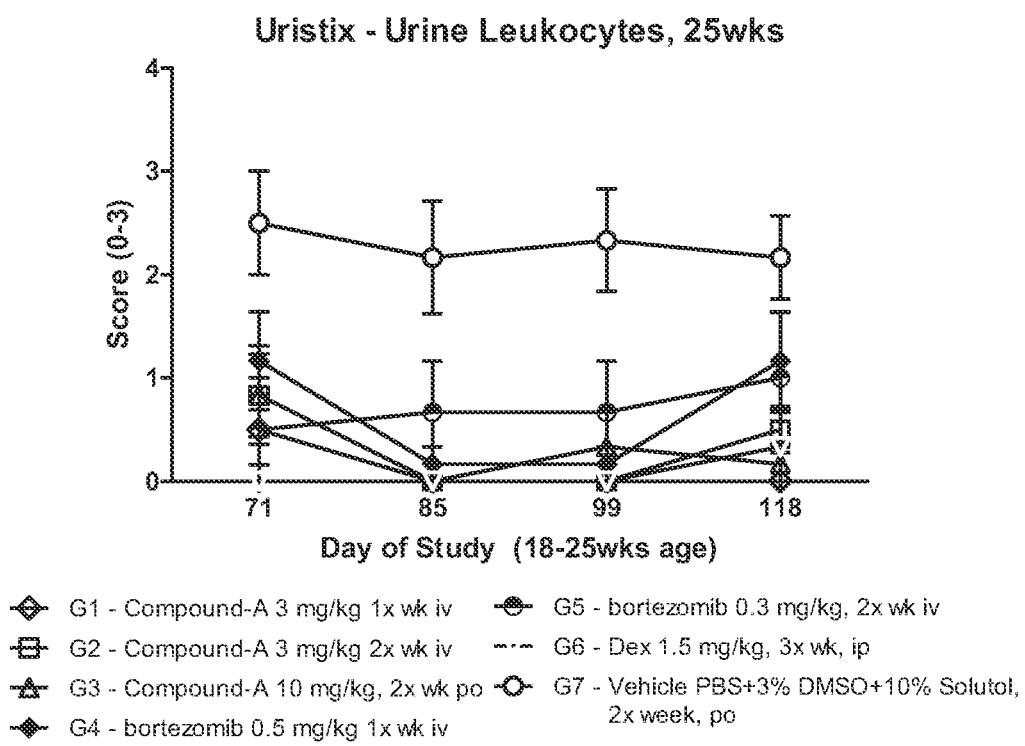
FIG. 16 depicts the presence of urine leukocytes (leukoria) in MRL/lpr mice. Urine from treated MRL/lpr mice was tested using Uristix assays for the presence of leukocytes or leukoria. Graph shows score given to each strip according to the manufacturer's instructions for the last 4 time points for the study. Graphed result is Mean±SEM.

MRL/lpr mice treated with COMPOUND A exhibited significantly reduced total urine protein over the course of the study for all three treatment groups relative to vehicle (60%, 70%, and 71% for Groups 1-3, respectively; p<0.01) (FIG. 15 and Tables 15 and 20). However, only the MRL/lpr mice treated weekly with bortezomib exhibited significantly reduced proteinuria (55% decrease; p<0.05) (FIG. 15 and Tables 15 and 20). Both COMPOUND A and bortezomib treatment reduced leukouria levels below that of vehicle (69-96% decrease for Groups 1-5; p<0.001) (FIG. 16 and Tables 16 and 20).

TABLE 15

Statistics for Group Comparisons: Total Urine Protein (Proteinuria) Over Time in Treated MRL/lpr Mice

| Group | G4<br>Bortezomib, 0.5<br>mg/kg 1× wk iv | G5<br>Bortezomib 0.3<br>mg/kg, 2× wk iv | G6<br>Dexamethasone 1.5<br>mg/kg, 3× wk ip | G7<br>Vehicle,<br>2× wk po |
|---|---|---|---|---|
| G1: COMPOUND A, 3 mg/kg 1× wk iv | NS | NS | NS | p < 0.01 |
| G2: COMPOUND A, 3 mg/kg 2× wk iv | NS | NS | NS | p < 0.01 |
| G3: COMPOUND A, 10 mg/kg 2× wk po | NS | NS | NS | p < 0.01 |
| G6: Dexamethasone, 1.5 mg/kg 3× wk ip | NS | NS | NA | NS |
| G7: Vehicle, 2× wk po | p < 0.05 | NS | NS | NA |

Statistical test used was 1 way ANOVA.

TABLE 16

Statistics for Group Comparisons: Presence of Urine Leukocytes (Leukoria) in MRL/lpr Mice

| Group | G4<br>Bortezomib, 0.5<br>mg/kg 1× wk iv | G5<br>Bortezomib 0.3<br>mg/kg, 2× wk iv | G6<br>Dexamethasone 1.5<br>mg/kg, 3× wk ip | G7<br>Vehicle,<br>2× wk po |
|---|---|---|---|---|
| G1: COMPOUND A, 3 mg/kg 1× wk iv | NS | NS | NS | p < 0.001 |
| G2: COMPOUND A, 3 mg/kg 2× wk iv | NS | NS | NS | p < 0.001 |
| G3: COMPOUND A, 10 mg/kg 2× wk po | NS | NS | NS | p < 0.001 |
| G6: Dexamethasone, 1.5 mg/kg 3× wk ip | NS | NS | NA | p < 0.001 |
| G7: Vehicle, 2× wk po | p < 0.05 | p < 0.001 | p < 0.001 | NA |

Statistics test used was 1 way ANOVA.

These results are important because increases in urine protein (proteinuria) and urine leukocytes (leukouria) are the direct result of renal damage associated with lupus nephritis. COMPOUND A was superior to bortezomib in that treatment with COMPOUND A significantly reduced proteinuria, but twice weekly treatment with bortezomib failed to provide a significant reduction in urine protein as compared to vehicle.

Histopathological Analyses

End-stage lupus nephritis was evaluated by histopathology and scored by a board certified pathologist for the assessment of total renal damage in diseased animals. MRL/lpr mice treated with COMPOUND A exhibited significantly reduced severity of various renal pathologies as compared to vehicle (1.55-1.86-fold decrease in average score) (see FIG. 17 and Tables 17 and 20). However, only the MRL/lpr mice treated weekly with bortezomib exhibited significantly reduced renal pathology severity (1.68-fold decrease in average score as compared to vehicle) (FIG. 17 and Tables 17 and 20). Importantly, all 3 COMPOUND A treatment groups exhibited reduced renal interstitial infiltration as compared to vehicle (up to 61% reduction), whereas the maximum reduction achieved by bortezomib was 47% (see Table 20).

These results are important because they show that treatment of MRL/lpr mice with COMPOUND A can slow and/or prevent the development of lupus nephritis in lupus-prone mice. COMPOUND A was superior to bortezomib in that treatment with COMPOUND A significantly reduced renal damage in MRL/lpr mice, but twice weekly treatment with bortezomib failed to provide a significant reduction.

Pharmacodynamics

Figure 18:
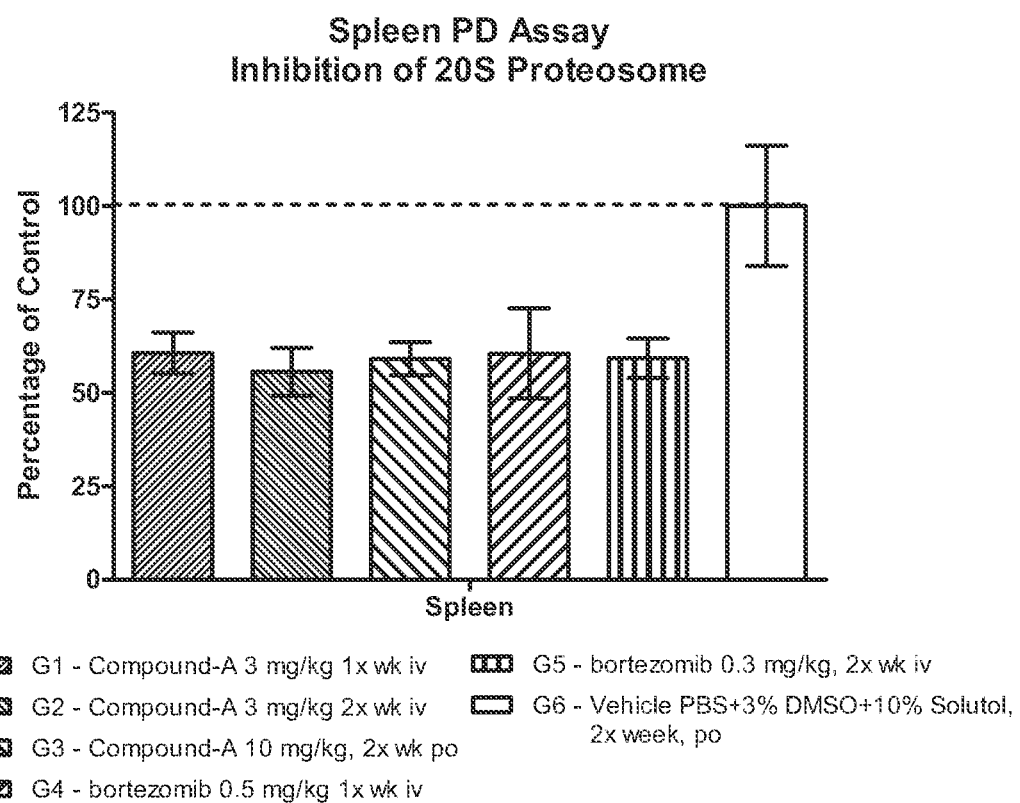
FIG. 18 depicts the activity of the 20S proteasome in spleen of MRL/lpr mice. Spleens from treated MRL/lpr mice were lysed and analyzed using a functional ex vivo test for the 20S proteasome.
Figure 19:
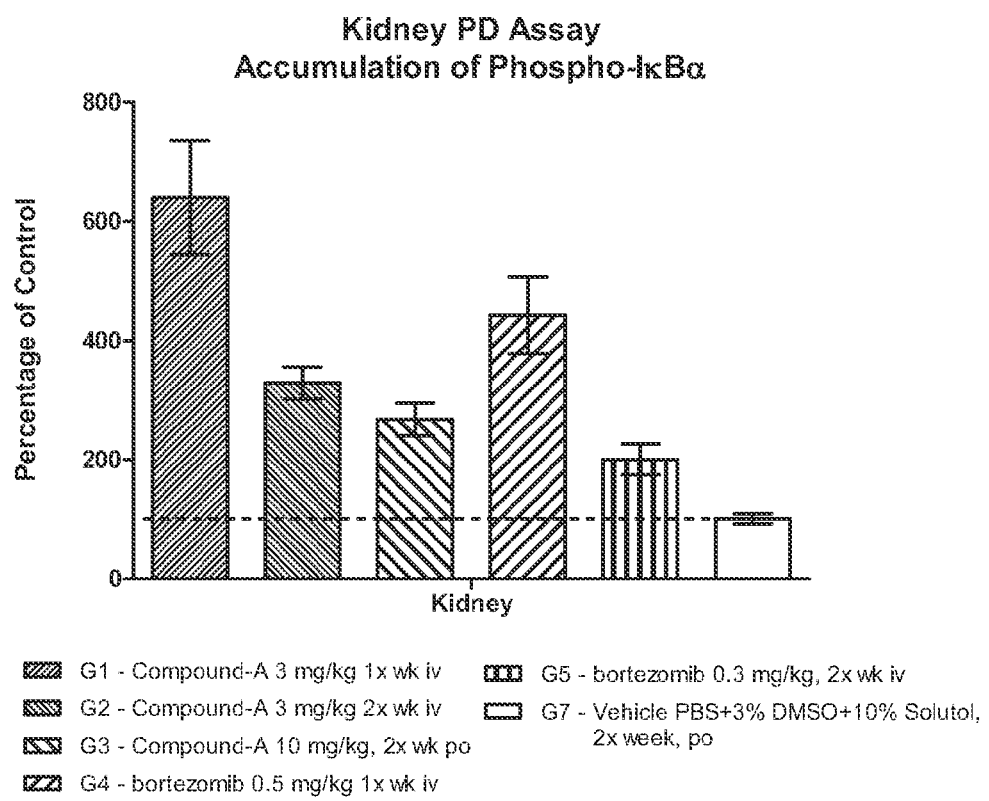
FIG. 19 depicts phospho-IκBα cellular accumulation 3 hours post drug treatment in kidney of MRL/lpr mice. Kidneys were lysed and analyzed using a commercial ELISA kit that measures the accumulation of cellular IκBα as a function of proteasome activity.

Both the 20S proteasome assay and an IκBα accumulation ELISA were used to measure the pharmacodynamic activity of COMPOUND A in the spleen and kidneys of treated mice. MRL/lpr mice treated with COMPOUND A exhibited decreased function of the 20S proteasome in the spleen as compared to vehicle (40%, 45% and 41% decreases for Groups 1-3, respectively; $p<0.01$) (see FIG. 18 and Tables 18 and 20). Similar findings were observed for bortezomib treatment groups (40% and 41% decreases relative to vehicle treatment, respectively, for Groups 4 and 5). For kidney, where active and often fatal disease is precipitated, the proteasome inhibition was of greater magnitude as measured by an IκBα accumulation assay: both COMPOUND A and bortezomib treatment led to accumulation of cytoplasmic IκBα 3-6 fold over that of the vehicle treatment group (266-537% increases over vehicle; $p<0.001$) (see FIG. 19 and Tables 19 and 20).

TABLE 18

Statistics for Group Comparisons: Activity of the 20S Proteasome in Spleen of MRL/lpr Mice

| Group | G4 Bortezomib, 0.5 mg/kg 1× wk iv | G5 Bortezomib 0.3 mg/kg, 2× wk iv | G7 Vehicle, 2× wk po |
|---|---|---|---|
| G1: COMPOUND A, 3 mg/kg 1× wk iv | NS | NS | p < 0.01 |

TABLE 17

Statistics for Group Comparisons: Renal Histopathology Results from 25 Week Old, Treated MRL/lpr Mice

| | Pathology | G4-Bortezomib 0.5 mg/kg 1× wk iv | G5-Bortezomib 0.3 mg/kg 2× wk iv | G6-Dexamethasone 1.5 mg/kg 3× wk ip | G7-Vehicle 2× wk po |
|---|---|---|---|---|---|
| G1-COMPOUND A, 3 mg/kg 1× wk iv | Glomerular cellularity | NS | NS | NS | p < 0.001 |
| | Gomerular necrosis | NS | NS | NS | p < 0.01 |
| | Glomerulo-sclerosis | NS | NS | NS | p < 0.01 |
| | Interstitial infiltration | NS | NS | NS | p < 0.001 |
| | Tubular atrophy | NS | NS | NS | NS |
| | Interstitial fibrosis | NS | NS | NS | NS |
| | Vasculitis | NS | NS | NS | p < 0.01 |
| G2-COMPOUND A, 3 mg/kg 2× wk iv | Glomerular cellularity | NS | NS | NS | p < 0.001 |
| | Glomerular necrosis | NS | NS | NS | p < 0.001 |
| | Glomerulo-sclerosis | NS | p < 0.05 | NS | p < 0.001 |
| | Interstitial infiltration | NS | NS | NS | p < 0.001 |
| | Tubular atrophy | NS | NS | NS | p < 0.001 |
| | Interstitial fibrosis | NS | NS | NS | p < 0.01 |
| | Vasculitis | NS | NS | NS | p < 0.001 |
| G3-COMPOUND A, 10 mg/kg 2× wk po | Glomerular cellularity | NS | NS | NS | p < 0.001 |
| | Glomerular necrosis | NS | NS | NS | p < 0.01 |
| | Glomerulo-sclerosis | NS | NS | NS | p < 0.01 |
| | Interstitial infiltration | NS | NS | NS | p < 0.001 |
| | Tubular atrophy | NS | NS | NS | p < 0.01 |
| | Interstitial fibrosis | NS | NS | NS | NS |
| | Vasculitis | NS | NS | NS | p < 0.01 |
| G6-Dexamethasone, 1.5 mg/kg 3× wk ip | Glomerular cellularity | NS | NS | NS | NS |
| | Glomerular necrosis | NS | NS | NS | NS |
| | Glomerulo-sclerosis | NS | NS | NA | NS |
| | Interstitial infiltration | NS | NS | NS | NS |
| | Tubular atrophy | NS | NS | NS | NS |
| | Interstitial fibrosis | NS | NS | NS | NS |
| | Vasculitis | NS | NS | NS | NS |
| G7-Vehicle, 2× wk po | Glomerular cellularity | p < 0.01 | NS | NS | NS |
| | Glomerular necrosis | P < 0.05 | NS | NS | NS |
| | Glomerulo-sclerosis | p < 0.001 | NS | NS | NA |
| | Interstitial infiltration | p < 0.001 | p < 0.001 | p < 0.001 | NS |
| | Tubular atrophy | P < 0.01 | NS | NS | NS |
| | Interstitial fibrosis | P < 0.01 | NS | NS | NS |
| | Vasculitis | P < 0.001 | NS | NS | NS |

TABLE 18-continued

Statistics for Group Comparisons: Activity of the 20S
Proteasome in Spleen of MRL/lpr Mice

| Group | G4<br>Bortezomib, 0.5<br>mg/kg 1× wk iv | G5<br>Bortezomib 0.3<br>mg/kg, 2× wk iv | G7<br>Vehicle,<br>2× wk po |
|---|---|---|---|
| G2: COMPOUND A,<br>3 mg/kg 2× wk iv | NS | NS | p < 0.01 |
| G3: COMPOUND A,<br>10 mg/kg 2× wk po | NS | NS | p < 0.01 |
| G7: Vehicle, 2× wk po | p < 0.05 | p < 0.01 | NA |

Statistical test used was a two-tailed Mann-Whitney t-test.

TABLE 19

Phospho-IκBα Cellular Accumulation 3 Hours
Post Drug Treatment in Kidney of MRL/lpr Mice

| Group | G4<br>Bortezomib, 0.5<br>mg/kg 1× wk iv | G5<br>Bortezomib 0.3<br>mg/kg, 2× wk iv | G7<br>Vehicle,<br>2× wk po |
|---|---|---|---|
| G1: COMPOUND A,<br>3 mg/kg 1× wk iv | NS | p < 0.01 | P < 0.01 |
| G2: COMPOUND A,<br>3 mg/kg 2× wk iv | NS | p < 0.01 | P < 0.01 |
| G3: COMPOUND A,<br>10 mg/kg 2× wk po | NS | NS | P < 0.01 |
| G7: Vehicle, 2× wk po | p < 0.01 | p < 0.05 | NA |

Statistical test used was a two-tailed Mann-Whitney t-test.

TABLE 20

MRL/lpr Summary Percent Change vs Vehicle for Multiple Parameters

| Parameter | G1 | G2 | G3 | G4 | G5 | G6 | G7 |
|---|---|---|---|---|---|---|---|
| AUC body mass | −15 | −13 | −4 | −17 | −11 | −3 | n/a |
| EOS survival[a] | 87 | 100 | 100 | 90 | 73 | 83 | 92 |
| AUC lymphomegaly | 71 | 34 | 9 | 13 | 21 | 22 | n/a |
| EOS spleen mass | −67 | −74 | −56 | −68 | −44 | −71 | n/a |
| Cytokine AUC serum IL-12 | −48 | −72 | −62 | −54 | −54 | −74 | n/a |
| Cytokine AUC serum IL-1β | −56 | −61 | −58 | −46 | −51 | −44 | n/a |
| Cytokine AUC serum TNFα | −62 | −79 | −71 | −64 | −71 | −87 | n/a |
| ASC EOS Smith Ag | −97 | −110 | −86 | −74 | +73 | +40 | n/a |
| ASC EOS dsDNA | −80 | −84 | −82 | −58 | +219 | +129 | n/a |
| ASC EOS chromatin | −89 | −98 | −79 | −64 | +5 | −22 | n/a |
| ANA AUC chromatin | −94 | −94 | −91 | −82 | −58 | −47 | n/a |
| ANA AUC Smith Ag | −96 | −96 | −94 | −84 | −58 | −45 | n/a |
| ANA AUC dsDNA | −91 | −95 | −37 | −88 | −76 | −59 | n/a |
| EOS plasma cells | −67 | −67 | −67 | −67 | −33 | +25 | n/a |
| Urine AUC proteinuria | −60 | −70 | −71 | −55 | −50 | −46 | n/a |
| Urine AUC leukocytes | −96 | −94 | −94 | −78 | −70 | −100 | n/a |
| EOS glomerular cellularity | −41 | −36 | −33 | −31 | −15 | −15 | n/a |
| EOS glomerular necrosis | −38 | −47 | −31 | −28 | −25 | −25 | n/a |
| EOS glomerulosclerosis | −39 | −45 | −33 | −42 | −18 | −27 | n/a |
| EOS interstitial infiltration | −42 | −61 | −50 | −47 | −39 | −50 | n/a |
| Kidney EOS tubular atrophy | −35 | −46 | −42 | −50 | −27 | −23 | n/a |
| Kidney EOS interstitial fibrosis | −31 | −42 | −27 | −46 | −27 | −27 | n/a |
| EOS vasculitis | −33 | −45 | −43 | −42 | −21 | −18 | n/a |
| PD EOS 20S proteasome | −40 | −45 | −41 | −40 | −41 | n/a | n/a |
| PD EOS IκBα accumulation | +537 | +227 | +166 | +340 | +99 | n/a | n/a |

Notes:
[a]Survival data shows true EOS mouse percentages from starting population for each group; values in bold are significant (p ≤ 0.05) relative to vehicle treatment.
ANA = antinuclear antibodies;
AUC = area under the curve;
EOS = end of study;
Lymphomegaly values represent the percent of non enlarged lymph nodes relative to the vehicle-treatment group.
G1 = COMPOUND A 3 mg/kg iv, 1× wk;
G2 = COMPOUND A 3 mg/kg iv, 2× wk;
G3 = COMPOUND A 10 mg/kg po, 2× wk;
G4 = bortezomib 0.5 mg/kg iv, 1× wk;
G5 = bortezomib 0.3 mg/kg iv, 2× wk;
G6 = dexamethasone 1.5 mg/kg ip, 3× wk;
G7 = vehicle po, 2× wk Summary Treatment of lupus-prone MRL/lpr mice with COMPOUND A resulted in a reduction of several lupus-associated immune-parameters compared to both dexamethasone and bortezomib. COMPOUND A proved superior to bortezomib in many respects. For example, all three dosing regimens of COMPOUND A resulted in a significant reduction in the incidence and severity of renal pathologies as compared to the bortezomib 0.3 mg/kg 2× week group, with these reductions directly correlated with reduced proteinuria and SLE-related mortality in MRL/lpr mice.

Example 2

COMPOUND A Effectively Treats Lupus in NZM Mice

Protocol

Age mated female NZM or NZW/LacJ mice were matured for the study of lupus nephritis for a total of 7 months or 210 days at which time urine was collected for proteinuria detection. Mice with 0.5-1.0 mg/ml of urine protein as determined by an optical density-based total protein precipitation assay or 30-300 mg/dl of protein as determined by a stick assay were considered proteinuria positive and selected for study entry. Groups were normalized to contain a Gaussian distribution of proteinuria positive animals (i.e., ⅓ low proteinuria, ⅓ medium, ⅓ high) then randomized between groups before ear marking and taking baseline measures including body weight, urine and serum collections. A total of five mice from the total population were randomly selected for baseline kidney histology evaluation.

Figure 20:
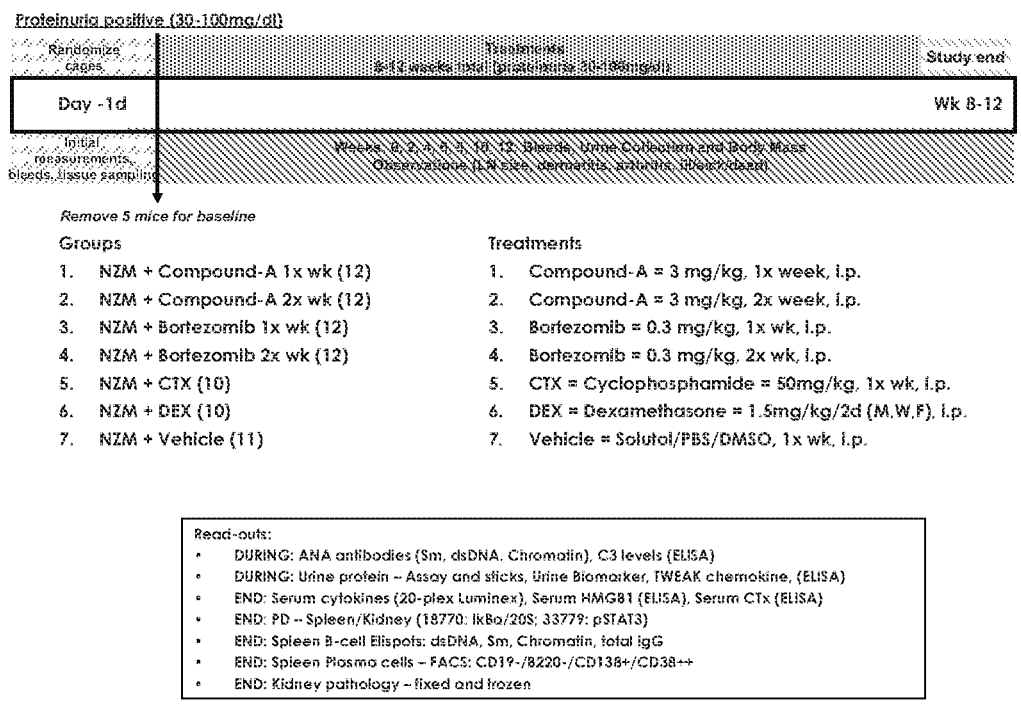
FIG. 20 depicts an overview of the experimental design for testing COMPOUND A and bortezomib treatment of progressive lupus in the NZM lupus nephritis mouse model.

Treatments and tests for each group are as described in FIG. 20. Briefly, in Group one (G1) COMPOUND A was administered at a dose of 3 mg/kg ip once per week. In group two (G2), COMPOUND A was administered at a dose of 3 mg/kg ip twice weekly. In group three (G3), bortezomib was administered at a dose of 0.3 mg/kg ip once per week. In group four (G4), bortezomib was administered at a dose of 0.3 mg/kg ip twice weekly. Groups five and six (G5 and G6) were standard of care agents cyclophosphamide (CTX) and dexamethasone. In G5, CTX was administered in saline at 50 mg/kg, once weekly, ip. Along with MMF and Azathioprine, Cyclophosphamide is a current treatment option for patients suffering from lupus nephritis as it acts as a potent immunosuppressive agent, however, due to its severe side-effects it is used only in the most severe cases. In G6, dexamethasone was administered in saline at 1.5 mg/kg, three times per week, ip. In Group seven (G7), vehicle was provided ip with Solutol as the preservative suspended in saline and 1% DMSO. COMPOUND A and bortezomib were suspended in the vehicle solution. Treatments started on day of age, 212, some mice died shortly after treatment but all animals regardless of health status were counted against the total group size from time of dosing. Bi-monthly bleeds and urine were collected and serum and urine were frozen at −80° C. until assayed. End analyses included kidney histology, splenocyte B-cell Elispots, flow cytometry for B and T cell populations, pharmacodynamic markers, serum cytokines, antibody and complement levels. All graphs shown in the relevant Figures show day-0 as being the "start of treatment" and thus represents 212 days of age. Day-98 or "end of treatment/study" represents 310 days of age for the NZM animals. All graphs show time as "day on study" with day on study starting at 212 days of age and ending at 310 days of age.

Body Weight and Survival

Figure 22:
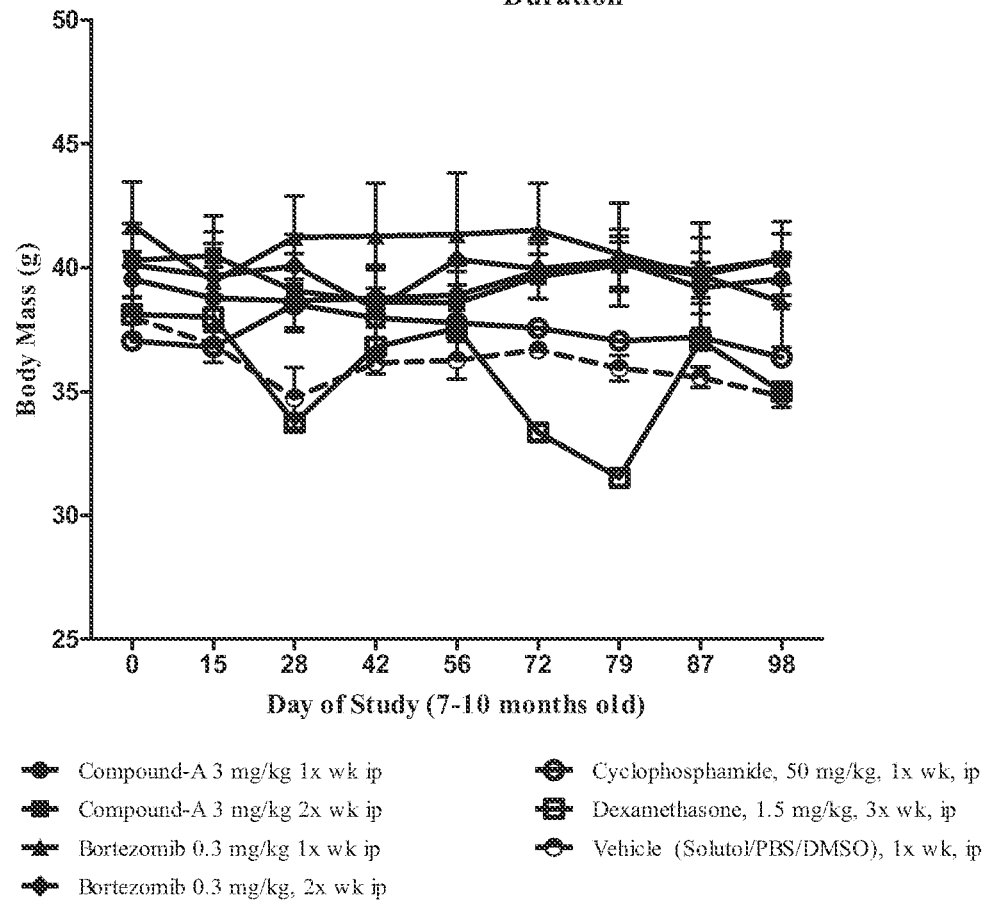
FIG. 22 depicts the body weight progression for NZM mice across treatment groups for the study duration. NZM mice were treated as outlined in the legend. Graph shows Mean±SEM body mass for each group across the duration of the study.

NZM mice treated with COMPOUND A exhibited significantly increased body weight as compared to vehicle (9% and 10% respectively; p<0.001), similar to bortezomib and standards of care (see FIG. 22 and Tables 22 and 41).

Figure 21:
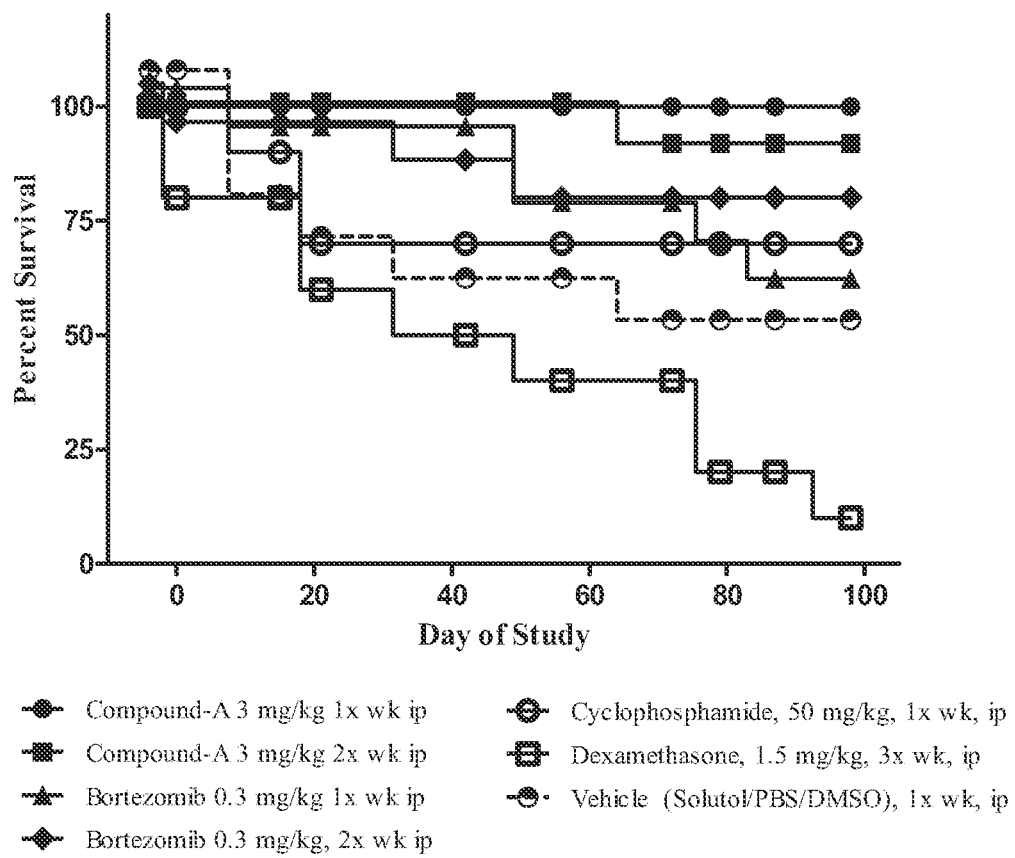
FIG. 21 depicts survival of NZM mice across treatment groups for the study duration. NZM mice were treated as outlined in the legend. Graph shows percent of live mice for each week of the study.

NZM mice treated with COMPOUND A exhibited significantly increased survival relative to vehicle (55% and 46%, respectively; p<0.001), and significantly extended survival over that of both standard of care agents (CTX and dexamethasone) and both bortezomib groups (p<0.01) (see FIG. 21 and Tables 21 and 41). At day 56, 100% of mice were still alive for both COMPOUND A treatment groups and only 75% of mice were still alive for both of the bortezomib-treatment groups. At the end of the study (day 310), only 45% of mice survived in the vehicle treatment group, whereas in the COMPOUND A treatment groups 100% of animals remained.

TABLE 21

Statistics for Group Comparisons: Survival for NZM Mice Across Treatment Groups for the Study Duration

| Group | G5-Bortezomib, 0.3 mg/kg 1× wk ip | G6-Bortezomib 0.3 mg/kg, 2× wk ip | G7-CTX 50 mg/kg 1× wk ip | G8-Dex 1.5 mg/kg, 3× wk ip | G9-Vehicle, 1× wk ip |
|---|---|---|---|---|---|
| G1 - COMPOUND A, 3 mg/kg 1× wk ip | p < 0.01 | p < 0.001 | p < 0.001 | p < 0.001 | p < 0.001 |
| G2 - COMPOUND A, 3 mg/kg 2× wk ip | p < 0.01 | p < 0.001 | p < 0.001 | p < 0.001 | p < 0.001 |
| G7 - CTX 50 mg/kg 1× wk ip | NS | NS | NA | p < 0.01 | p < 0.001 |
| G8 - Dex, 1.5 mg/kg 3× wk ip | p < 0.001 | p < 0.001 | p < 0.01 | NA | p < 0.05 |
| G9 - Vehicle, 1× wk ip | p < 0.01 | p < 0.01 | p < 0.001 | p < 0.05 | NA |

Statistics used for comparisons was a two-tailed paired student t-test;
NS = not significant (p > 0.05);
NA = not applicable

TABLE 22

Statistics for Group Comparisons: Body Weight Progression for NZM Mice Across Treatment Groups for the Study Duration

| Group | G5-Bortezomib, 0.3 mg/kg 1× wk ip | G6-Bortezomib 0.3 mg/kg, 2× wk ip | G7-CTX 50 mg/kg 1× wk ip | G8-Dex 1.5 mg/kg, 3× wk ip | G9-Vehicle, 1× wk ip |
|---|---|---|---|---|---|
| G1 - COMPOUND A, 3 mg/kg 1× wk ip | NS | NS | p < 0.05 | p < 0.001 | p < 0.001 |
| G2 - COMPOUND A, 3 mg/kg 2× wk ip | NS | NS | p < 0.01 | p < 0.001 | p < 0.001 |
| G7 - CTX 50 mg/kg 1× wk ip | p < 0.001 | p < 0.001 | NA | NS | NS |
| G8 - Dex, 1.5 mg/kg 3× wk ip | p < 0.001 | p < 0.001 | NS | NA | NS |
| G9 - Vehicle, 1× wk ip | p < 0.001 | p < 0.001 | NS | NS | NS |

Statistics used for comparisons was 1-way ANOVA;
NS = not significant (p > 0.05);
NA = not applicable This data is important because it shows that COMPOUND A provided a significant survival benefit over bortezomib in this mouse model of lupus nephritis.

Splenomegaly

Figure 23:
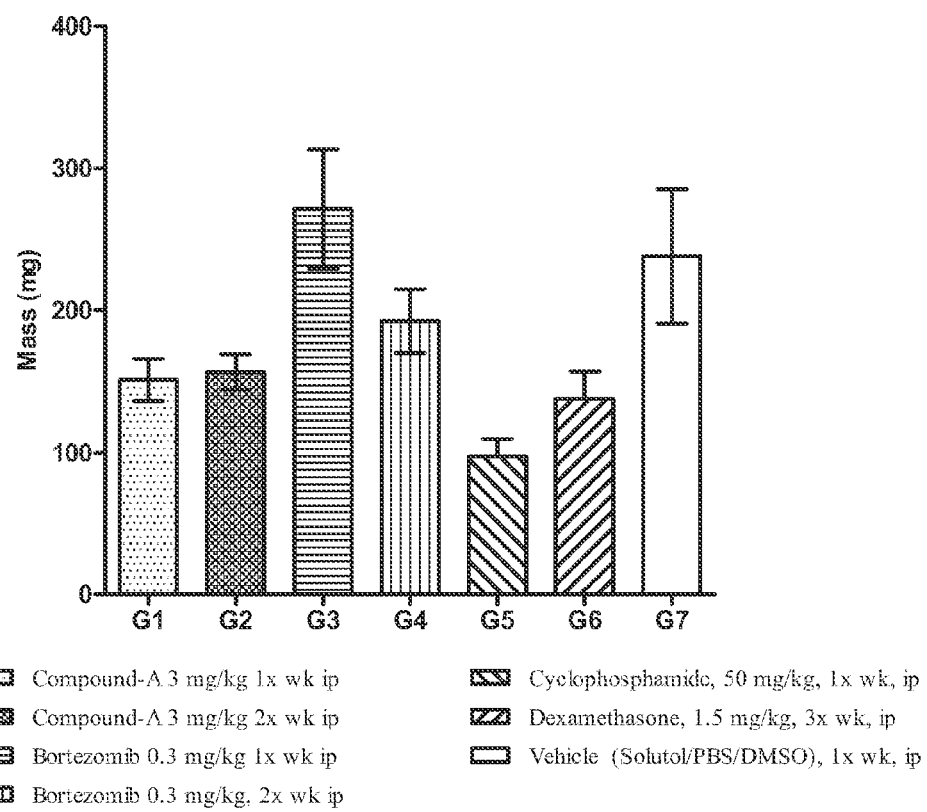
FIG. 23 depicts splenomegaly for NZM mice across treatment groups for the study duration. NZM mice were treated as outlined in the legend. The spleen weights for all mice that survived until the end of the study are graphed. Values represent the mean±SEM spleen weight at 25 weeks of age.

NZM mice treated with COMPOUND A exhibited decreased splenomegaly as compared to vehicle control (37% and 34% decrease at EOS) (see FIG. 23 and Tables 23 and 41). Treatment with COMPOUND A or CTX also reduced spleen mass significantly compared to once-a-week bortezomib (p<0.05) (see FIG. 23 and Tables 23 and 41). Changes in spleen mass were compared against the vehicle treatment group spleen mass and not normalized for body mass at EOS, day-98, as body mass for all groups were not significantly different at EOS, day-98, as analyzed using a 2-way ANOVA test (p>0.05).

TABLE 23

Statistics for Group Comparisons: Splenomegaly for NZM Mice Across Treatment Groups for the Study Duration

| Group | G3-Bortezomib, 0.3 mg/kg 1× wk ip | G4-Bortezomib 0.3 mg/kg, 2× wk ip | G5-CTX 50 mg/kg 1× wk ip | G6-Dex 1.5 mg/kg, 3× wk ip | G7-Vehicle, 1× wk ip |
|---|---|---|---|---|---|
| G1 - COMPOUND A, 3 mg/kg 1× wk ip | p < 0.01 | NS | p < 0.05 | NS | NS |
| G2 - COMPOUND A, 3 mg/kg 2× wk ip | p < 0.05 | NS | p < 0.01 | NS | NS |
| G5 - CTX 50 mg/kg 1× wk ip | p < 0.01 | p < 0.01 | NA | NS | p < 0.01 |
| G6 - Dex, 1.5 mg/kg 3× wk ip | p < 0.05 | NS | NS | NA | NS |
| G7 - Vehicle, 1× wk ip | NS | NS | p < 0.01 | NS | NA |

Statistics used for comparisons was a two-tailed Mann-Whitney test;
NS = not significant (p > 0.05);
NA = not applicable.

This data is important because splenomegaly (spleen swelling) is indicative of lupus disease in NZM mice. COMPOUND A was superior to bortezomib in that splenomegaly was significantly reduced in animals treated with COMPOUND A as compared to weekly bortezomib.

Proteinuria

Figure 24:
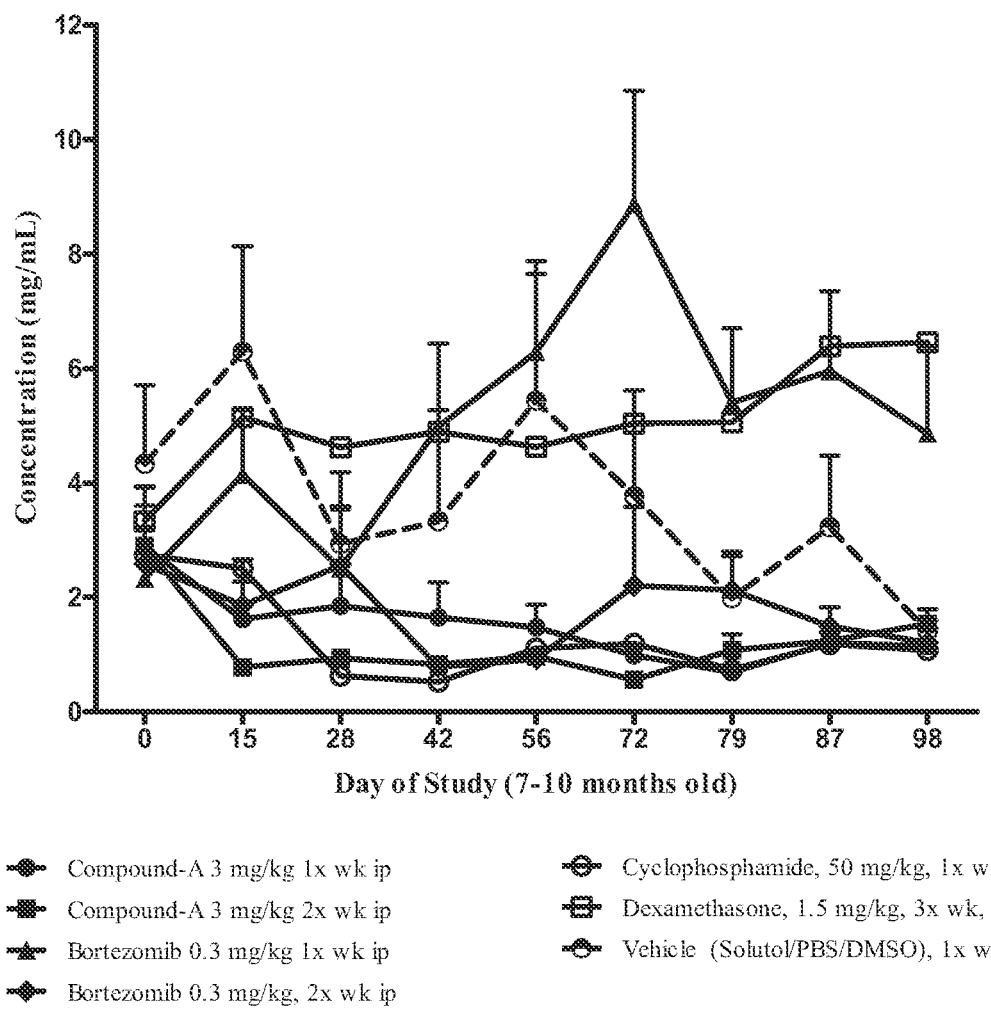
FIG. 24 depicts total urine protein (proteinuria) in NZM mice. Urine collected from NZM mice was analyzed for total protein content using a rat urinalysis kit. Graph shows Mean±SEM of protein concentration in mg/mL.

NZM mice treated with COMPOUND A exhibited reduced proteinuria as compared to once weekly bortezomib, DEX, or vehicle (61% and 72% for Groups 1&2 as compared to vehicle) (p<0.01) (see FIG. 24 and Tables 24 and 41).

These results are important because an increase in urine protein (proteinuria) is the direct result of renal damage associated with lupus nephritis. COMPOUND A was superior to bortezomib in that proteinuria was significantly reduced in animals treated with COMPOUND A as compared to weekly bortezomib.

Antinuclear Antibodies (ANAs)

Figure 25:
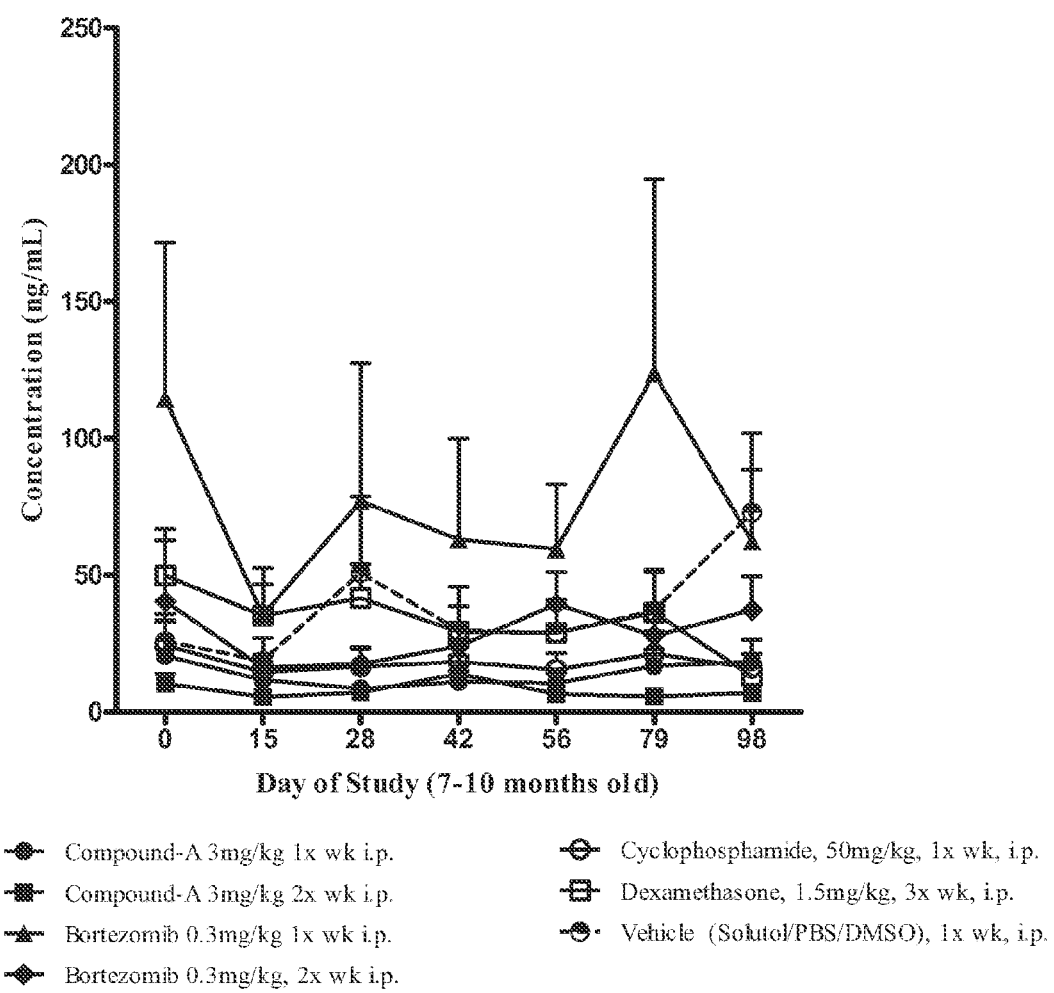
FIG. 25 depicts anti-chromatin antinuclear antibody concentrations in serum of NZM mice. NZM mouse serum samples were analyzed for the presence of anti-chromatin IgG circulating ANAs via ELISA assay. Graph shows Mean±SEM of anti-chromatin ANA concentration in ng/mL, 2000-fold dilution from original stock.

NZM mice treated weekly or twice weekly with COMPOUND A exhibited significantly decreased serum anti-chromatin Ab as compared to vehicle (63% and 79% decreases, respectively; p<0.05) (see Tables 25 and 41 and FIG. 25). These reductions in anti-chromatin Ab by COMPOUND A were greater than reductions observed for the bortezomib, Dex or CTX treatment groups, none of which was significant relative to the vehicle treatment group. NZM mice treated with COMPOUND A twice weekly exhibited decreased serum anti-chromatin Ab (79% decrease compared to vehicle) compared to twice weekly bortezomib (22% decrease compared to vehicle) (see FIG. 25 and Tables 25 and 41). NZM mice treated with COMPOUND A once or twice weekly exhibited decreased serum anti-chromatin Ab as compared to once weekly bortezomib (p<0.001) (see FIG. 25 and Tables 25 and 41). Once weekly administration of COM

TABLE 24

Statistics for Group Comparisons: Total Urine Protein (proteinuria) in Treated NZM Mice

| Group | G5-Bortezomib, 0.3 mg/kg 1× wk ip | G6-Bortezomib 0.3 mg/kg, 2× wk ip | G7-CTX 50 mg/kg 1× wk ip | G8-Dex 1.5 mg/kg, 3× wk ip | G9-Vehicle, 1× wk ip |
|---|---|---|---|---|---|
| G1 - COMPOUND A, 3 mg/kg 1× wk ip | p < 0.001 | NS | NS | p < 0.001 | p < 0.01 |
| G2 - COMPOUND A, 3 mg/kg 2× wk ip | p < 0.001 | NS | NS | p < 0.001 | p < 0.001 |
| G7 - CTX 50 mg/kg 1× wk ip | p < 0.001 | NS | NA | p < 0.001 | p < 0.01 |
| G8 - Dex, 1.5 mg/kg 3× wk ip | NS | p < 0.001 | p < 0.001 | NA | NS |
| G9 - Vehicle, 1× wk ip | NS | p < 0.05 | p < 0.001 | NS | NA |

Figure 26:
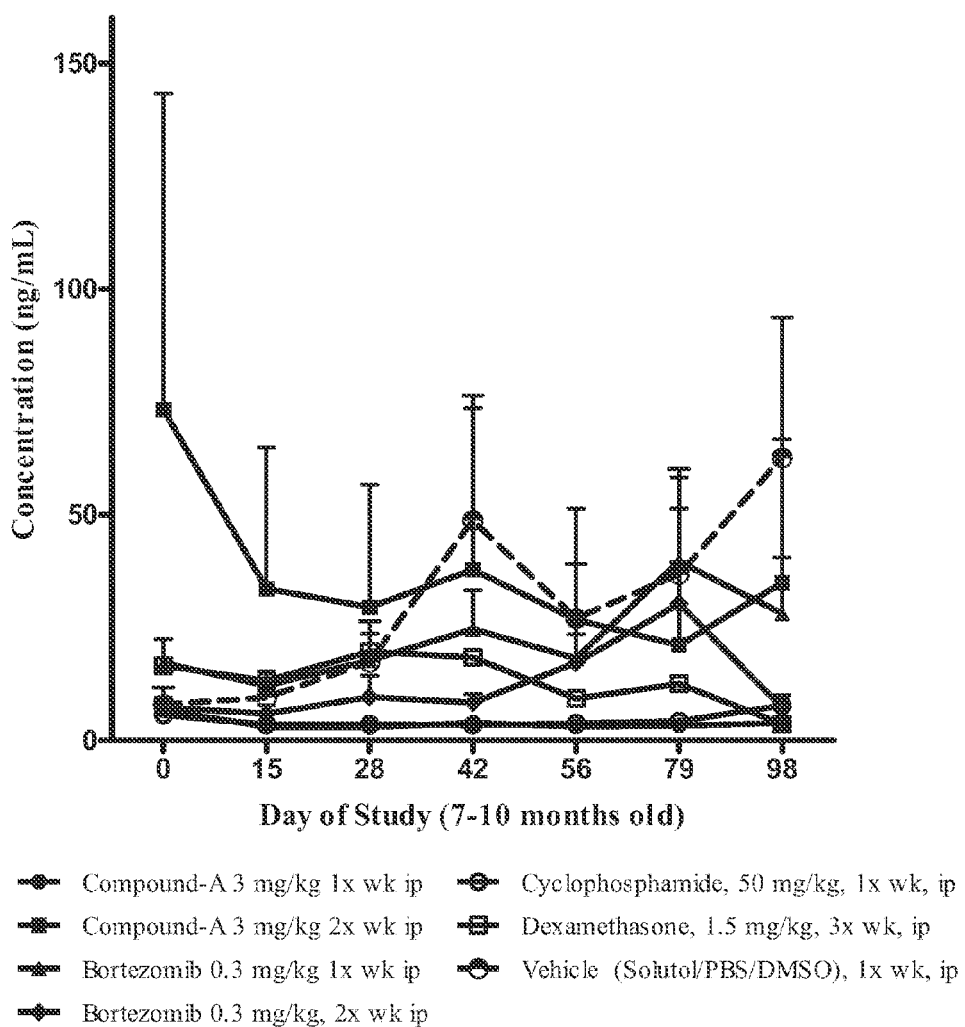
FIG. 26 depicts anti-Smith antigen antinuclear antibody concentrations in NZM mice. NZM mouse serum samples were analyzed for the presence of anti-smith antigen IgG circulating ANAs via ELISA assay. Mean±SEM values of anti-Smith Ag ANA concentration in ng/mL, 100-fold dilution from original stock.
Figure 27:
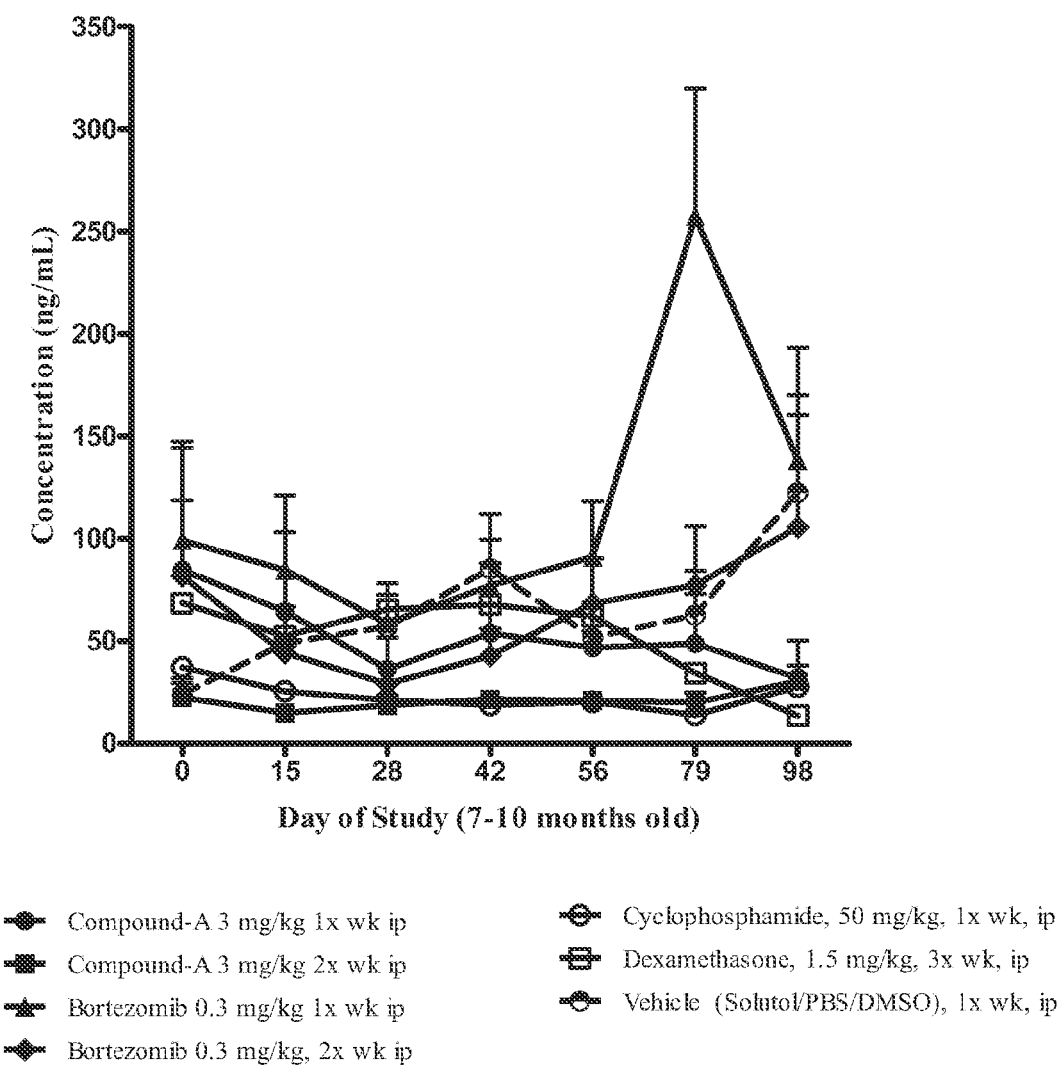
FIG. 27 depicts anti-dsDNA antinuclear antibody concentrations in NZM mice. NZM mouse serum samples were analyzed for the presence of anti-dsDNA IgG circulating ANAs via ELISA assay. Mean±SEM values of anti-dsDNA ANA concentration in ng/mL, 100-fold dilution from original stock.

Statistical test used was 1-way ANOVA.
NS = not significant;
NA = not applicable;
ND = not determined POUND A decreased serum anti-Smith Ag Ab as compared to once weekly bortezomib (88% versus 22% decrease compared to vehicle) (see FIG. 26 and Tables 26 and 41). Both once and twice weekly administration of COMPOUND A decreased serum anti-dsDNA Ab levels below that of once and twice weekly bortezomib (21% and 68% decrease versus 95% increase and 2% decrease as compared to vehicle controls) (see FIG. 27 and Tables 27 and 41).

TABLE 25

Statistics for Group Comparisons: Anti-chromatin Antinuclear Antibody Concentrations in Serum of NZM mice

| Group | G5-Bortezomib, 0.3 mg/kg 1× wk ip | G6-Bortezomib 0.3 mg/kg, 2× wk ip | G7-CTX 50 mg/kg 1× wk ip | G8-Dex 1.5 mg/kg, 3× wk ip | G9-Vehicle, 1× wk ip |
|---|---|---|---|---|---|
| G1 - COMPOUND A, 3 mg/kg 1× wk ip | $p < 0.001$ | NS | NS | NS | $p < 0.05$ |
| G2 - COMPOUND A, 3 mg/kg 2× wk ip | $p < 0.001$ | NS | NS | NS | $p < 0.05$ |
| G7 - CTX 50 mg/kg 1× wk ip | $p < 0.001$ | NS | NA | NS | NS |
| G8 - Dex, 1.5 mg/kg 3× wk ip | $p < 0.001$ | NS | NS | NA | NS |
| G9 - Vehicle, 1× wk ip | $p < 0.001$ | NS | NS | NS | NA |

Statistical analysis was performed by 1-way ANOVA;
NS = not significant;
NA = not applicable

TABLE 26

Statistics for Group Comparisons: Anti-smith Antigen Antinuclear Antibody Concentrations in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | NS | NS | $p < 0.01$ |
| G2 - COMPOUND A, 3 mg/kg 2× wk ip | NS | $p < 0.01$ | NS | $p < 0.01$ | NS |
| G7 - CTX 50 mg/kg 1× wk ip | NS | NS | NA | NS | $p < 0.01$ |
| G8 - Dex, 1.5 mg/kg 3× wk ip | NS | NS | NS | NA | NS |
| G9 - Vehicle, 1× wk ip | NS | NS | $p < 0.01$ | $p < 0.05$ | NA |

Statistics were performed by 1-way ANOVA analysis.
NS = not significant;
ND = not determined;
NA = not applicable

TABLE 27

Statistics for Group Comparisons: Anti-dsDNA Antinuclear Antibody Concentrations in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | $p < 0.05$ | NS | NS | NS | NS |
| G2 - COMPOUND A, 3 mg/kg 2× wk ip | $p < 0.001$ | NS | NS | NS | NS |
| G7 - CTX 50 mg/kg 1× wk ip | $p < 0.001$ | NS | NA | NS | NS |
| G8 - Dex, 1.5 mg/kg 3× wk ip | $p < 0.05$ | NS | NS | NA | NS |

TABLE 27-continued

Statistics for Group Comparisons: Anti-dsDNA Antinuclear Antibody Concentrations in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G9 - Vehicle, 1× wk ip | NS | NS | NS | NS | NA |

Statistics were performed using 1-way ANOVA analysis.
NS = not significant;
ND = not determined;
NA = not applicable.

This data is important because the presence of anti-dsDNA antibodies is associated with a poor prognosis of lupus and is strongly associated with developing, and often fatal, lupus nephritis (Egner 2000; Kiss, Lakos et al. 2009). COMPOUND A was superior to bortezomib in that only COMPOUND A provided significantly decreased serum anti-chromatin Ab as compared to vehicle, and only once weekly COMPOUND A provided significantly decreased serum anti-Smith Ag Ab as compared to vehicle. In addition, both once and twice weekly administration of COMPOUND A decreased serum anti-dsDNA Ab levels below that of once and twice weekly bortezomib.

Serum Cytokines

Figure 28:
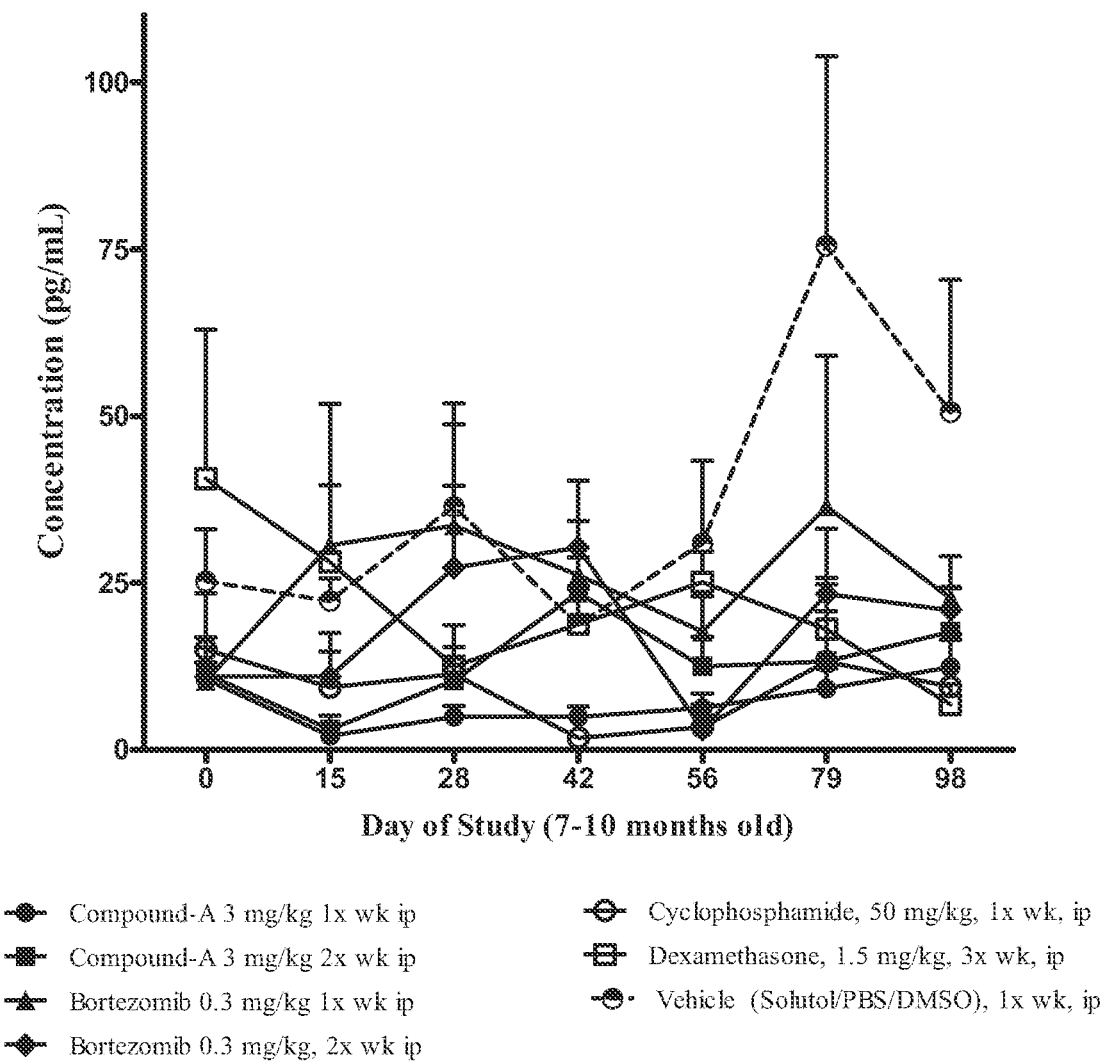
FIG. 28 depicts serum IL-12p40/p70 concentration over course of disease treatment in NZM mice. NZM mice were treated as outlined in the legend. Mean±SEM values for the concentration of mouse serum IL-12p40/p70 from treated NZM mice. Cytokines were analyzed using Luminex bead kits.
Figure 29:
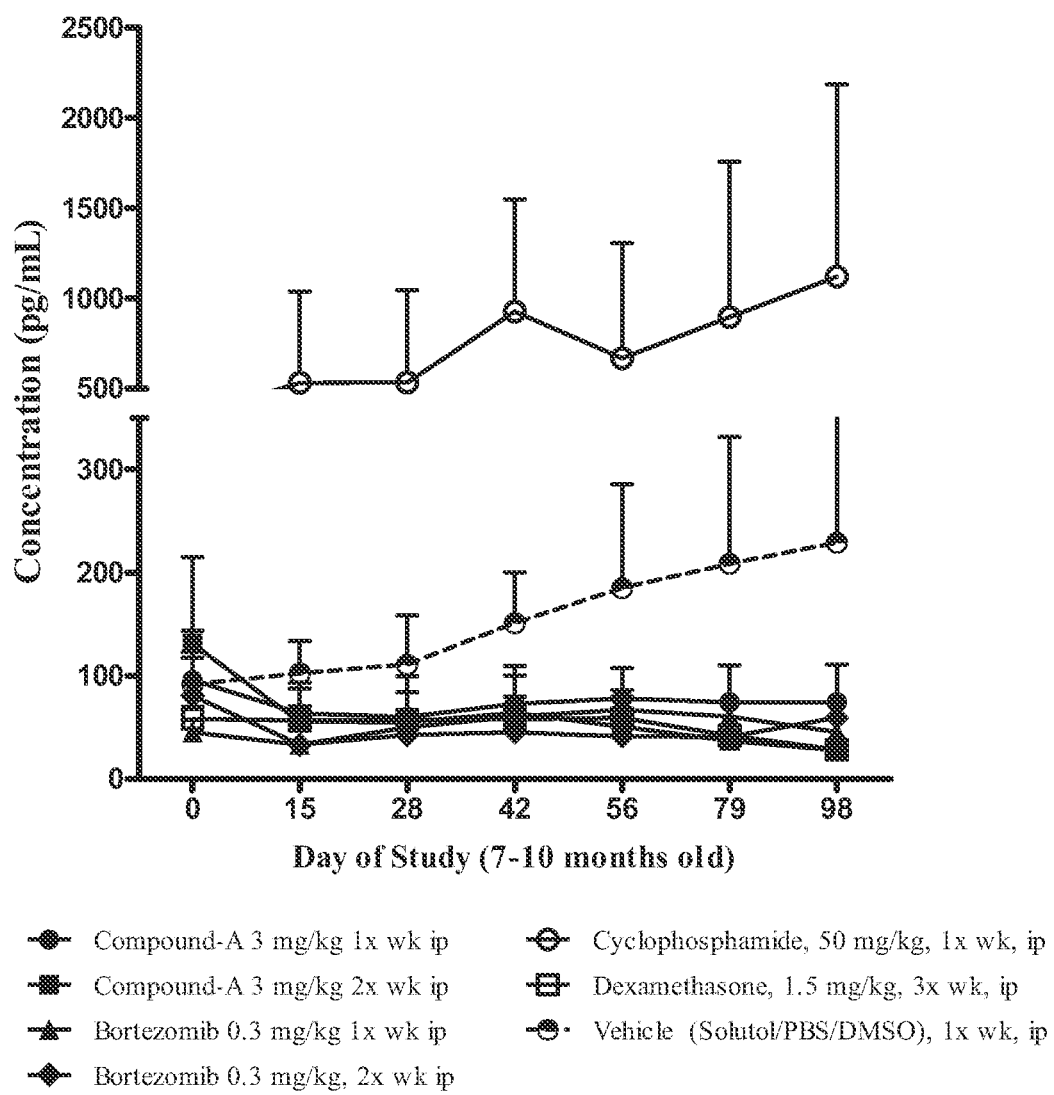
FIG. 29 depicts serum MIG concentration in NZM mice. NZM mice were treated as outlined in the legend. Graph shows Mean±SEM values for the concentration of mouse serum monokine, MIG, from treated NZM mice. Cytokines were analyzed using Luminex bead kits.
Figure 30:
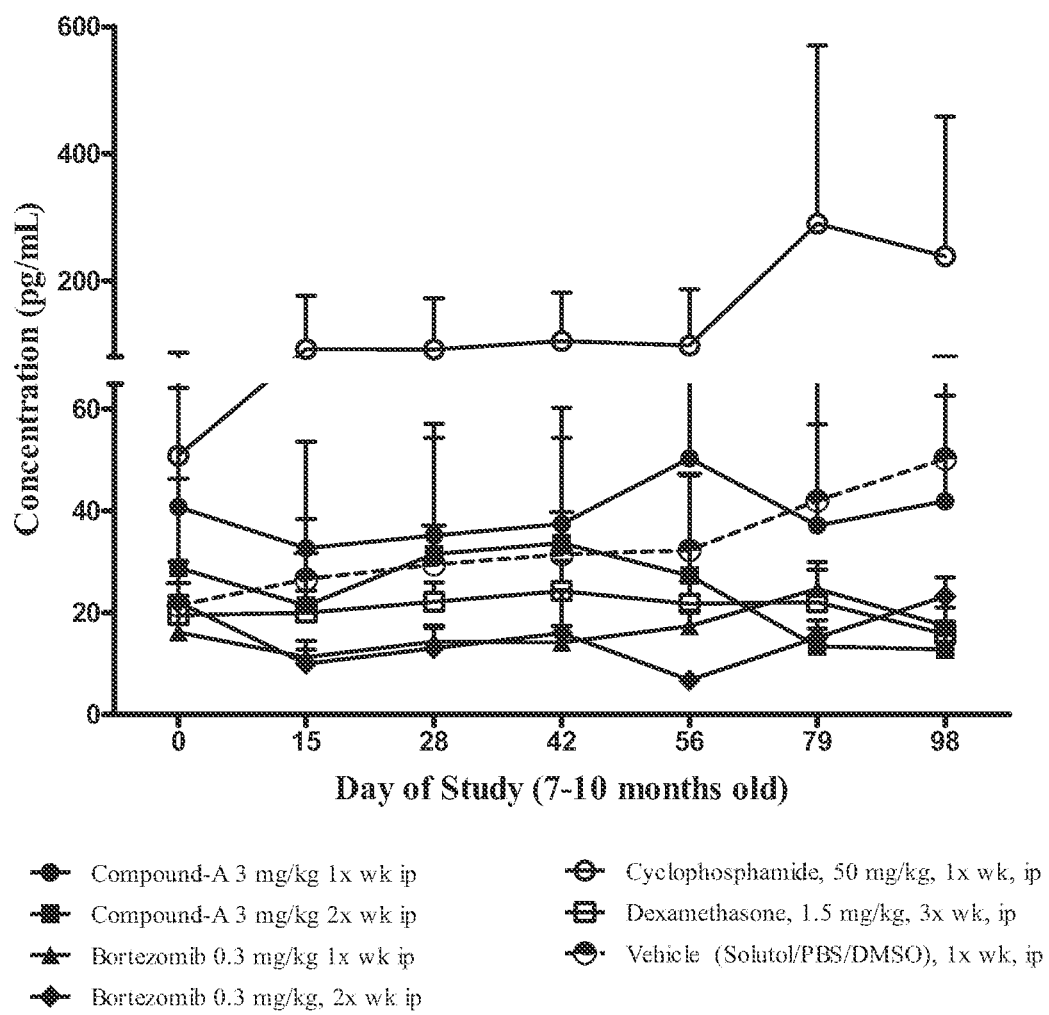
FIG. 30 depicts serum IP-10 concentration in NZM mice. NZM mice were treated as outlined in the legend. Graph shows Mean±SEM values for the concentration of mouse serum IFN-γ inducible protein, IP-10, from treated NZM mice. Cytokines were analyzed using Luminex bead kits.
Figure 31:
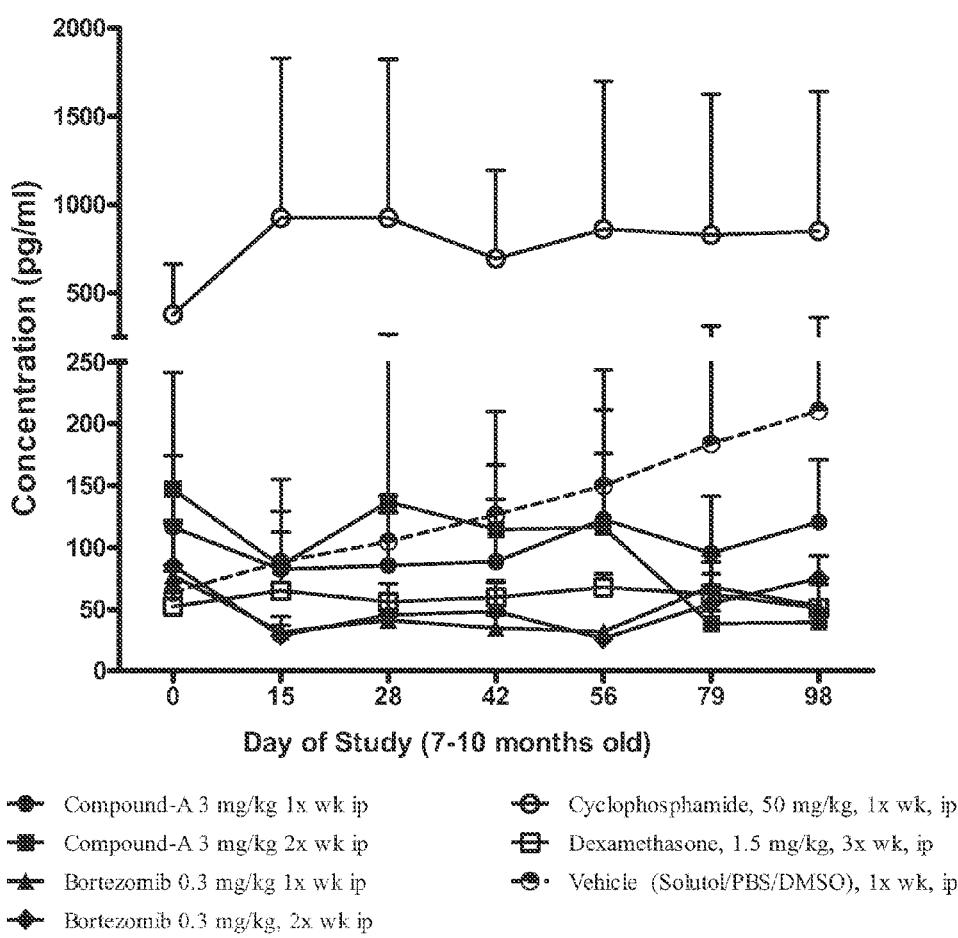
FIG. 31 depicts serum IL-13 concentration in NZM mice. NZM mice were treated as outlined in the legend. Graph shows Mean±SEM values for the concentration of mouse serum Th2 cytokine, IL-13, from treated NZM mice. Cytokines were analyzed using Luminex bead kits.
Figure 32:
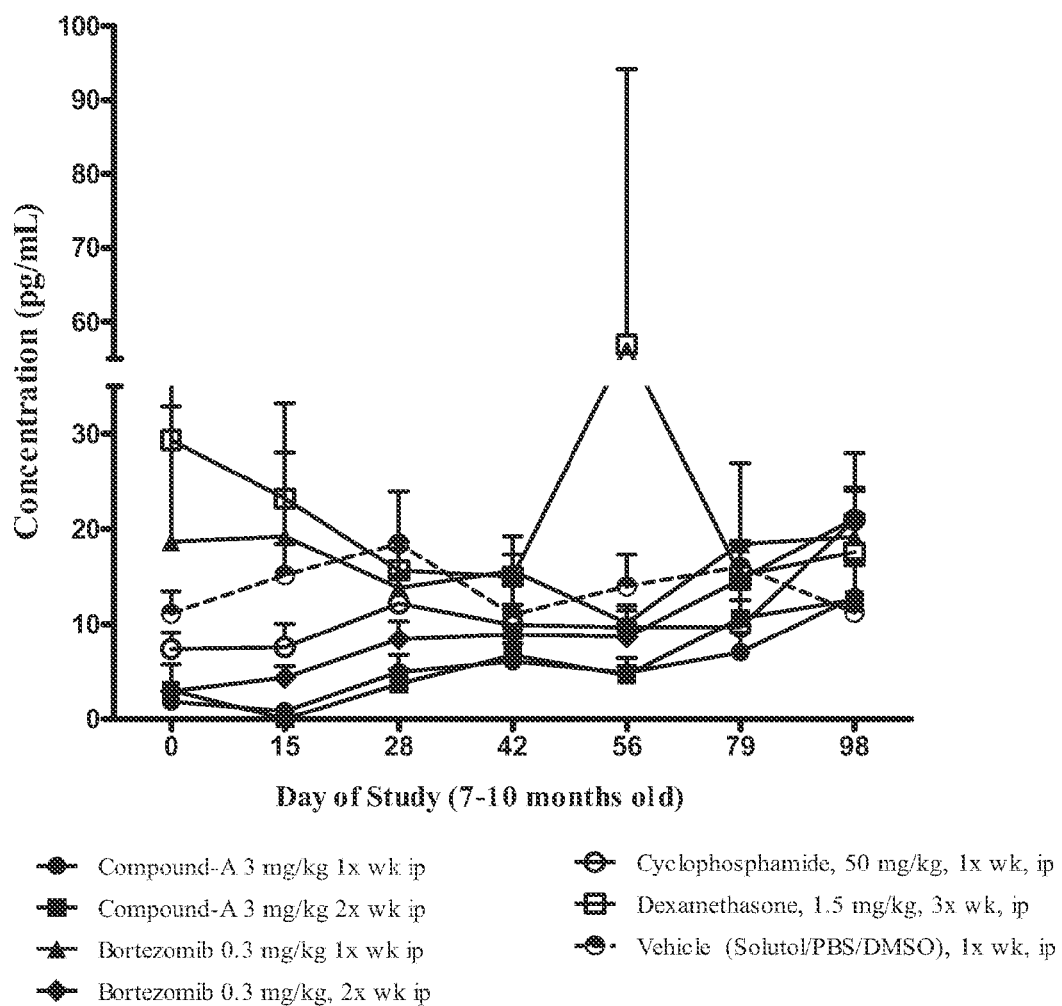
FIG. 32 depicts serum TNFα concentration in NZM mice. NZM mice were treated as outlined in the legend. Graph shows Mean±SEM values for the concentration of mouse serum proinflammatory cytokine, TNFα, from treated NZM mice. Cytokines were analyzed using Luminex bead kits.
Figure 33:
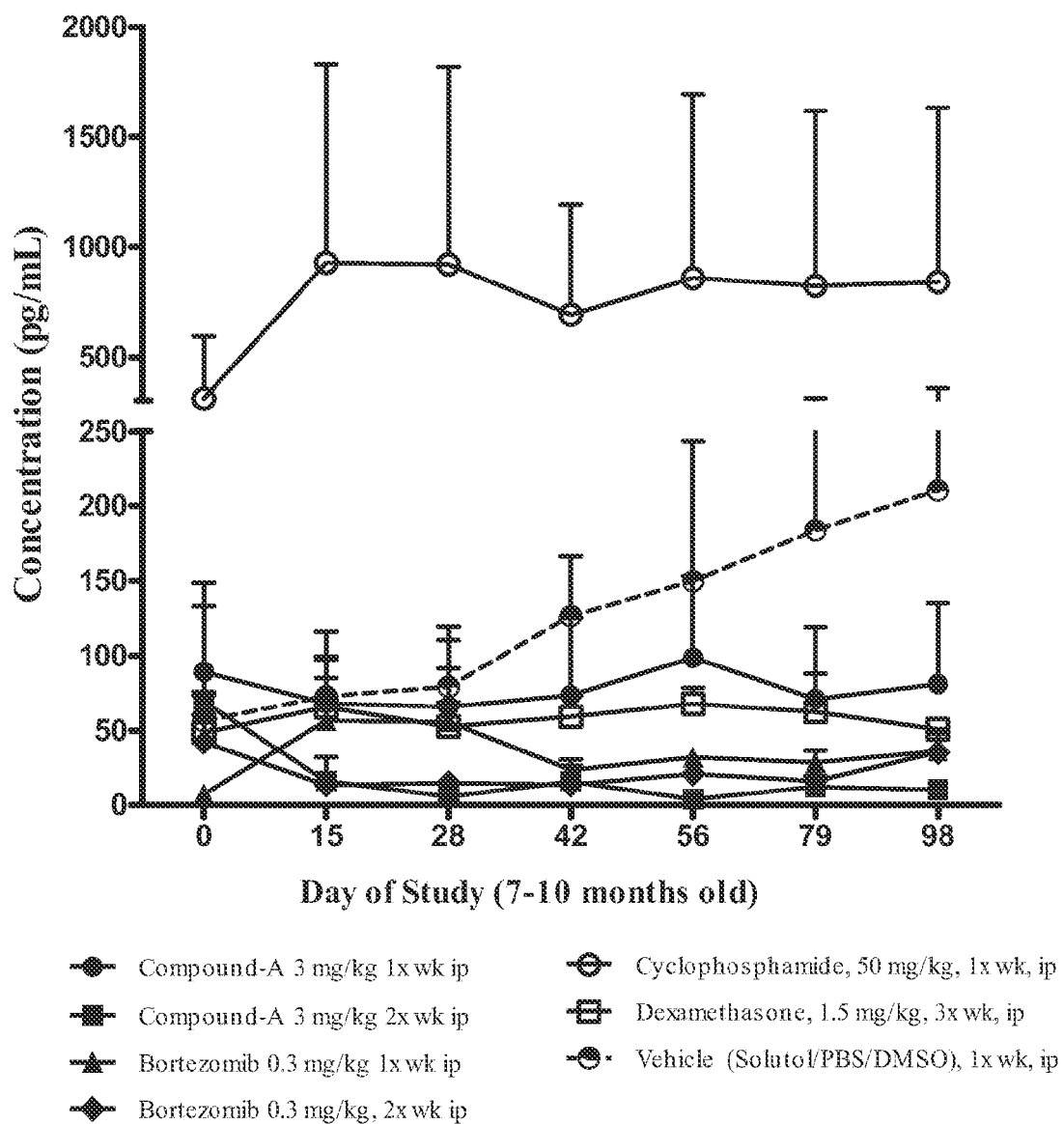
FIG. 33 depicts serum IL-17A concentration in NZM mice. NZM mice were treated as outlined in the legend. Graph shows Mean±SEM values for the concentration of mouse serum Th17 cytokine, IL-17A, from treated NZM mice. Cytokines were analyzed using Luminex bead kits.

NZM mice treated with COMPOUND A exhibited significantly decreased serum IL-12p40/p70 as compared to vehicle (83% and 67% decrease respectively; $p<0.01$) (see FIG. 28 and Tables 28 and 41). COMPOUND A provided a greater reduction in serum IL-12 levels than bortezomib as compared to the vehicle (67-83% decrease for COMPOUND A versus 32-55% decrease for bortezomib) (see FIG. 28 and Tables 28 and 41). Serum monocyte chemokine (ie, monokine), CXCL9/MIG decreased upon treatment with COMPOUND A or bortezomib as compared to CTX ($p<0.001$) but not to DEX (see FIG. 29 and Tables 29 and 41). Serum IFN-γ-inducible chemokine, CXCL10/IP-10, was decreased following treatment with COMPOUND A for the twice weekly dose as compared to vehicle (30% decrease), but significant changes were only seen as compared to CTX (see FIG. 30 and Tables 30 and 41). No significant change in IL-13 serum levels were observed for the COMPOUND A or bortezomib treatment groups as compared to vehicle (see FIG. 31 and Tables 31 and 41). Both once and twice weekly doses of COMPOUND A decreased serum TNFα over that of Dex ($p<0.001$) (see FIG. 32 and Tables 32 and 41). No significant change in IL-17A serum levels were observed for the COMPOUND A or bortezomib treatment groups as compared to vehicle (see FIG. 33 and Tables 33 and 41).

TABLE 28

Statistics for Group Comparisons: Serum IL-12p40/p70 Concentration in Treated NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | NS | NS | p < 0.001 |
| G2 - COMPOUND A, 3 mg/kg 2× wk ip | NS | NS | NS | NS | p < 0.01 |
| G7 - CTX 50 mg/kg 1× wk ip | NS | NS | NA | NS | p < 0.001 |
| G8 - Dex, 1.5 mg/kg 3× wk ip | NS | NS | NS | NA | NS |
| G9 - Vehicle, 1× wk ip | NS | p < 0.05 | p < 0.001 | NS | NA |

Statistics were performed using 1-way ANOVA analysis;
NS = not significant (p > 0.05);
NA = not applicable

TABLE 29

Statistics for Group Comparisons: Serum MIG Concentration in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | p < 0.001 | NS | NS |
| G2 - COMPOUND A, 3 mg/kg 2× wk ip | NS | NS | p < 0.001 | NS | NS |

TABLE 29-continued

Statistics for Group Comparisons: Serum MIG Concentration in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G7 - CTX 50 mg/kg 1× wk ip | p < 0.001 | p < 0.001 | NA | p < 0.001 | p < 0.001 |
| G8 - Dex, 1.5 mg/kg 3× wk ip | NS | NS | p < 0.001 | NA | NS |
| G9 - Vehicle, 1× wk ip | NS | NS | p < 0.001 | NS | NA |

Statistics used for comparisons was 1-way ANOVA;
NS = not significant (p > 0.05);
ND = not determined;
NA = not applicable

TABLE 30

Statistics for Group Comparisons: Serum IP-10 Concentration in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | p < 0.001 | NS | NS |
| G2 - COMPOUND A, 3 mg/kg 2× wk ip | NS | NS | p < 0.001 | NS | NS |
| G7 - CTX 50 mg/kg 1× wk ip | P < 0.001 | p < 0.001 | NA | P < 0.001 | p < 0.001 |
| G8 - Dex, 1.5 mg/kg 3× wk ip | NS | NS | p < 0.001 | NA | p < 0.001 |
| G9 - Vehicle, 1× wk ip | p < 0.001 | p < 0.001 | p < 0.001 | p < 0.001 | NA |

Statistics used for comparisons was 1-way ANOVA;
NS = not significant (p > 0.05);
NA = not applicable

TABLE 31

Statistics for Group Comparisons: Serum IL-13 Concentration in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | p < 0.001 | NS | NS |
| G2 - COMPOUND A, 3 mg/kg 2× wk ip | NS | NS | P < 0.001 | NS | NS |
| G7 - CTX 50 mg/kg 1× wk ip | p < 0.001 | p < 0.001 | NA | p < 0.001 | p < 0.001 |
| G8 - Dex, 1.5 mg/kg 3× wk ip | NS | NS | p < 0.001 | NA | NS |
| G9 - Vehicle, 1× wk ip | NS | NS | P < 0.001 | NS | NA |

Statistics used for comparisons was 1-way ANOVA;
NS = not significant (p > 0.05);
ND = not complicated;
NA = not applicable

TABLE 32

Statistics for Group Comparisons: Serum TNFα Concentration in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | NS | p <0.001 | NS |
| G2 - COMPOUND A, 3 mg/kg 2× wk ip | NS | NS | NS | p <0.001 | NS |
| G7 - CTX 50 mg/kg 1× wk ip | NS | NS | NA | p <0.05 | NS |
| G8 - Dex, 1.5 mg/kg 3× wk ip | NS | p <0.01 | p <0.05 | NA | NS |
| G9 - Vehicle, 1× wk ip | NS | NS | NS | NS | NA |

Statistics used for comparisons was 1-way ANOVA;
NS = not significant (p > 0.05);
ND = not determined;
NA = not applicable

TABLE 33

Statistics for Group Comparisons: Serum IL-17A Concentration in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | p < 0.01 | p < 0.001 | NS | NS |
| G2 - COMPOUND A, 3 mg/kg 2× wk ip | NS | NS | p < 0.001 | NS | NS |
| G7 - CTX 50 mg/kg 1× wk ip | NS | p < 0.001 | NA | p < 0.001 | p < 0.001 |
| G8 - Dex, 1.5 mg/kg 3× wk ip | NS | NS | p < 0.001 | NA | NS |
| G9 - Vehicle, 1× wk ip | NS | NS | NS | NS | NA |

Statistics used for comparisons was 1-way ANOVA;
NS = not significant (p > 0.05);
NA = not applicable These results are important because these cytokines are elevated in lupus patients, and are involved in the augmentation of lupus flares and ongoing immune responses to self antigens perpetuating the disease (Chun, Chung et al. 2007; Tucci, Lombardi et al. 2008). Reduction or modulation in these cytokine profiles can provide a favorable benefit for patients and provides an indirect indicator of disease resolution. (Morimoto, Tokano et al. 2001; Aringer and Smolen 2004; Chun, Chung et al. 2007; Niewold, Hua et al. 2007; Fu, Chen et al. 2008; Tucci, Lombardi et al. 2008). COMPOUND A was superior to bortezomib in that COMPOUND A provided a greater reduction in serum IL-12 levels than bortezomib as compared to vehicle.

Antibody-Secreting Cells

Figure 34:
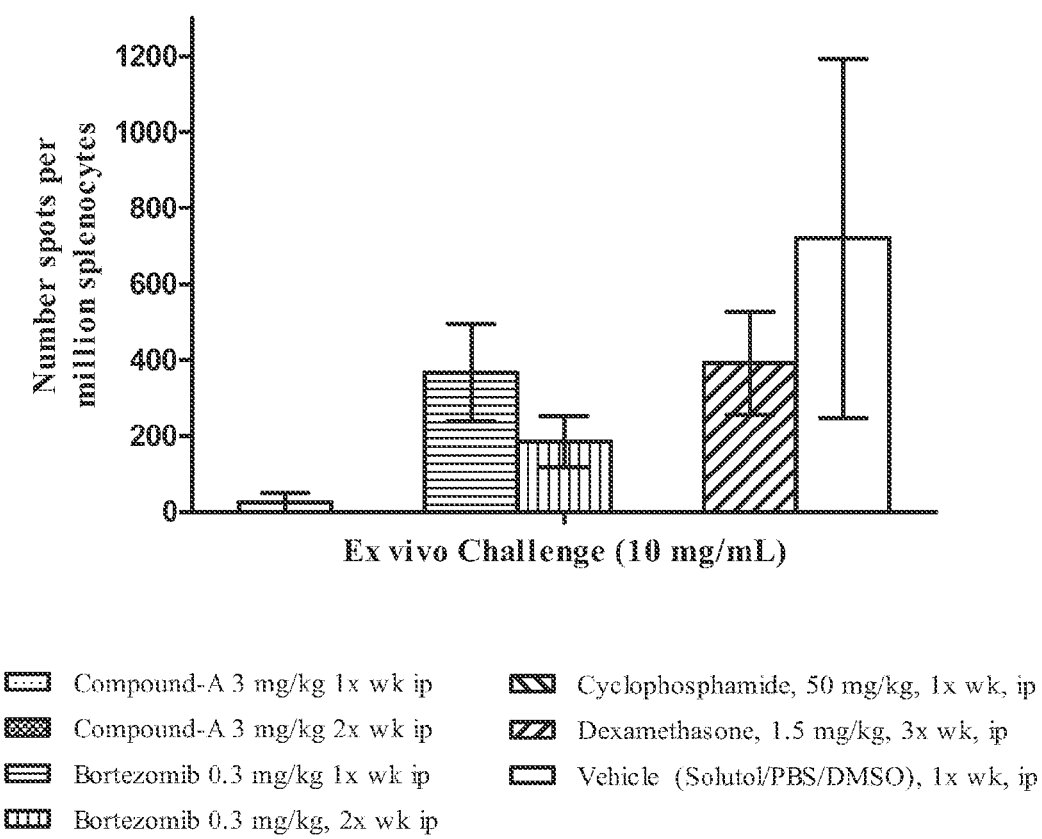
FIG. 34 depicts the frequency of anti-chromatin antibody secreting cells in the spleens of NZM mice. NZM treated mice spleens were processed for splenocytes for ex vivo Elispot assays. Elispot wells were coated with 10 μg/mL of boiled chicken chromatin or ovalbumin protein. Fresh, whole splenocytes were added to each well at 50,000 cells per well in cell culture medium. Cells were incubated overnight at 37° C. Developed wells provided spots that were counted as frequency of ASCs per million splenocytes. Graph shows Mean±SEM values.
Figure 35:
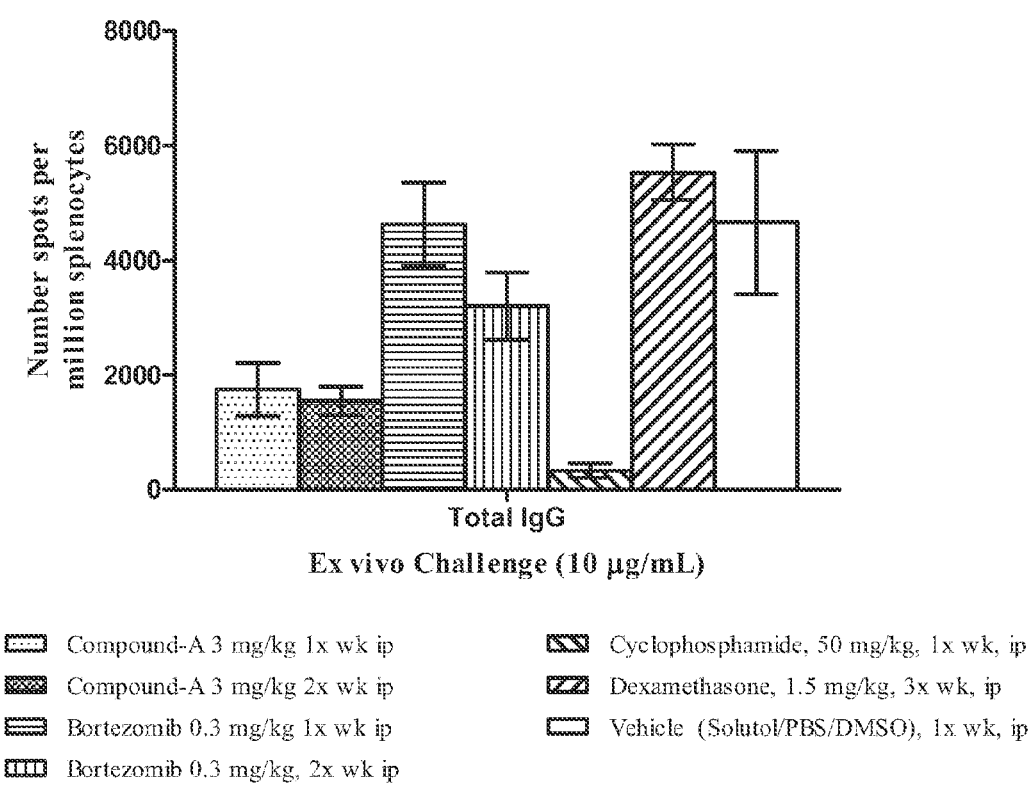
FIG. 35 depicts the frequency of total IgG antibody secreting cells in the spleens of NZM mice. NZM treated mice spleens were processed for splenocytes for ex vivo Elispot assays. Elispot wells were coated with 10 μg/mL of anti-mouse IgG, IgH, and IgL chains. Fresh, whole splenocytes were added to each well at 50,000 cells per well in cell culture medium. Cells were incubated overnight at 37° C. Developed wells provided spots that were counted as frequency of ASCs per million splenocytes. Graph shows Mean±SEM values.

NZM mice treated with COMPOUND A exhibited decreased anti-chromatin ASC frequencies below that of bortezomib, DEX, and vehicle (96-100% decrease in anti-chromatin ASC for COMPOUND A as compared to vehicle; p<0.01) (see FIG. 34 and Tables 34 and 41). Similar results were observed for total IgG producing ASC in the spleen of treated mice. COMPOUND A reduced total IgG producing ASC below that of weekly bortezomib, DEX, CTX, and vehicle (62-67%% decrease for CEP-1870 compared to vehicle) (see FIG. 35 and Tables 35 and 41).

TABLE 34

Statistics for Group Comparisons: Frequency of Anti-chromatin Antibody Secreting Cells in the Spleens of NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | p < 0.001 | p < 0.01 | NS | p < 0.01 | p < 0.01 |
| G2 - COMPOUND A, 3 mg/kg 2× wk ip | P < 0.01 | p < 0.05 | NS | NS | p < 0.01 |
| G7 - CTX 50 mg/kg 1× wk ip | P < 0.05 | p < 0.05 | NA | NS | p < 0.01 |

TABLE 34-continued

Statistics for Group Comparisons: Frequency of Anti-chromatin Antibody Secreting Cells in the Spleens of NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G8 - Dex, 1.5 mg/kg 3× wk ip | NS | NS | NS | NA | NS |
| G9 - Vehicle, 1× wk ip | NS | NS | p < 0.01 | NS | NA |

Statistics for comparisons included a two-tailed Mann-Whitney t- test or if required a Wilcoxon matched pairs test when Mann-Whitney not possible.
NS = not significant;
ND = not determined;
NA = not applicable

TABLE 35

Statistics for Group Comparisons: Frequency of Total IgG Antibody Secreting Cells in the Spleens of NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | p < 0.01 | NS | p < 0.01 | p < 0.01 | p < 0.05 |
| G2 - COMPOUND A, 3 mg/kg 2× wk ip | p < 0.001 | NS | p < 0.01 | p < 0.01 | p < 0.01 |
| G7 - CTX 50 mg/kg 1× wk ip | p < 0.001 | p < 0.001 | NA | P < 0.01 | p < 0.01 |
| G8 - Dex, 1.5 mg/kg 3× wk ip | NS | NS | p < 0.01 | NA | NS |
| G9 - Vehicle, 1× wk ip | NS | NS | p < 0.01 | NS | NA |

Statistics for comparisons included a two-tailed Mann-Whitney t-test or if required a Wilcoxon matched pairs test when Mann-Whitney not possible.
NS = not significant;
ND = not determined;
NA = not applicable This data is important because circulating autoantibody secreting cell types are directly correlative to a poor SLE prognosis (Neubert et al 2008, Sanz et al 2010, Muller et al 2008). COMPOUND A was superior to bortezomib in that COMPOUND A reduced anti-chromatin ASC significantly more than bortezomib, and only COMPOUND A (but not bortezomib) significantly reduced total IgG producing ASC as compared to vehicle.

Serum Complement

Figure 36:
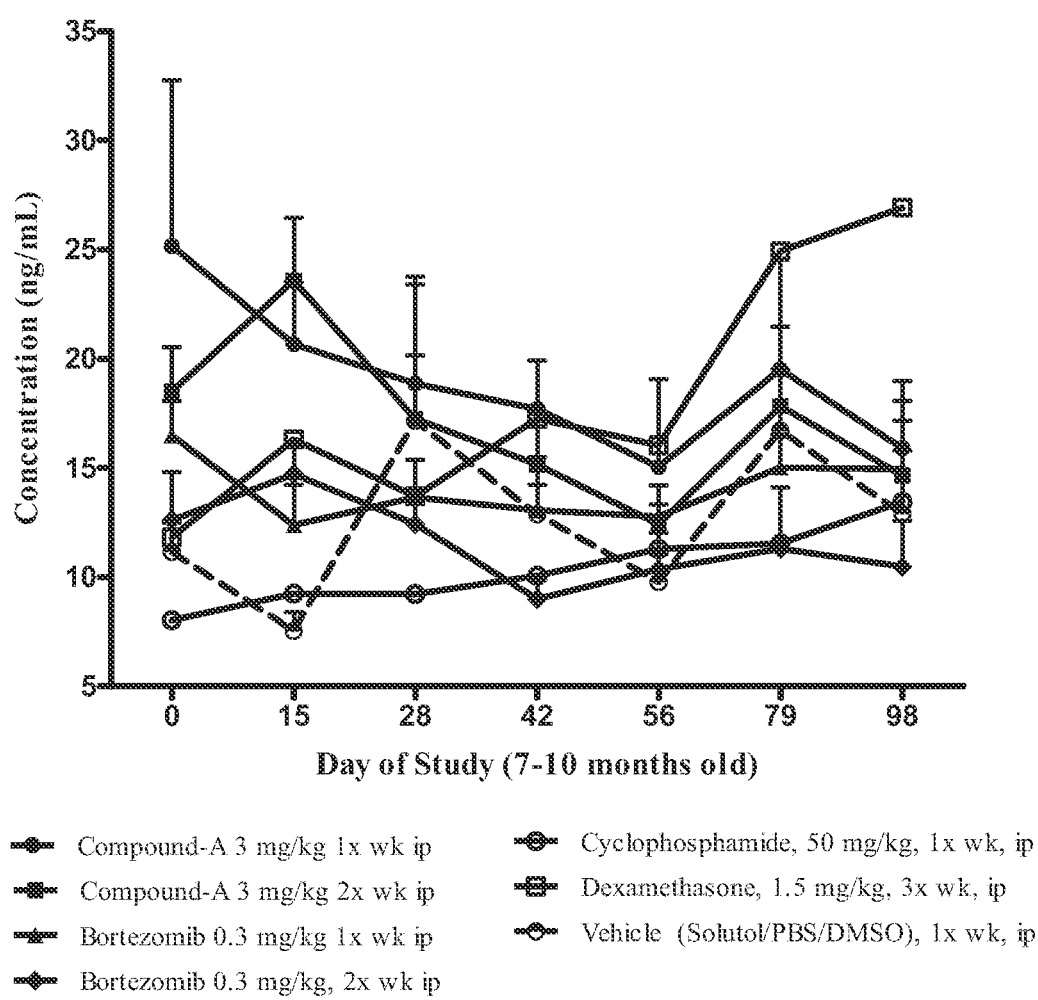
FIG. 36 depicts serum C3 complement levels in NZM mice. NZM serum samples were processed as described for ANA analysis. Serum was tested for total complement factor 3 (C3) concentration using a commercial kit. Graph shows serum sample diluted 1 to 50,000 in saline as mean±SEM values.

NZM mice treated with COMPOUND A exhibited increased complement C3 serum concentrations above that of CTX (p<0.001 for once weekly COMPOUND A; p<0.05 for twice weekly COMPOUND A) (see FIG. 36 and Tables 36 and 41). Only COMPOUND A once weekly increased C3 above vehicle (45% increase; p<0.05) (see FIG. 36 and Tables 36 and 41). The once weekly COMPOUND A group (G1) also significantly increased C3 levels above bortezomib twice weekly (p<0.01) (see FIG. 36 and Tables 36 and 41).

TABLE 36

Statistics for Group Comparisons: Serum C3 Complement Levels in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 2× wk po |
|---|---|---|---|---|---|
| G1 - COMPOUND A, 3 mg/kg 1× wk ip | NS | p < 0.01 | p < 0.001 | NS | p < 0.05 |
| G2 - COMPOUND A, 3 mg/kg 2× wk ip | NS | NS | p < 0.05 | NS | NS |
| G7 - CTX 50 mg/kg 1× wk ip | NS | NS | NS | p < 0.01 | NS |
| G8 - Dex, 1.5 mg/kg 3× wk ip | NS | p < 0.05 | p < 0.01 | NA | NS |
| G9 - Vehicle, 2× wk po | NS | NS | NS | NS | NA |

Statistics were performed using 1-way-ANOVA.
NS = not significant;
ND = not determined;
NA = not applicable This data is important because the level of C3 in the serum is indirectly correlated to the magnitude or extent of inflammation. SLE patients show reduced levels of C3 and C4 over time, which is indicative of increased systemic inflammation, which results in tissue organ damage. But with treatment these factors rebound, indicating that the treatment is reducing systemic inflammation and thus effectively treating the disease. Therefore, an increase in serum C3 is indicative of lupus disease resolution and treatment (Boumpas, Furie et al. 2003). COMPOUND A was superior to bortezomib in that only COMPOUND A (but not bortezomib) increased C3 as compared to vehicle.

Serum Collagen Type I Cross-Linker (CTx) Bone Resorption Biomarker

Figure 37:
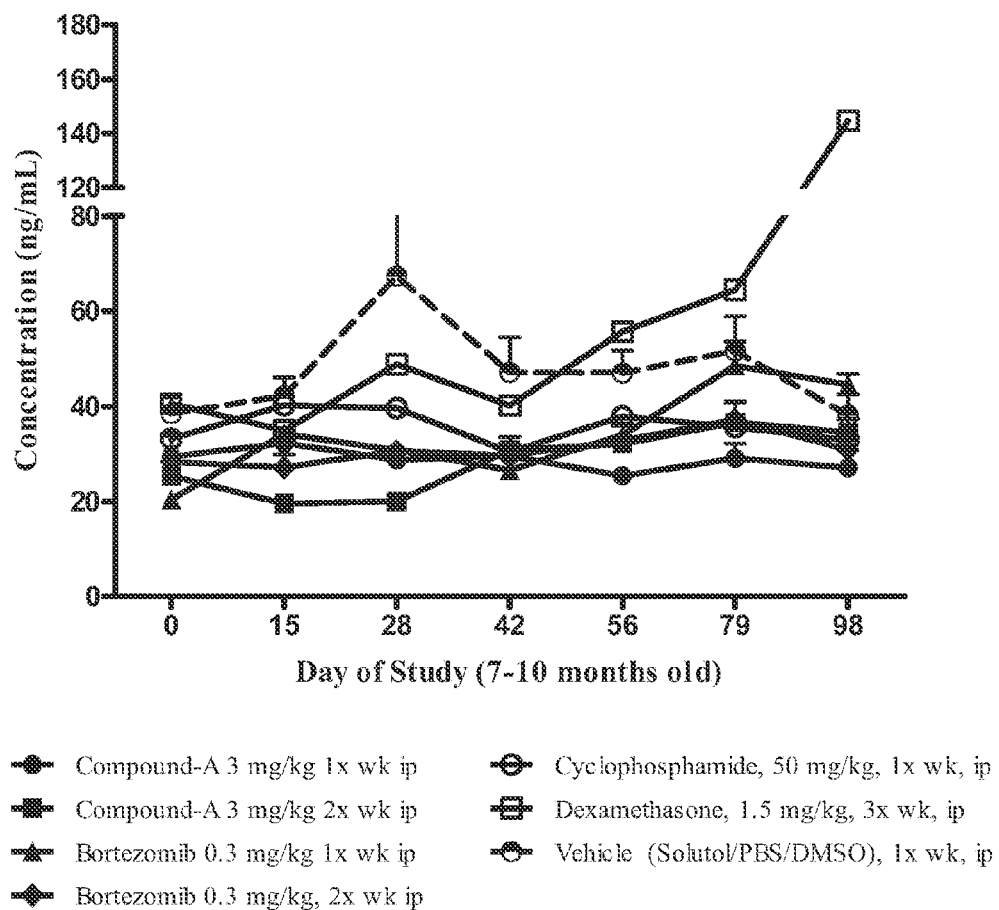
FIG. 37 depicts serum concentration of collagen type I cross-linker telopeptide (CTx) in NZM mice. NZM serum samples were processed as described for ANA analysis. Serum was tested for total collagen type I cross-linker (CTx) concentration, a biomarker for systemic bone resorption, using a commercial kit. Graph shows serum sample diluted 1 to 6 in saline as mean±SEM values.

NZM mice treated with either COMPOUND A or bortezomib exhibited no change in CTx levels as compared to vehicle (see FIG. 37 and Tables 37 and 41).

TABLE 37

Statistics for Group Comparisons: Serum Concentration of Collagen Type I Cross-linker in NZM Mice

| Groups | G5 - Bortezomib, 0.3 mg/kg 1× wk ip | G6 - Bortezomib 0.3 mg/kg, 2× wk ip | G7 - CTX 50 mg/kg 1× wk ip | G8 - Dex 1.5 mg/kg, 3× wk ip | G9 - Vehicle, 1× wk ip |
|---|---|---|---|---|---|
| G1 - COMPOUND A, 3 mg/kg 1× wk ip | NS | NS | NS | P < 0.01 | NS |
| G2 - COMPOUND A, 3 mg/kg 2× wk ip | NS | NS | NS | P < 0.01 | NS |
| G7 - CTX 50 mg/kg 1× wk ip | NS | NS | NA | ND | NS |
| G8 - Dex, 1.5 mg/kg 3× wk ip | p < 0.05 | p < 0.01 | ND | NA | NS |
| G9 - Vehicle, 1× wk ip | NS | NS | NS | NS | NA |

Statistics were performed using 1-way-ANOVA.
NS = not significant;
ND = not determined;
NA = not applicable Histopathological Analyses End-stage lupus nephritis was evaluated by histopathology and scored by a board certified pathologist for the assessment of total renal damage in diseased animals. NZM mice treated with COMPOUND A exhibited reduced incidence and severity of several renal histopathologies as compared to vehicle, including glomerular cellularity (~50% reduction), glomerulosclerosis (~53% reduction), interstitial infiltration (43-46% reduction), tubular atrophy (55-59% reduction), interstitial fibrosis (~55% reduction) and vasculitis (~51-55% reduction) (see FIG. 38 and Tables 38 and 41). Similar magnitudes in the reductions of the various renal histopathologies resulted from both once and twice weekly COMPOUND A treatment. Significant reductions in these renal histopathologies did not occur in this model in the bortezomib treatment group, excepting for a reduction in interstitial infiltration (44%) (see FIG. 38 and Tables 38 and 41). Both once and twice weekly administration of COMPOUND A decreased several renal pathologies below that of bortezomib, DEX- and vehicle-treated groups (glomerular cellularity, glomerular necrosis, glomerulosclerosis, interstitial infiltration, tubular atrophy, interstitial fibrosis, vaculitis). In general, COMPOUND A treatment positively impacted renal tissue damage and inflammation greater than that of bortezomib (e.g., ~45-55% decrease in score for COMPOUND A over several parameters vs. ~6-14% decrease in score for bortezomib as compared to vehicle) (see FIG. 38 and Tables 38 and 41). Both renal and lung infiltrates were observed in the vehicle-treated mice (see FIG. 39).

These results are important because they show that treatment of NZM mice with COMPOUND A can slow and/or prevent the development of lupus nephritis in lupus-prone mice. COMPOUND A was superior to bortezomib in that treatment with COMPOUND A significantly reduced renal damage in NZM mice as compared to vehicle (six of seven histopathologies were significantly reduced), but treatment with bortezomib failed to provide a significant reduction (of the seven histopathologies only interstitial infiltration was significantly reduced, and only for the twice weekly dose) (see FIG. 38 and Tables 38 and 41). COMPOUND A provided a significant decrease in five of the seven renal pathologies associated with lupus nephritis as compared to once weekly bortezomib (see FIG. 38 and Tables 38 and 41).

Pharmacodynamics

Figure 40:
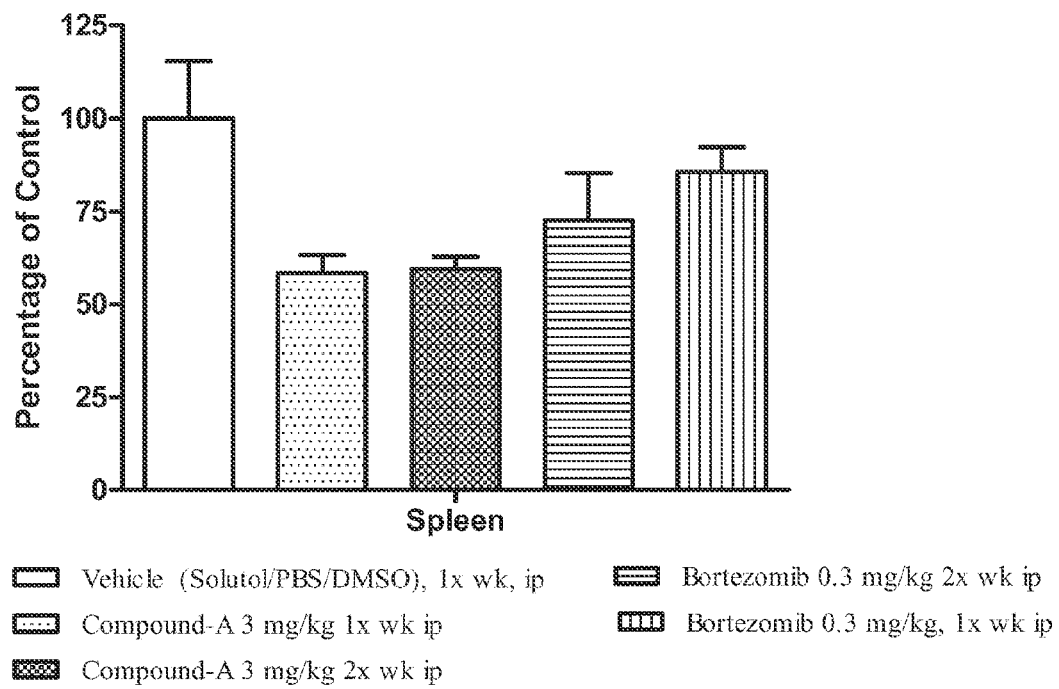
FIG. 40 depicts inhibition of the 20S proteasome in spleens of NZM mice. Spleens from treated NZM mice were lysed and analyzed using a functional ex vivo test for the 20S proteasome. Graph represents mean±SEM percent control for treatment groups.
Figure 41:
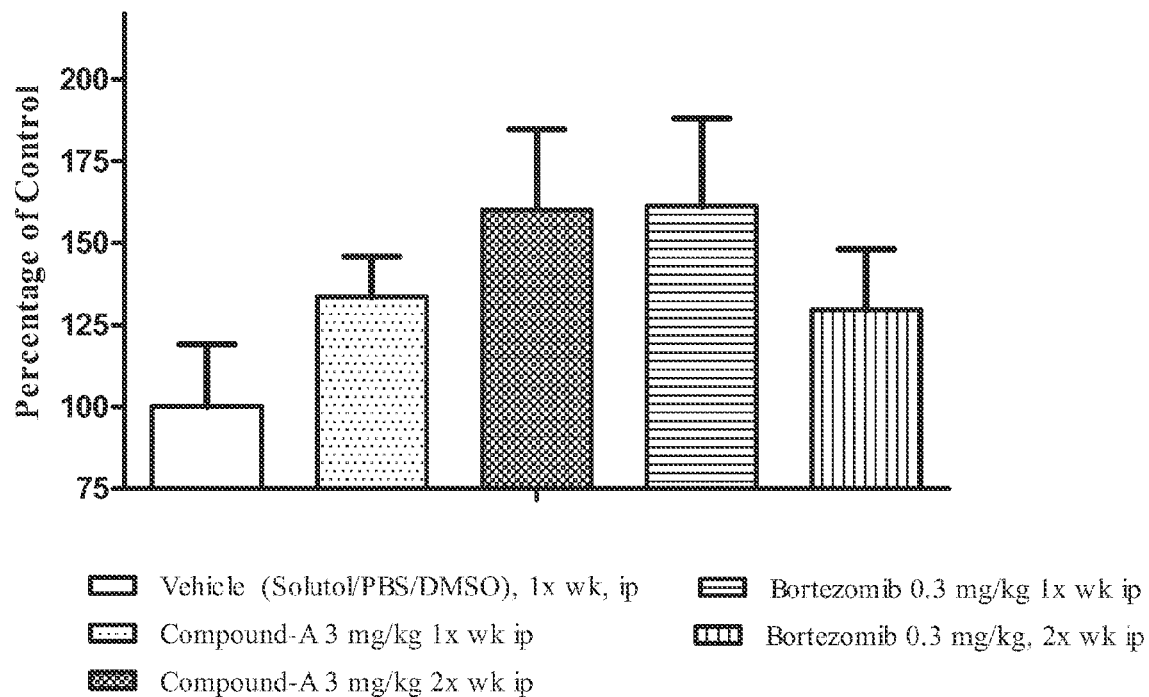
FIG. 41 depicts kidney IκBα accumulation 3 hours post dosing of NZM mice. Kidneys were lysed and analyzed using a commercial ELISA kit that measures the accumulation of cellular IκBα as a function of proteasome activity. Graph represents mean±SEM percent control for treatment groups.

Both 20S proteasome activity and IκBα accumulation were used as pharmacodynamic indicators of COMPOUND A-mediated proteasome inhibition in the spleen and kidneys of treated mice. NZM mice treated with COMPOUND A exhibited decreased function of the spleen 20S proteasome as compared to vehicle ($p<0.05$) (~40% inhibition relative to vehicle) (see FIG. 40 and Tables 39 and 41). Twice weekly administration of COMPOUND A increased the accumulation of kidney IκBα levels above that of the vehicle-treatment (~40% increase, $p<0.05$) (see FIG. 41 and Tables 40 and 41).

TABLE 38

Statistics for NZM Group Comparisons: Renal Histopathology Results

| | Pathology | G3 | G4 | G5 | G6 | G7 | G8 | G9 |
|---|---|---|---|---|---|---|---|---|
| COMPOUND A | GC | p < 0.01 | NS | NS | p < 0.01 | p < 0.001 | NS | NS |
| 3 mg/kg | GN | p < 0.05 | NS | NS | p < 0.01 | NS | NS | NS |
| 1× wk | GS | p < 0.001 | NS | NS | p < 0.001 | p < 0.01 | NS | NS |
| | II | NS | NS | NS | p < 0.01 | p < 0.05 | NS | NS |
| | TA | p < 0.001 | NS | NS | p < 0.001 | p < 0.001 | NS | NS |
| | IF | p < 0.01 | NS | NS | p < 0.001 | p < 0.01 | NS | NS |
| | VA | NS | NS | NS | p < 0.01 | p < 0.01 | NS | NS |
| COMPOUND A | GC | p < 0.01 | NS | NS | p < 0.01 | p < 0.001 | NS | NS |
| 3 mg/kg | GN | p < 0.05 | NS | NS | p < 0.01 | NS | NS | NS |
| 2× wk | GS | p < 0.001 | NS | NS | p < 0.001 | p < 0.01 | NS | NS |
| | II | NS | NS | NS | p < 0.01 | p < 0.05 | NS | NS |
| | TA | p < 0.01 | NS | NS | p < 0.001 | p < 0.001 | NS | NS |
| | IF | p < 0.01 | NS | NS | p < 0.001 | p < 0.01 | NS | NS |
| | VA | NS | NS | NS | NS | p < 0.05 | NS | NS |
| CTX | GC | NS | NS | NA | NS | p < 0.05 | NS | NS |
| 50 mg/kg | GN | NS | NS | NA | NS | NS | NS | NS |
| 1× wk | GS | NS | NS | NA | NS | NS | NS | NS |
| (G5) | II | NS | NS | NA | NS | NS | NS | NS |
| | TA | NS | NS | NA | NS | NS | NS | NS |
| | IF | NS | NS | NA | NS | NS | NS | NS |
| | VA | NS | NS | NA | NS | NS | NS | NS |
| DEX | GC | NS | NS | NS | NA | NS | p < 0.01 | NS |
| 1.5 mg/kg 1× | GN | NS | NS | p < 0.05 | NA | NS | p < 0.01 | p < 0.05 |
| wk | GS | NS | p < 0.001 | p < 0.05 | NA | NS | p < 0.001 | p < 0.05 |
| (G6) | II | NS | p < 0.01 | p < 0.05 | NA | NS | p < 0.05 | NS |
| | TA | NS | p < 0.01 | p < 0.05 | NA | NS | p < 0.01 | NS |
| | IF | NS | NS | p < 0.05 | NA | NS | p < 0.05 | NS |
| | VA | NS | NS | NS | NA | NS | NS | NS |
| Vehicle | GC | NS | NS | p < 0.05 | NS | NA | p < 0.001 | NS |
| (G7) | GN | NS | NS | NS | NS | NA | NS | NS |
| | GS | NS | NS | NS | NS | NA | p < 0.05 | NS |
| | II | NS | p < 0.05 | NS | NS | NA | NS | NS |
| | TA | NS | NS | NS | NS | NA | p < 0.05 | NS |
| | IF | NS | NS | NS | NS | NA | NS | NS |
| | VA | NS | NS | NS | NS | NA | NS | NS |
| NZW/LacJ | GC | p < 0.01 | NS | NS | p < 0.01 | p < 0.001 | NA | NS |
| non-diseased | GN | p < 0.05 | NS | NS | p < 0.01 | NS | NA | NS |
| (G8) | GS | p < 0.01 | NS | NS | p < 0.001 | p < 0.05 | NA | NS |
| | II | NS | NS | NS | p < 0.05 | NS | NA | NS |
| | TA | NS | NS | NS | p < 0.01 | p < 0.05 | NA | NS |
| | IF | NS | NS | NS | p < 0.05 | NS | NA | NS |
| | VA | NS | NS | NS | NS | NS | NA | NS |
| NZM | GC | NS | NS | NS | NS | NS | NS | NA |
| diseased | GN | NS | NS | NS | p < 0.05 | NS | NS | NA |
| baseline | GS | NS | NS | NS | p < 0.05 | NS | NS | NA |
| (G9) | II | NS | NS | NS | NS | NS | NS | NA |
| | TA | NS | NS | NS | NS | NS | NS | NA |
| | IF | NS | NS | NS | NS | NS | NS | NA |
| | VA | NS | NS | NS | NS | NS | NS | NA |

G3 - Bortezomib 0.3 mg/kg 1× wk
G4 - Bortezomib 0.3 mg/kg 2× wk
GC - Glomeruluar cellularity
GN - Glomerular necrosis
GS - Glomerulosclerosis
II - Interstitial infiltration
TA - Tubular atrophy
IF - Interstitial fibrosis
VA - Vasculitis

TABLE 39

Statistics for Group Comparisons: Inhibition of 20S Proteasome in Spleens of Treated NZM Mice

| Groups | G5 - Bortezomib, 0.3 mg/kg 1× wk ip | G6 - Bortezomib 0.3 mg/kg, 2× wk ip | G9 - Vehicle, 1× wk ip |
|---|---|---|---|
| G1 - COMPOUND A, 3 mg/kg 1× wk ip | p < 0.01 | NS | p < 0.05 |
| G2 - COMPOUND A, 3 mg/kg 2× wk ip | p < 0.01 | NS | p < 0.05 |
| G9 - Vehicle, 1× wk ip | NS | NS | NA |

Statistics were performed using a two-tailed Mann-Whitney t-test.
NS = not significant;
ND = not determined;
NA = not applicable

TABLE 40

Statistics for Group Comparisons: Kidney IκBα Accumulation 3 Hours Post Dosing of NZM Mice

| Groups | G5 - Bortezomib, 0.3 mg/kg 1× wk ip | G6 - Bortezomib 0.3 mg/kg, 2× wk ip | G9 - Vehicle, 1× wk ip |
|---|---|---|---|
| G1- COMPOUND A, 3 mg/kg 1× wk ip | NS | NS | NS |
| G2 - COMPOUND A, 3 mg/kg 2× wk ip | NS | NS | p < 0.05 |
| G9 - Vehicle, 1× wk ip | NS | NS | NA |

Statistics were performed using a one-tailed Mann-Whitney t-test.
NS = not significant;
ND = not determined;
NA = not applicable

TABLE 41

NZM Summary Percent Change vs Vehicle for Multiple Parameters

| Parameter | G1 | G2 | G3 | G4 | G5 | G6 | G7 | G8 | G9 |
|---|---|---|---|---|---|---|---|---|---|
| Body mass AUC | +9 | +10 | +13 | +11 | −1 | +4 | n/a | n/a | n/a |
| EOS survival | 100 | 91 | 58 | 75 | 10 | 70 | 45 | ND | n/a |
| Spleen mass EOS | −37 | −34 | 14 | −19 | −59 | −42 | n/a | n/a | n/a |
| Cytokine MIG AUC | −55 | −66 | −67 | −72 | −68 | 359 | n/a | n/a | n/a |
| Cytokine IL-12 AUC | −83 | −67 | −32 | −55 | −48 | −78 | n/a | n/a | n/a |
| Cytokine IP-10 AUC | +17 | −30 | −50 | −59 | −37 | 338 | n/a | n/a | n/a |
| Cytokine IL-13 AUC | −27 | −33 | −66 | −65 | −56 | 486 | n/a | n/a | n/a |
| Cytokine IL-17A AUC | −41 | −89 | −73 | −85 | −55 | 508 | n/a | n/a | n/a |
| Cytokine TNFα AUC | −61 | −57 | 12 | −29 | 79 | −25 | n/a | n/a | n/a |
| ASC total IgG EOS | −62 | −67 | −1 | −31 | +19 | −93 | n/a | n/a | n/a |
| ASC chromatin EOS | −96 | −100 | −46 | −74 | −42 | −100 | n/a | n/a | n/a |
| Serum C3 complement AUC | 45 | 32 | 8 | −11 | 45 | −18 | n/a | n/a | n/a |
| Serum CTx linker AUC | −41 | −40 | −27 | −35 | 21 | −26 | n/a | n/a | n/a |
| Urine proteinuria AUC | −61 | −72 | 30 | −57 | 27 | −68 | n/a | n/a | n/a |
| ANA chromatin AUC | −63 | −79 | 113 | −22 | −8 | −51 | n/a | n/a | n/a |
| ANA Smith Ag AUC | −88 | 8 | −22 | −53 | −56 | −86 | n/a | n/a | n/a |
| ANA dsDNA AUC | −21 | −68 | 95 | −2 | −19 | −66 | n/a | n/a | n/a |
| Kidney glomerular cellularity | −48 | −50 | −12 | −21 | −38 | −7 | n/a | −57 | −19 |
| Kidney glomerular necrosis | −29 | −29 | 18 | 3 | −16 | 42 | n/a | −43 | −24 |
| Kidney glomerulosclerosis | −54 | −53 | 8 | −29 | −17 | 34 | n/a | −53 | −14 |
| Kidney interstitial infiltration | −46 | −43 | −15 | −44 | −36 | 11 | n/a | −51 | −26 |
| Kidney tubular atrophy | −59 | −55 | −6 | −32 | −25 | 18 | n/a | −48 | −10 |
| Kidney interstitial fibrosis | −56 | −55 | −5 | −22 | −36 | 11 | n/a | −51 | −2 |
| Kidney vasculitis | −55 | −51 | −21 | −14 | −40 | 9 | n/a | −46 | −19 |
| PD 20S proteasome activity | −42 | −41 | −14 | −27 | ND | ND | n/a | n/a | n/a |
| PD IκBα accumulation | +33 | +60 | +61 | +29 | ND | ND | n/a | n/a | n/a |

Notes:
End of study values of percent live mice from original number for each group;
values in bold are significant (p ≤ 0.05) relative to vehicle treatment.
Percent differences were calculated based on AUC or EOS values as listed.
Lymphomegaly values represent the percent of mice with non enlarged lymph nodes.
ANA = antinuclear antibodies;
ASC = antibody secreting cells;
AUC = area under the curve;
EOS = end of study;
PD = pharmacodynamic;
CTx = carboxyterminal telopeptides of type I collagen.
G1 = COMPOUND A 3 mg/kg ip, 1× wk;
G2 = COMPOUND A 3 mg/kg ip, 2× wk;
G3 = bortezomib 0.3 mg/kg ip, 1× wk;
G4 = bortezomib 0.3 mg/kg ip, 2× wk;
G5 = Dex 1.5 mg/kg ip, 3× wk;
G6 = CTX 50 mg/kg ip, 1× wk;
G7 = vehicle PBS_3% DMSO + 10% Solutol, ip, 1× wk;
G8 = NZW/LacJ Non-Disease Mouse;
G9 = 7 month old NZM Baseline, 0 d Summary Treatment of lupus-prone NZM mice with COMPOUND A reduced disease symptoms of lupus nephritis and promoted survival. COMPOUND A resulted in greater survival, tolerability and reduction of several lupus-associated immune-parameters compared to dexamethasone, cyclophosphamide and bortezomib. For example, COMPOUND A reduced antichromatin autoantibody secreting cells (ASC) significantly more than bortezomib, only COMPOUND A (but not bortezomib) increased serum complement C3 as compared to vehicle, COMPOUND A (but not bortezomib) resulted in a significant reduction in the incidence and severity of multiple renal pathologies as compared to vehicle.

Example 3

COMPOUND A Administered Subcutaneously Effectively Treats Lupus in NZM mice

Protocol

Figure 42:
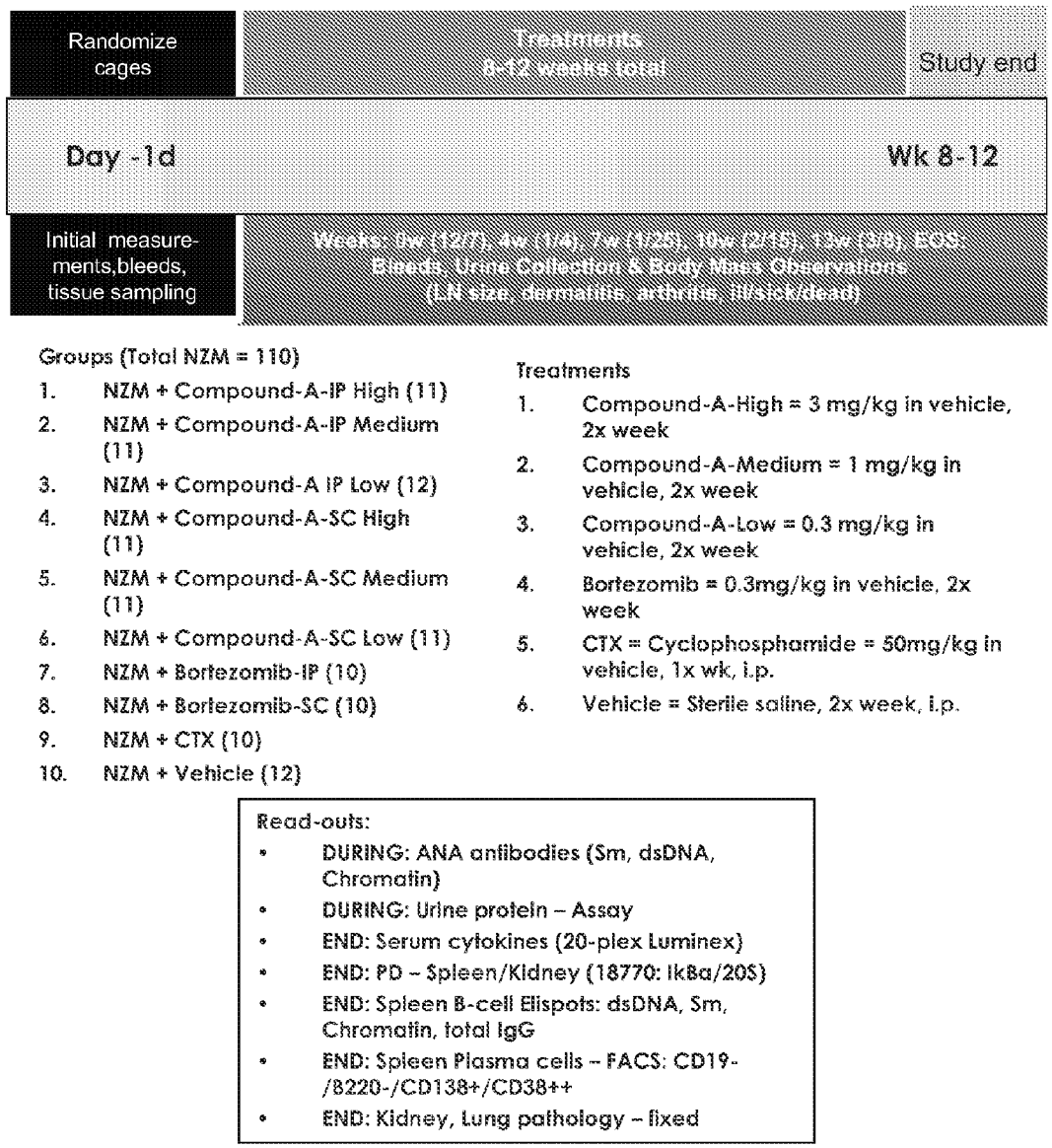
FIG. 42 depicts an overview of the experimental design for testing subcutaneous administration of COMPOUND A and bortezomib in the NZM lupus nephritis mouse model.

Treatments are summarized in FIG. 42 and Table 42. The study duration was 91 days, commencing at 212 days of age and ending at 303 days of age.

TABLE 42

Treatment Groups

| Group | Mouse/Strain | Drug | Dose | Route |
|---|---|---|---|---|
| G1 | NZM | COMPOUND A | 2.4 mg/kg# | ip |
| G2 | NZM | COMPOUND A | 1 mg/kg* | ip |
| G3 | NZM | COMPOUND A | 0.3 mg/kg** | ip |
| G4 | NZM | COMPOUND A | 3 mg/kg | sc |
| G5 | NZM | COMPOUND A | 1 mg/kg* | sc |
| G6 | NZM | COMPOUND A | 0.3 mg/kg** | sc |
| G7 | NZM | Bortezomib | 0.3 mg/kg | ip |
| G8 | NZM | Bortezomib | 0.3 mg/kg | sc |
| G9 | NZM | cyclophosphamide | 50 mg/kg | ip |
| G10 | NZM | Saline | n/a | ip |
| G11 | NZW/LacJ | n/a | n/a | n/a | initial dosing was 3.0 mg/kg, but on Day 15 it was reduced to 2.4 mg/kg due to observed toxicity
*initial dosing was 0.945 mg/kg, but on Day 36 it was increased to 1.0 mg/kg
**initial dosing was 0.23 mg/kg, but on Day 36 it was increased to 0.3 mg/kg
ip = intraperitoneal,
sc = subcutaneous,
n/a = not applicable.

Body Weight and Survival

Figure 43:
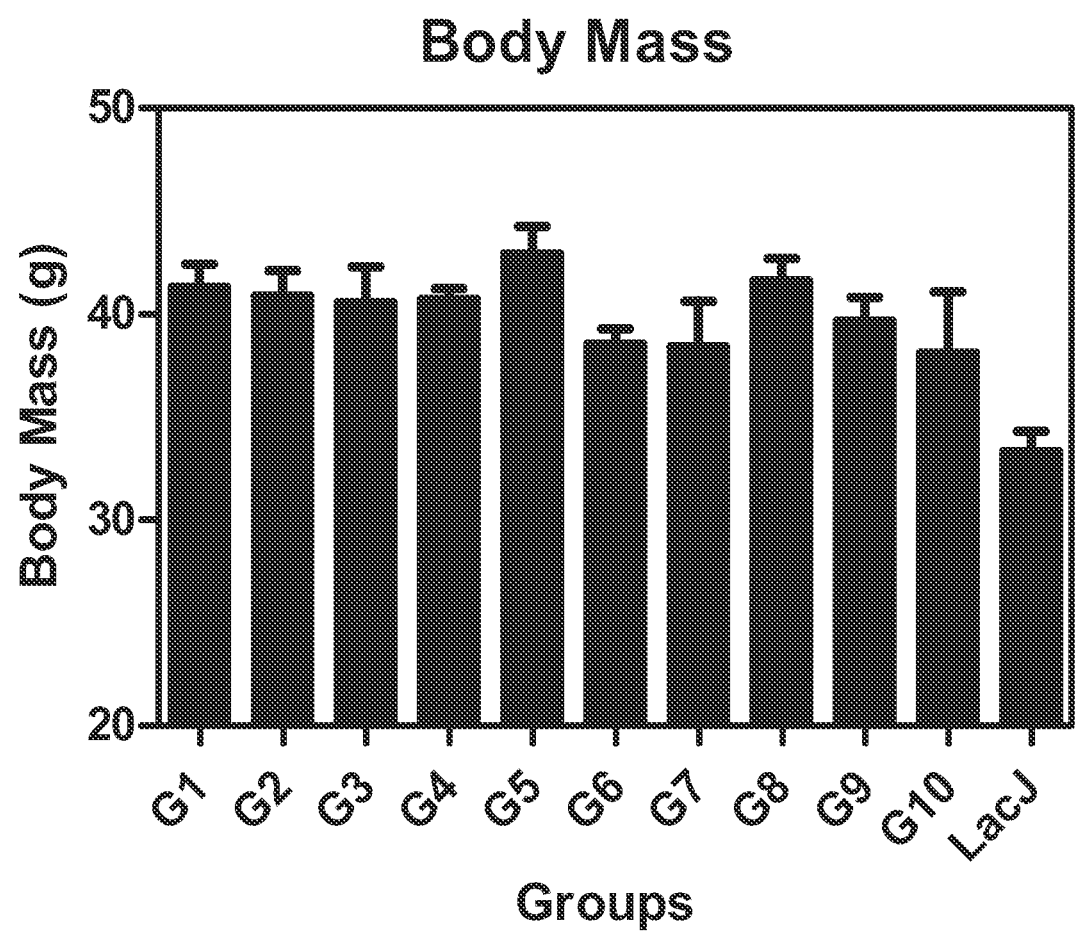
FIG. 43 depicts the body weight progression for NZM mice across treatment groups for the study duration. Graph shows Mean±SEM body mass for each group at the end of the study.
Figure 44:
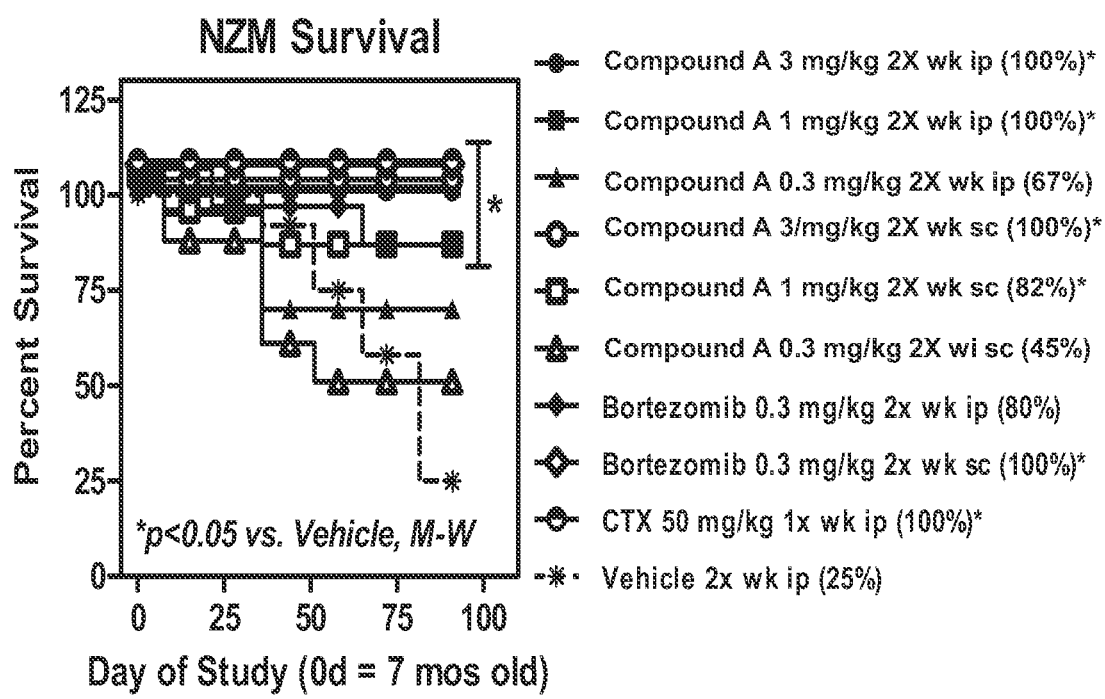
FIG. 44 depicts survival of NZM mice across treatment groups for the study duration. NZM mice were treated as outlined in the legend. Graph shows percent of live mice for each week of the study. The overall percentage of surviving mice at the 91 day endpoint is listed in parentheses within the legend. * indicates p≤0.05.

Body weight was relatively comparable across all treatment groups at end of study Day 91 (see FIG. 43). NZM mice treated with COMPOUND A in Groups 1, 2, and 4 exhibited significantly increased survival relative to vehicle (see FIG. 44).

Proteinuria

Figure 45:
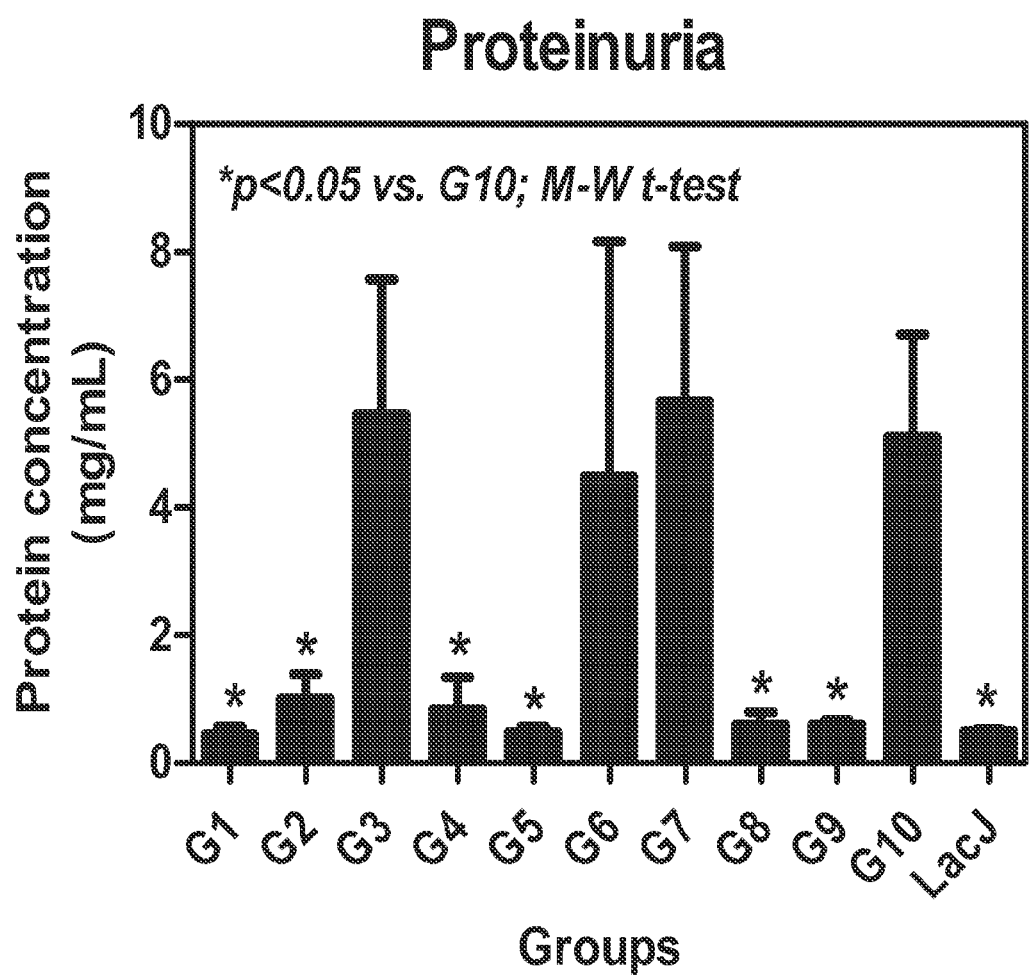
FIG. 45 depicts total urine protein (proteinuria) in NZM mice. Urine collected from NZM mice was analyzed for total protein content using a rat urinalysis kit. Graph shows Mean±SEM of protein concentration in mg/mL. * indicates p≤0.05.

NZM mice treated with COMPOUND A in Groups 1, 2, 4, and 5 exhibited reduced proteinuria as compared to vehicle (Group 10) and bortezomib administered ip (Group 7) (see FIG. 45).

Antinuclear Antibodies (ANAs)

Figure 46:
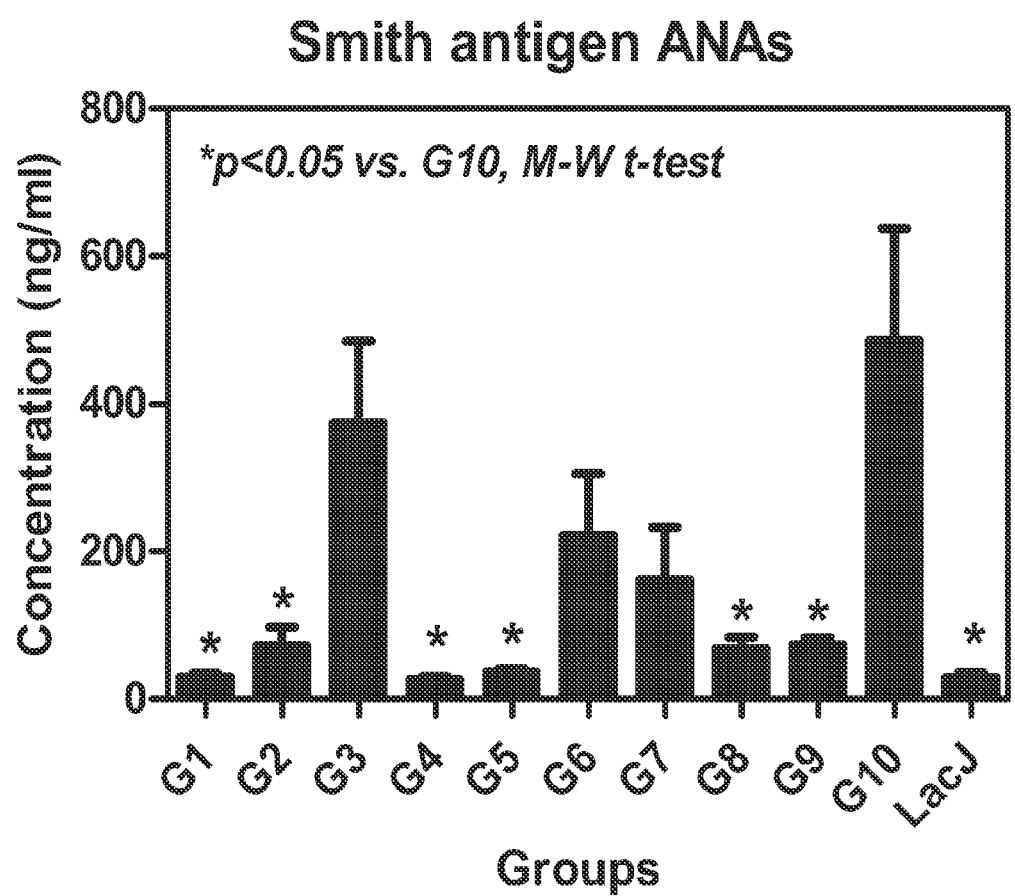
FIG. 46 depicts anti-Smith antigen antinuclear antibody concentrations in NZM mice. NZM mouse serum samples were analyzed for the presence of anti-smith antigen IgG circulating ANAs via ELISA assay. Mean±SEM values of anti-Smith Ag ANA concentration in ng/mL is listed as 100-fold dilution from original stock. * indicates p≤0.05 as compared to vehicle control G10.
Figure 47:
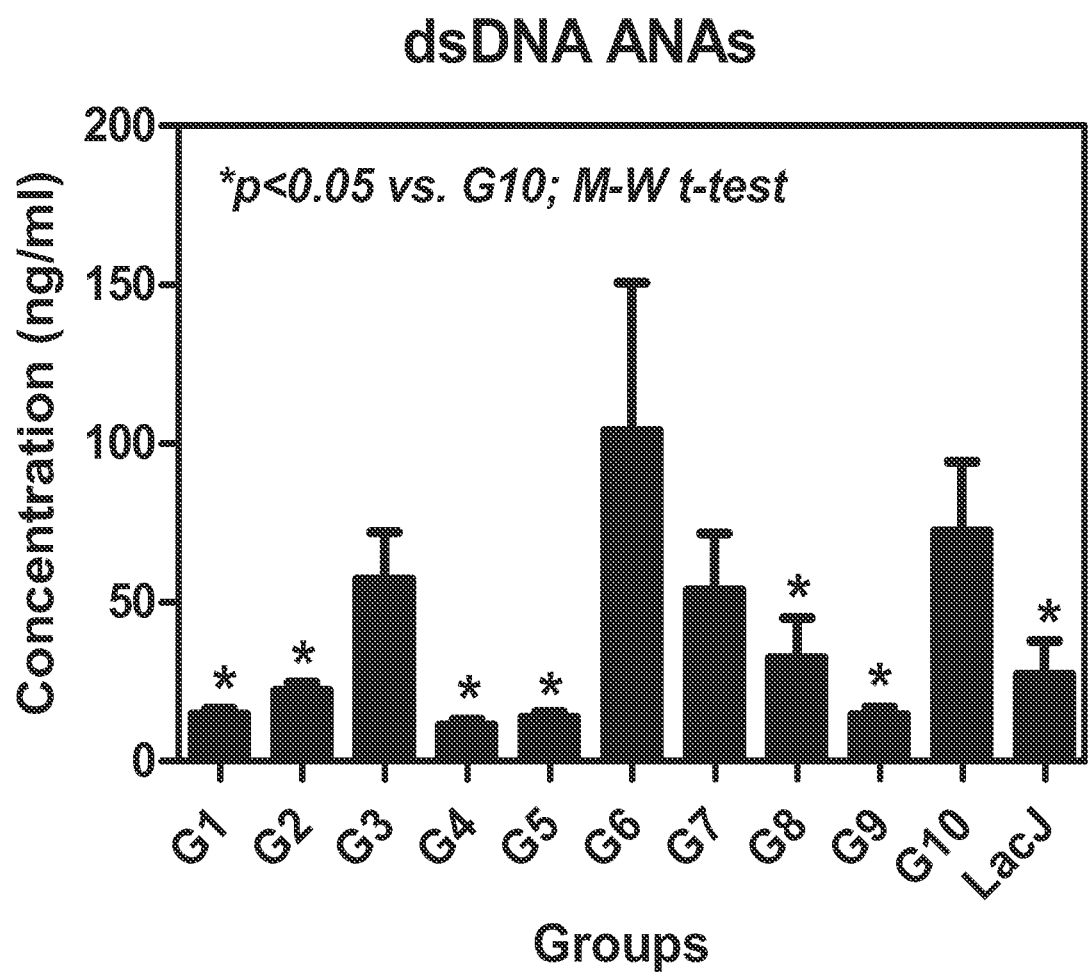
FIG. 47 depicts anti-dsDNA antinuclear antibody concentrations in NZM mice. NZM mouse serum samples were analyzed for the presence of anti-dsDNA IgG circulating ANAs via ELISA assay. Mean±SEM values of anti-dsDNA ANA concentration in ng/mL is listed as 100-fold dilution from original stock. * indicates p≤0.05 as compared to the vehicle control G10.

NZM mice treated with COMPOUND A exhibited significantly decreased serum anti-smith ANAs as compared to vehicle (93.8%, 85.0%, 94.5%, and 92.4% for Groups 1, 2, 4, and 5, respectively) (see FIG. 46). These reductions in anti-smith ANAs by COMPOUND A were greater than the reduction observed for the bortezomib ip treatment group (Group 7), which exhibited an insignificant reduction of only 66.7%. The bortezomib sc group (Group 8) exhibited a 85.7% decrease relative to the vehicle treatment group. NZM mice treated with COMPOUND A exhibited decreased serum anti-dsDNA ANAs compared to vehicle (79.6%, 69.2%, 84.1%, and 81.0% for Groups 1, 2, 4, and 5, respectively) (see FIG. 47). These reductions in anti-dsDNA ANAs by COMPOUND A were greater than the reduction observed for the bortezomib ip treatment group (Group 7), which exhibited an insignificant reduction of only 25.8%. The bortezomib sc group (Group 8) exhibited a 55.4% decrease relative to the vehicle treatment group.

Serum Cytokines

Figure 48:
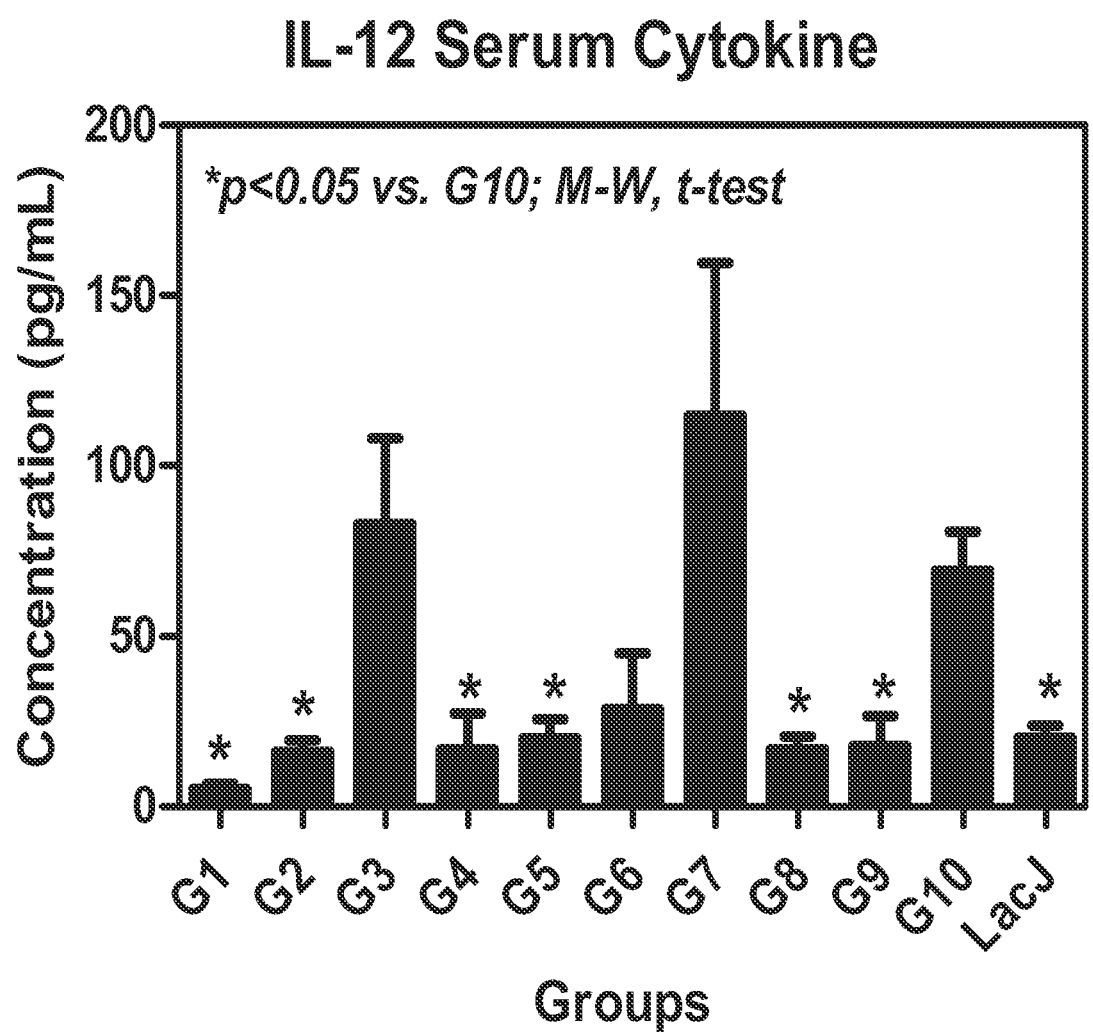
FIG. 48 depicts serum IL-12 concentration in NZM mice. Mean±SEM values for the concentration of mouse serum IL-12 from treated NZM mice at the end of the study. Cytokines were analyzed using Luminex bead kits. * indicates p≤0.05 as compared to the vehicle control G10.

NZM mice treated with COMPOUND A exhibited decreased serum IL-12 cytokine levels compared to vehicle (92.8%, 76.6%, 75.7%, and 70.8% for Groups 1, 2, 4, and 5, respectively) (see FIG. 48). These reductions in serum IL-12 cytokine levels by COMPOUND A were greater than the reduction observed for the bortezomib ip treatment group (Group 7), which exhibited an insignificant reduction of only 65.8%. The bortezomib sc group (Group 8) exhibited a 75.6% decrease relative to the vehicle treatment group.

Antibody-Secreting Cells

Figure 49:
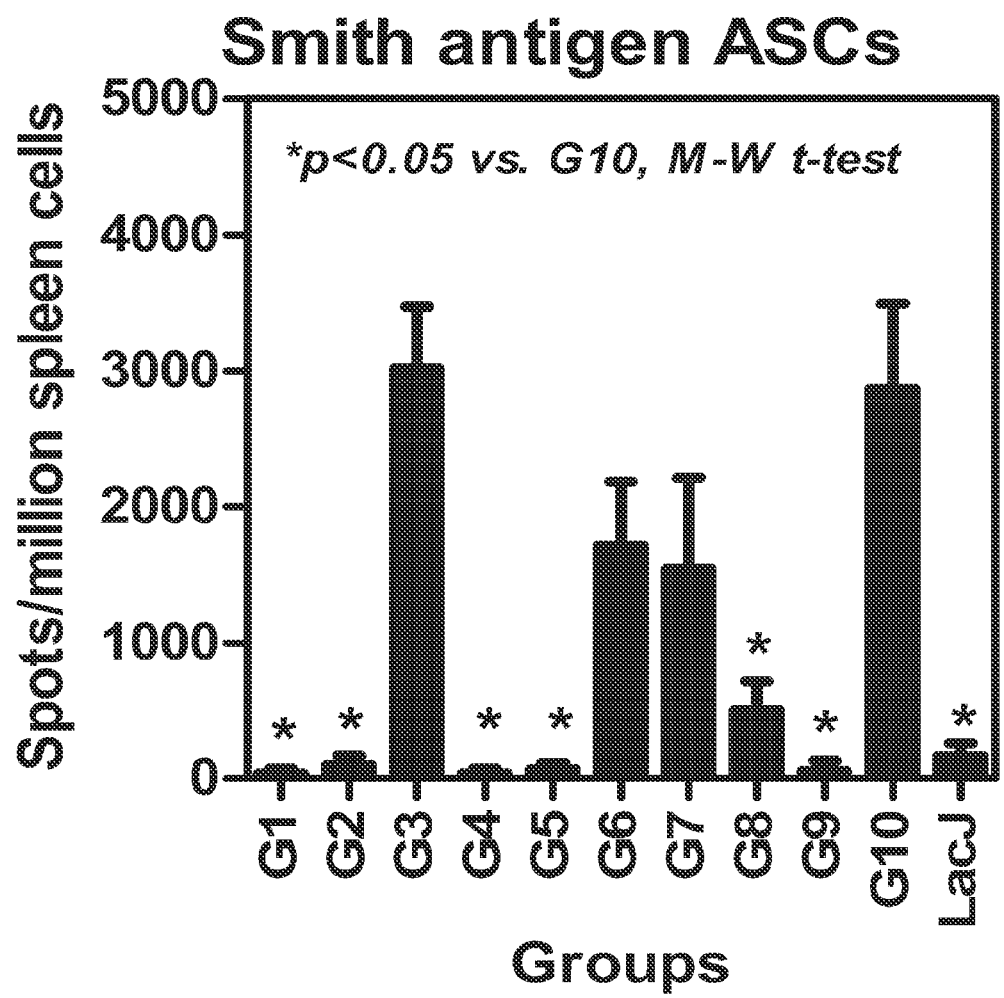
FIG. 49 depicts the frequency of anti-Smith antibody secreting cells in the spleens of NZM mice. NZM treated mice spleens were processed for splenocytes for ex vivo Elispot assays. Elispot wells were coated with 10 μg/mL of purified smith antigen or ovalbumin protein as a third party background control antigen. Fresh, whole splenocytes were added to each well at 500,000 cells per well in cell culture medium. Cells were incubated overnight at 37° C. Developed wells provided spots that were counted as frequency of ASCs per million splenocytes. Graph shows Mean±SEM values. * indicates p≤0.05 compared to vehicle control G10.
Figure 50:
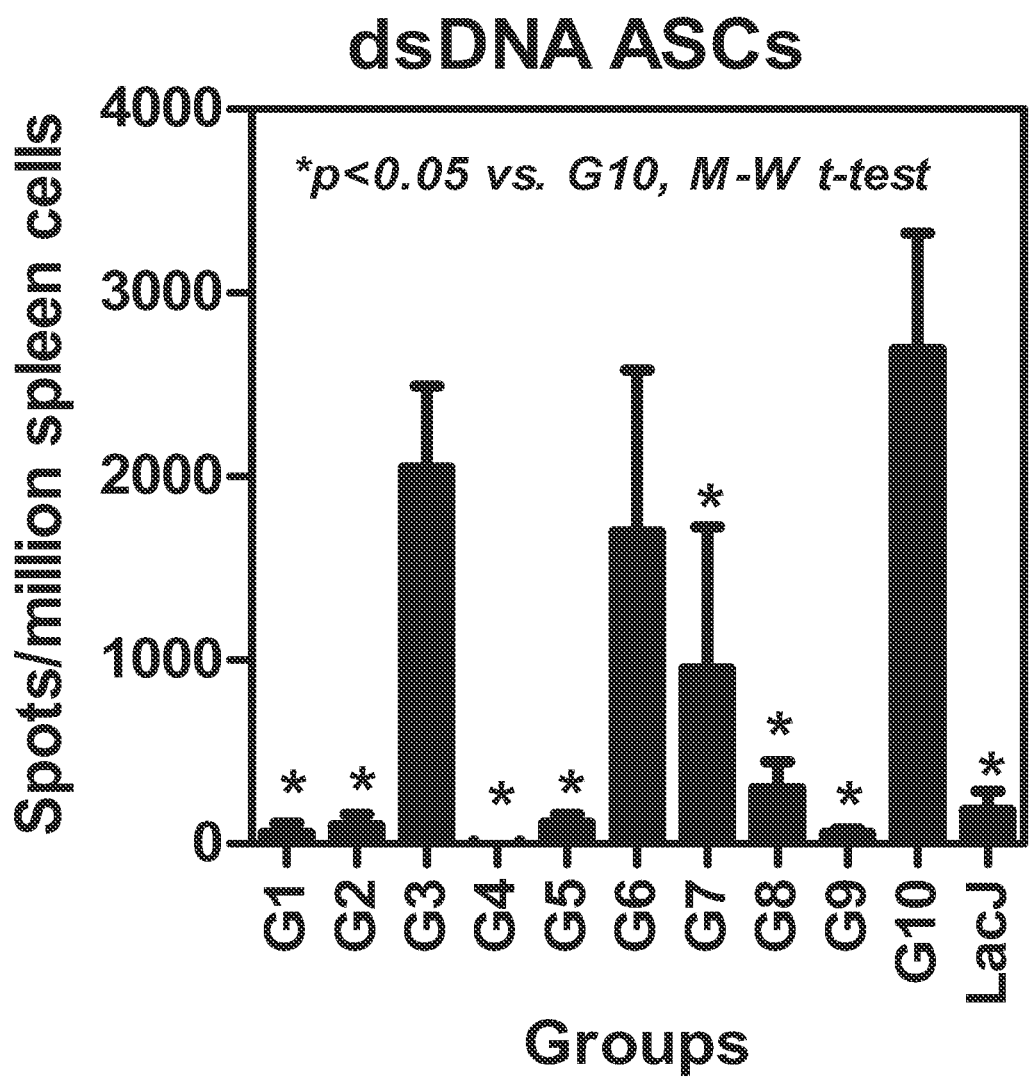
FIG. 50 depicts the frequency of anti-dsDNA antibody secreting cells in the spleens of NZM mice. NZM treated mice spleens were processed for splenocytes for ex vivo Elispot assays. Elispot wells were coated with 10 μg/mL of bovine dsDNA or ovalbumin protein as a third party background control antigen. Fresh, whole splenocytes were added to each well at 500,000 cells per well in cell culture medium. Cells were incubated overnight at 37° C. Developed wells provided spots that were counted as frequency of ASCs per million splenocytes. Graph shows Mean±SEM values. * indicates p≤0.05 compared to vehicle control G10.

NZM mice treated with COMPOUND A exhibited decreased anti-smith ASCs compared to vehicle (98.7%, 96.6%, 98.6%, and 97.6% for Groups 1, 2, 4, and 5, respectively) (see FIG. 49). These reductions in anti-smith ASCs by COMPOUND A were greater than the reduction observed for the bortezomib treatment group, which exhibited reductions of 46.3% and 82.4% for Groups 7 and 8, respectively. NZM mice treated with COMPOUND A exhibited decreased anti-sdDNA ASCs compared to vehicle (97.9%, 96.4%, 100.7%, and 95.9% for Groups 1, 2, 4, and 5, respectively) (see FIG. 50). These reductions in anti-dsDNA ASCs by COMPOUND A were greater than the reduction observed for the bortezomib treatment group, which exhibited reductions of 64.7% and 88.9% for Groups 7 and 8, respectively.

Spleen CD38/CD138+ Plasma Cells

Figure 51:
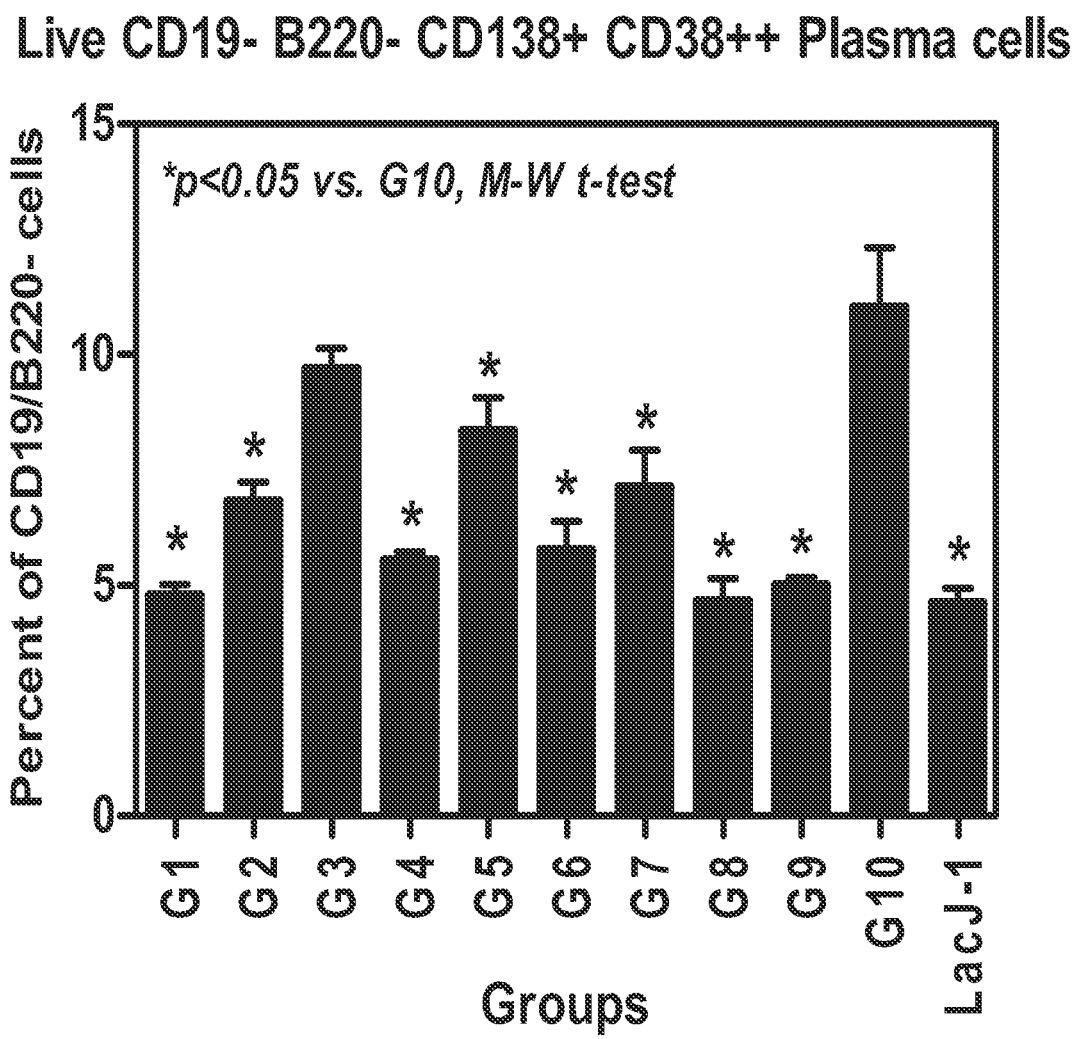
FIG. 51 depicts frequency of spleen CD38/CD138+ plasma cells in NZM mice. A total of 100,000 to 200,000 events were collected per tube of splenocytes stained with anti-CD19-FITC, anti-CD38-PE and anti-CD138-APC, acquired and analyzed on an Accuri flow cytometer. Live size gating was performed based on lymphocyte Fsc and Ssc scatter. CD19 negative histogram gated events were plotted as shown, by CD 138 and CD38. Representative data shown from a total of three mice analyzed randomly. T and B cell subset analysis not shown. Plots show proportion of spleen plasma cells in treated NZM mice. Graph shows Mean±SEM. * indicates p≤0.05 compared to vehicle control G10.

NZM mice treated with COMPOUND A exhibited decreased proportions of spleen CD19/CD45R double negative CD138/CD38 double positive plasma B cells compared to vehicle (56.6%, 38.1%, 49.8%, 24.3%, and 47.8% for Groups 1, 2, 4, 5, and 6, respectively) (see FIG. 51). The bortezomib treatment groups exhibited reductions of 35.4% and 57.8% for Groups 7 and 8, respectively.

Histopathological Analyses

Figure 52:
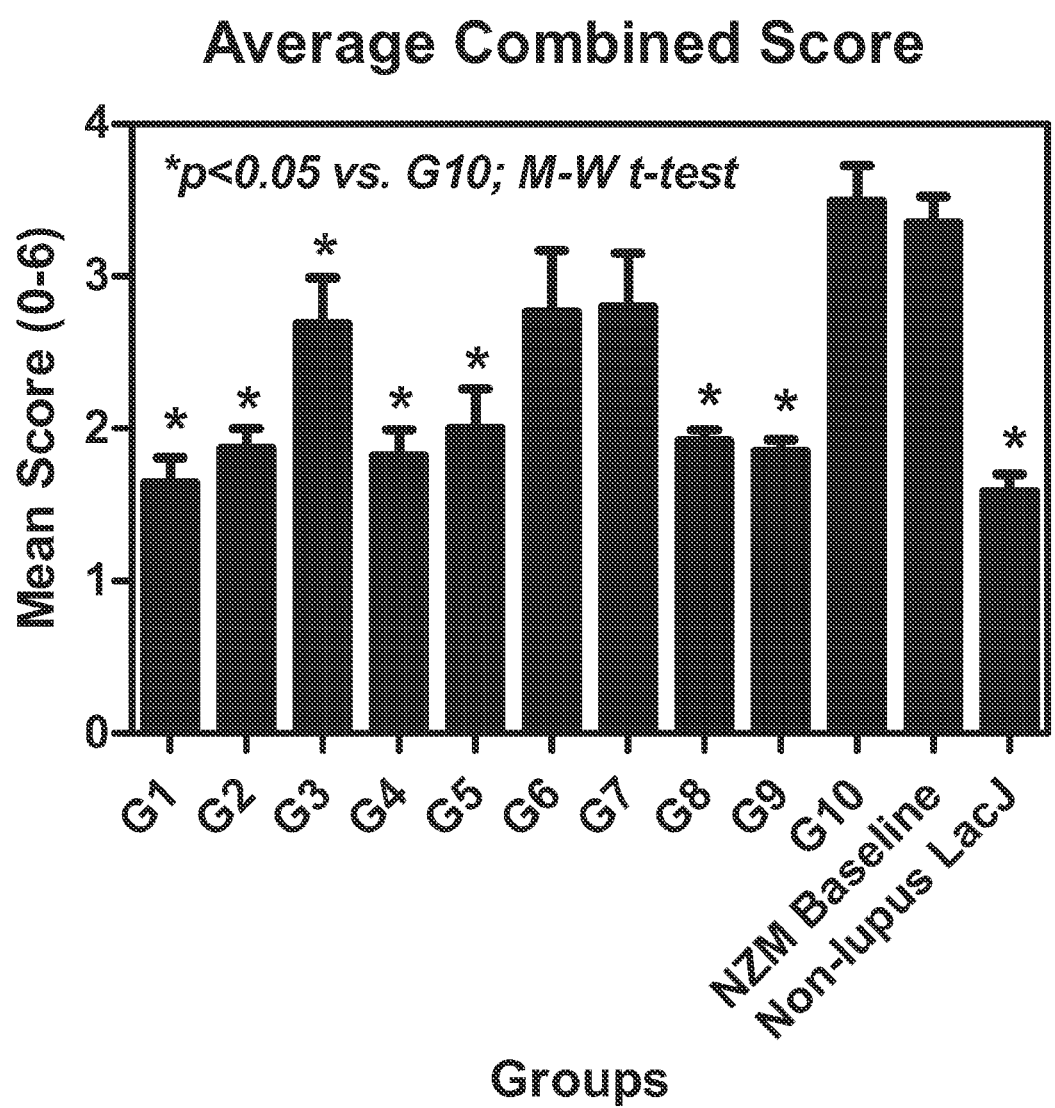
FIG. 52 depicts renal histopathology scores from NZM mice (H&E stained paraffin wax embedded kidney tissues sections from 25 week old mice). Graph shows Mean±SEM. * indicates p≤0.05 compared to vehicle control G10.

NZM mice treated with COMPOUND A exhibited decreased combined average renal histopathology blinded scores compared to vehicle (53%, 43.6%, 18.9%, 48.7%, and 40.5% for Groups 1-5, respectively) (see FIG. 52). These reductions in combined average renal histopathology blinded scores by COMPOUND A were greater than the reduction observed for the bortezomib ip treatment group (Group 7), which exhibited an insignificant reduction of only 19.4%. The bortezomib sc group (Group 8) exhibited a 43.6% decrease relative to the vehicle treatment group.

Pharmacodynamics

Figure 53:
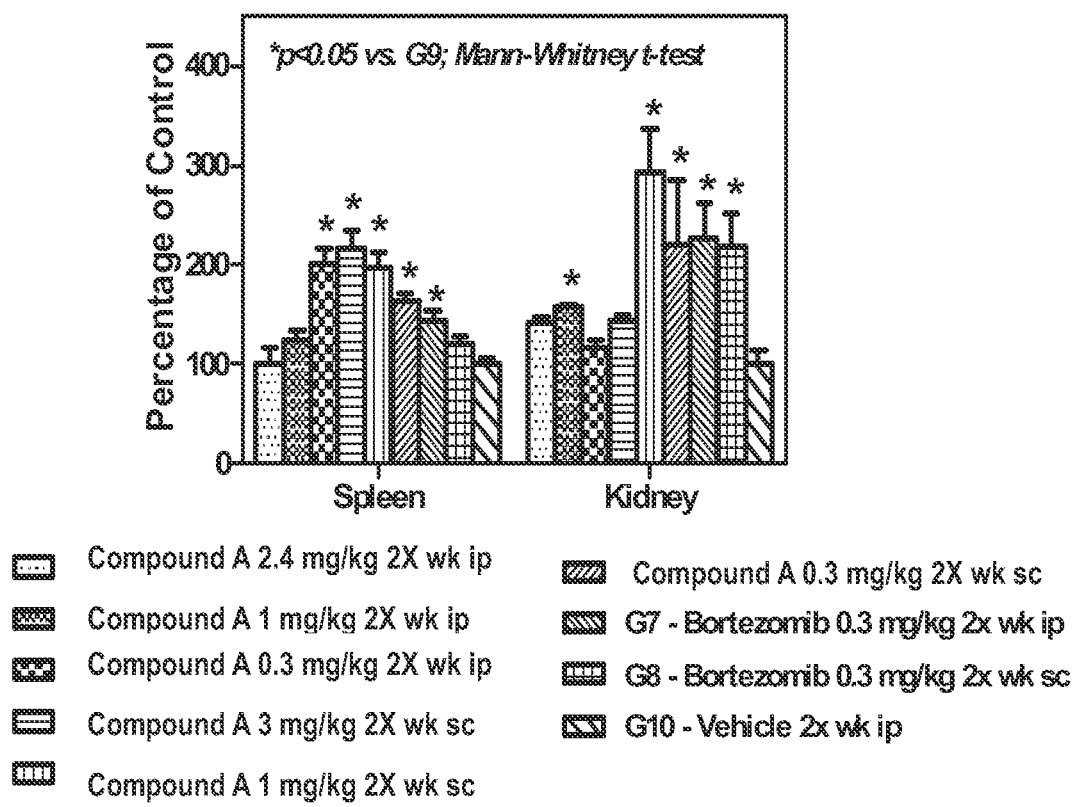
FIG. 53 depicts spleen and kidney IκBα accumulation 3 hours post dosing of NZM mice. Spleen and kidneys were lysed and analyzed using a commercial ELISA kit that measures the accumulation of cellular IκBα as a function of proteasome activity. Graph represents mean±SEM percent control for treatment groups.

The IκBα accumulation ELISA was used as the standard pharmacodynamic (PD) assay to measure proteasome inhibitory activity in the spleen and kidneys of treated mice (see FIG. 53).

Summary

Treatment of lupus-prone NZM mice with COMPOUND A ip or sc reduced disease symptoms of lupus nephritis and promoted survival. The results observed were generally superior to bortezomib, particularly as compared to the ip treatment group.

Preferred Embodiments

Preferred embodiments of the present invention include:

Embodiment 1: A method for treating lupus in a subject, comprising the step of administering to the subject COMPOUND A

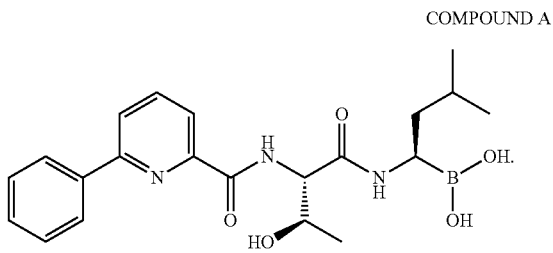 [SMILES: CC(C)C[C@H](NC(=O)[C@@H](NC(=O)c1cccc(-c2ccccc2)n1)[C@@H](C)O)B(O)O]

COMPOUND A

Embodiment 2

A method for treating lupus in a subject, comprising the step of administering to the subject an effective amount of COMPOUND A.

Embodiment 3: Use of COMPOUND A in the manufacture of a medicament for treating lupus in a subject.

Embodiment 4: COMPOUND A for use in the treatment of lupus in a subject.

Embodiment 5: The method, use, or compound of any of Embodiments 1 to 4, wherein the COMPOUND A is administered intravenously.

Embodiment 6: The method, use, or compound of any of Embodiments 1 to 4, wherein the COMPOUND A is administered subcutaneously.

Embodiment 7: The method, use, or compound of any of Embodiments 1 to 4, wherein the COMPOUND A is administered orally.

Embodiment 8: The method, use, or compound of any of Embodiments 1 to 7, wherein the COMPOUND A is administered at a dose of about 0.5 mg/m$^2$ to about 5 mg/m$^2$.

Embodiment 9: The method, use, or compound of any of Embodiments 1 to 7, wherein the COMPOUND A is administered at a dose of about 1 mg/m$^2$ to about 5 mg/mg$^2$.

Embodiment 10: The method, use, or compound of any of Embodiments 1 to 7, wherein the COMPOUND A is administered at a dose of about 0.5 mg/m$^2$ to about 3 mg/m$^2$.

Embodiment 11: The method, use, or compound of any of Embodiments 1 to 7, wherein the COMPOUND A is administered at a dose of about 1 mg/m$^2$ to about 4 mg/mg$^2$.

Embodiment 12: The method, use, or compound of any of Embodiments 1 to 7, wherein the COMPOUND A is administered at a dose of about 1 mg/m$^2$ to about 3 mg/mg$^2$.

Embodiment 13: The method, use, or compound of any of Embodiments 1 to 7, wherein the COMPOUND A is administered at a dose of about 1.5 mg/m$^2$ to about 3 mg/m$^2$.

Embodiment 14: The method, use, or compound of any of Embodiments 1 to 7, wherein the COMPOUND A is administered at a dose of about 2 mg/m$^2$.

Embodiment 15: The method, use, or compound of any of Embodiments 1 to 7, wherein the COMPOUND A is administered at a dose of about 2 mg/m$^2$ to about 2.5 mg/m$^2$.

Embodiment 16: The method, use, or compound of any of Embodiments 1 to 7, wherein the COMPOUND A is administered at a dose of about 1.5 mg/m$^2$.

Embodiment 17: The method, use, or compound of any of Embodiments 1 to 7, wherein the COMPOUND A is administered at a dose of about 2.5 mg/m$^2$.

Embodiment 18: The method, use, or compound of any of Embodiments 1 to 7, wherein the COMPOUND A is administered at a dose of about 0.1 mg/m$^2$ to about 10 mg/m$^2$.

Embodiment 19: The method, use, or compound of any of Embodiments 1 to 7, wherein the COMPOUND A is administered at a dose of about 1 mg/m$^2$ to about 7 mg/m$^2$.

Embodiment 20: The method, use, or compound of any of Embodiments 1 to 7, wherein the COMPOUND A is administered at a dose of about 2 mg/m$^2$ to about 6 mg/m$^2$.

Embodiment 21: The method, use, or compound of any of Embodiments 1 to 7, wherein the COMPOUND A is administered at a dose of about 3 mg/m$^2$ to about 5 mg/m$^2$.

Embodiment 22: The method, use, or compound of any of Embodiments 1 to 7, wherein the COMPOUND A is administered at a dose of about 3 mg/m$^2$.

Embodiment 23: The method, use, or compound of any of Embodiments 1 to 7, wherein the COMPOUND A is administered at a dose of about 4 mg/m$^2$.

Embodiment 24: The method, use, or compound of any of Embodiments 1 to 7, wherein the COMPOUND A is administered at a dose of about 5 mg/m$^2$.

Embodiment 25: The method, use, or compound of any of Embodiments 1 to 7, wherein the COMPOUND A is administered at a dose of about 6 mg/m$^2$.

Embodiment 26: The method, use, or compound of any of Embodiments 1 to 25, wherein the COMPOUND A is administered twice weekly.

Embodiment 27: The method, use, or compound of any of Embodiments 1 to 25, wherein the COMPOUND A is administered once weekly.

Embodiment 28: The method, use, or compound of any of Embodiments 1 to 25, wherein the COMPOUND A is administered once every two weeks.

Embodiment 29: The method, use, or compound of any of Embodiments 1 to 25, wherein the COMPOUND A is administered on days 1, 4, 8 and 11 of a 21 day cycle.

Embodiment 30: The method, use, or compound of any of Embodiments 1 to 25, wherein the COMPOUND A is administered on days 1, 4, 8, and 11 of a 28 day cycle.

Embodiment 31: The method, use, or compound of any of Embodiments 1 to 25, wherein the COMPOUND A is administered on days 1, 8 and 15 of a 28 day cycle.

Embodiment 32: The method, use, or compound of any of Embodiments 1 to 25, wherein the COMPOUND A is administered on days 1 and 8 of a 21 day cycle.

Embodiment 33: The method, use, or compound of any of Embodiments 1 to 25, wherein the COMPOUND A is administered on days 1 and 8 of a 28 day cycle.

Embodiment 34: The method, use, or compound of any of Embodiments 1 to 25, wherein the COMPOUND A is administered on days 1 and 15 of a 21 day cycle.

Embodiment 35: The method, use, or compound of any of Embodiments 1 to 25, wherein the COMPOUND A is administered on days 1 and 15 of a 28 day cycle.

Embodiment 36: The method, use, or compound of any of Embodiments 1 to 25, wherein the COMPOUND A is administered on days 1, 6, 11, and 17 of a 28 day cycle.

Embodiment 37: The method, use, or compound of any of Embodiments 1 to 25, wherein the COMPOUND A is administered 1, 6 and 11 of a 21 day cycle.

Embodiment 38: The method, use, or compound of any of Embodiments 29 to 37, wherein the cycle is repeated at least once.

Embodiment 39: The method, use, or compound of any of Embodiments 1 to 38, wherein the subject experiences a decrease in lymphomegaly during treatment.

Embodiment 40: The method, use, or compound of any of Embodiments 1 to 39, wherein the subject experiences a decrease in splenomegaly during treatment.

Embodiment 41: The method, use, or compound of any of Embodiments 1 to 40, wherein the subject experiences a decrease in one or more serum antinuclear antibodies during treatment.

Embodiment 42: The method, use, or compound of any of Embodiments 1 to 41, wherein the subject experiences a decrease in one or more serum cytokines during treatment.

Embodiment 43: The method, use, or compound of any of Embodiments 1 to 42, wherein the subject experiences a decrease in serum IFNα during treatment.

Embodiment 44: The method, use, or compound of any of Embodiments 1 to 43, wherein the subject experiences a decrease in proteinuria during treatment.

Embodiment 45: The method, use, or compound of any of Embodiments 1 to 44, wherein the subject experiences a decrease in serum IL-12 during treatment.

Embodiment 46: The method, use, or compound of any of Embodiments 1 to 45, wherein the subject experiences a decrease in serum IL-17A during treatment.

Embodiment 47: The method, use, or compound of any of Embodiments 1 to 46, wherein the subject experiences a decrease in serum IL-6 during treatment.

Embodiment 48: The method, use, or compound of any of Embodiments 1 to 47, wherein the subject experiences a decrease in serum CCL3/MIP-1α during treatment.

Embodiment 49: The method, use, or compound of any of Embodiments 1 to 48, wherein the subject experiences a decrease in serum CXCL10/IP-10 during treatment.

Embodiment 50: The method, use, or compound of any of Embodiments 1 to 49, wherein the subject experiences a decrease in serum CXCL9/MIG during treatment.

Embodiment 51: The method, use, or compound of any of Embodiments 1 to 50, wherein the subject experiences a decrease in serum IL-4 during treatment.

Embodiment 52: The method, use, or compound of any of Embodiments 1 to 51, wherein the subject experiences a decrease in serum IL-13 during treatment.

Embodiment 53: The method, use, or compound of any of Embodiments 1 to 52, wherein the subject experiences a decrease in serum TNFα during treatment.

Embodiment 54: The method, use, or compound of any of Embodiments 1 to 53, wherein the subject experiences a decrease in serum KC/IL-8 during treatment.

Embodiment 55: The method, use, or compound of any of Embodiments 1 to 54, wherein the subject experiences a decrease in serum CTx during treatment.

Embodiment 56: The method, use, or compound of any of Embodiments 1 to 55, wherein the subject experiences an increase in serum C3 during treatment.

Embodiment 57: The method, use, or compound of any of Embodiments 1 to 56, wherein the subject experiences a decrease in serum anti-chromatin IgG during treatment.

Embodiment 58: The method, use, or compound of any of Embodiments 1 to 57, wherein the subject experiences a decrease in serum anti-Smith Ag IgG during treatment.

Embodiment 59: The method, use, or compound of any of Embodiments 1 to 58, wherein the subject experiences a decrease in serum IL-1β during treatment.

Embodiment 60: The method, use, or compound of any of Embodiments 1 to 59, wherein the subject experiences a decrease in serum anti-dsDNA antinuclear antibodies during treatment.

Embodiment 61: The method, use, or compound of any of Embodiments 1 to 60, wherein the COMPOUND A is administered as a prodrug.

Embodiment 62: The method, use, or compound of Embodiment 61, wherein the prodrug is a boronic ester derivative of COMPOUND A.

Embodiment 63: The method, use, or compound of Embodiment 62, wherein the prodrug is a cyclic boronic ester derivative of COMPOUND A.

Embodiment 64: The method, use, or compound of Embodiment 63, wherein the prodrug is COMPOUND B

COMPOUND B

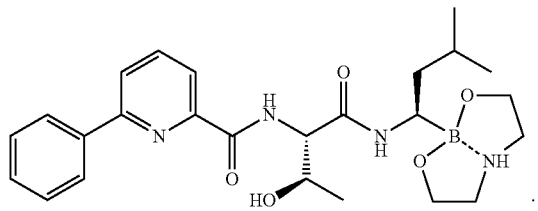

Embodiment 65: The method, use, or compound of any of Embodiments 1 to 64, wherein the subject is a human.

Embodiment 66: The method, use, or compound of any of Embodiments 1-56, wherein the subject experiences a decrease in serum anti-chromatin ANA during treatment.

Embodiment 67: The method, use, or compound of any of Embodiments 1-56 or 66, wherein the subject experiences a decrease in serum anti-Smith Ag ANA during treatment.

Embodiment 68: The method, use, or compound of any of Embodiments 1-56, 66, or 67, wherein the subject experiences a decrease in serum IL-1β during treatment.

Embodiment 69: The method, use, or compound of any of Embodiments 1-56 or 66-68, wherein the subject experiences a decrease in serum anti-dsDNA ANA during treatment.

Embodiment 70: The method, use, or compound of any of Embodiments 1-56 or 66-69, wherein the COMPOUND A is administered as a prodrug.

Embodiment 71: The method, use, or compound of Embodiment 70, wherein the prodrug is a boronic ester derivative of COMPOUND A.

Embodiment 72: The method, use, or compound of Embodiment 71, wherein the prodrug is a cyclic boronic ester derivative of COMPOUND A.

Embodiment 73: The method, use, or compound of Embodiment 72, wherein the prodrug is COMPOUND B

COMPOUND B

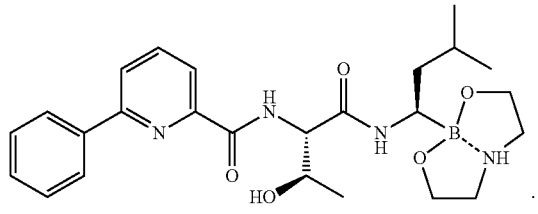

Embodiment 74: The method, use, or compound of any of Embodiments 1-56 or 66-73, wherein the subject is a human.

Additional Preferred Embodiments include:
1. A method for treating lupus in a subject, comprising the step of administering to the subject COMPOUND A

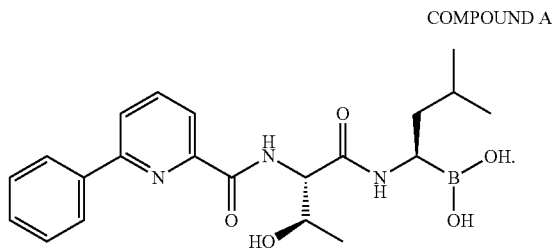 [SMILES: CC(C)C[C@H](NC(=O)[C@@H](NC(=O)c1cccc(-c2ccccc2)n1)[C@@H](C)O)B(O)O]

COMPOUND A

2. The method of preferred embodiment 1, wherein the subject is a human.
3. The method of preferred embodiment 2, wherein the COMPOUND A is administered as a prodrug.
4. The method of preferred embodiment 3, wherein the prodrug is a boronic ester of COMPOUND A.
5. The method of preferred embodiment 4, wherein the prodrug is COMPOUND B

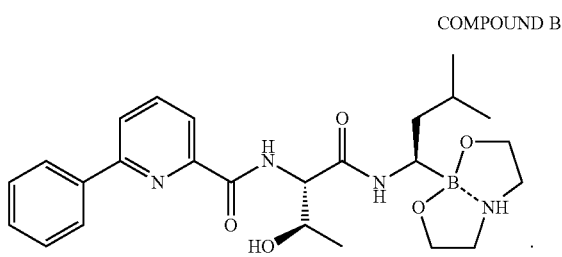

COMPOUND B

6. The method of preferred embodiment 2, wherein the COMPOUND A is administered once per week.
7. The method of preferred embodiment 2, wherein the COMPOUND A is administered at a dose of about 0.5 mg/m$^2$ to about 5 mg/m$^2$.
8. The method of preferred embodiment 2, wherein the COMPOUND A is administered at a dose of about 1 mg/m$^2$ to about 3 mg/m$^2$.
9. The method of preferred embodiment 2, wherein the COMPOUND A is administered at a dose of about 2 mg/m$^2$.
10. The method of preferred embodiment 5, wherein the COMPOUND A is administered at a dose of about 0.5 mg/m$^2$ to about 5 mg/m$^2$.
11. The method of preferred embodiment 5, wherein the COMPOUND A is administered at a dose of about 1 mg/m$^2$ to about 3 mg/m$^2$.
12. The method of preferred embodiment 5, wherein the COMPOUND A is administered at a dose of about 2 mg/m$^2$.
13. The method of any of preferred embodiments 1 to 12, wherein the subject experiences a decrease in one or more serum cytokines during treatment.
14. The method of any of preferred embodiments 1 to 12, wherein the subject experiences a decrease in IL-12 during treatment.
15. The method of any of preferred embodiments 1 to 12, wherein the subject experiences a decrease in one or more serum antinuclear antibodies during treatment.
16. The method of any of preferred embodiments 1 to 12, wherein the subject experiences a decrease in serum antichromatin IgG during treatment.
17. The method of any of preferred embodiments 1 to 12, wherein the subject experiences a decrease in serum anti-Smith Ag IgG during treatment.
18. The method of any of preferred embodiments 1 to 12, wherein the subject experiences a decrease in serum anti-dsDNA IgG during treatment.
19. The method of any of preferred embodiments 1 to 12, wherein the subject experiences a decrease in proteinuria during treatment.
20. The method of any of preferred embodiments 1 to 12, wherein the subject experiences an increase in serum C3 during treatment.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

All publications referenced herein are incorporated by reference in their entireties for all purposes.

REFERENCES

Aringer, M. and J. S. Smolen (2004). "Tumour necrosis factor and other proinflammatory cytokines in systemic lupus erythematosus: a rationale for therapeutic intervention." *Lupus* 13(5): 344-7.

Bertsias, G. and D. T. Boumpas (2008). "Update on the management of lupus nephritis: let the treatment fit the patient." *Nat Clin Pract Rheumatol* 4(9): 464-72.

Boumpas, D. T., R. Furie, et al. (2003). "A short course of BG9588 (anti-CD40 ligand antibody) improves serologic activity and decreases hematuria in patients with proliferative lupus glomerulonephritis." *Arthritis Rheum* 48(3): 719-27.

Chevrier, S., C. Genton, et al. (2009). "CD93 is required for maintenance of antibody secretion and persistence of plasma cells in the bone marrow niche." *Proc Natl Acad Sci USA* 106(10):3895-900.

Chauhan D, Anderson K C. (2003). "Mechanisms of cell death and survival in multiple myeloma (MM): Therapeutic implications." *Apoptosis* 8:337-43;

Chun, H. Y., J. W. Chung, et al. (2007). "Cytokine IL-6 and IL-10 as biomarkers in systemic lupus erythematosus." *J Clin Immunol* 27(5): 461-6.

Demo S D, Kirk C J, Aujay M A, et al. (2007). "Antitumor activity of PR-171, a novel irreversible inhibitor of the proteasome." *Cancer Res.* 67:6383-91.

Egner, W. (2000). "The use of laboratory tests in the diagnosis of SLE." *J Clin Pathol* 53(6): 424-32.

Espeli, M., S. Bokers, et al. (2011) "Local Renal Autoantibody Production in Lupus Nephritis." *J Am Soc Nephrol.* 22(2):296-305.

Fairhurst, A. M., A. E. Wandstrat, et al. (2006). "Systemic lupus erythematosus: multiple immunological phenotypes in a complex genetic disease." *Adv Immunol* 92: 1-69.

Fröhlich, K., Holle, J. U., et al. (2010). "Successful use of bortezomib in a patient with systemic lupus erythematosus and multiple myeloma." *Ann. Rheum. Dis. doi:*10.1136/ard.2010.133256 (published online ahead of print article).

Fu, Q., X. Chen, et al. (2008). "Association of elevated transcript levels of interferon-inducible chemokines with disease activity and organ damage in systemic lupus erythematosus patients." *Arthritis Res Ther* 10(5): R112.

Kiss, E., G. Lakos, et al. (2009). "Anti-nuscleosome antibody, a reliable indicator for lupus nephritis." *Autoimmunity* 42(5): 393-8.

Lee, S. W. and Kim, B. S. (2010). "Comparison of therapeutic efficacy between bortezomib and combination treatment of prednisolone and mycophenolate mofetil on nephritis in NZB/WF1 mice." *Clin. Exp. Rheumatol.* 28(3):393-396.

Morel, L. (2010). "Genetics of SLE: evidence from mouse models." *Nat Rev Rheumatol* 6(6): 348-57.

Morimoto, S., Y. Tokano, et al. (2001). "The increased interleukin-13 in patients with systemic lupus erythematosus: relations to other Th1-, Th2-related cytokines and clinical findings." *Autoimmunity* 34(1): 19-25.

Muller, S., J. Dieker, et al. (2008). "Pathogenic anti-nucleosome antibodies." *Lupus* 17(5): 431-6.

Neubert, K., S. Meister, et al. (2008). "The proteasome inhibitor bortezomib depletes plasma cells and protects mice with lupus-like disease from nephritis." *Nat Med* 14(7): 748-55.

Niewold, T. B., J. Hua, et al. (2007). "High serum IFN-alpha activity is a heritable risk factor for systemic lupus erythematosus." *Genes Immun* 8(6): 492-502.

Piva R, Ruggeri B, Williams M, et al. (2008). "CEP-18770: a novel orally-active proteasome inhibitor with a tumor-selective pharmacological profile competitive with bortezomib." *Blood* 111:2765-75.

Sanz, I. and F. E. Lee (2010). "B cells as therapeutic targets in SLE." *Nat Rev Rheumatol* 6(6): 326-37.

Smith, D. L., X. Dong, et al. (2007). "A female preponderance for chemically induced lupus in SJL/J mice." *Clin Immunol* 122(1): 101-7.

Smith-Bouvier, D. L., A. A. Divekar, et al. (2008). "A role for sex chromosome complement in the female bias in autoimmune disease." *J Exp Med* 205(5): 1099-108.

Tucci, M., L. Lombardi, et al. (2008). "Overexpression of interleukin-12 and T helper 1 predominance in lupus nephritis." *Clin Exp Immunol* 154(2): 247-54.

What is claimed:

1. A method for treating lupus in a subject, comprising administering to the subject COMPOUND A

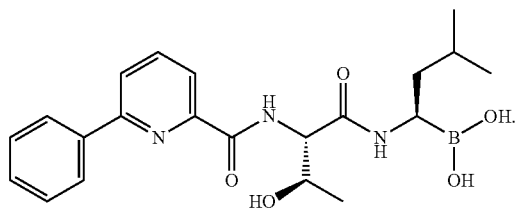

COMPOUND A

2. The method of claim 1, wherein the COMPOUND A is administered as a prodrug.

3. The method of claim 2, wherein the prodrug is a boronic ester of COMPOUND A.

4. The method of claim 3, wherein the prodrug is COMPOUND B

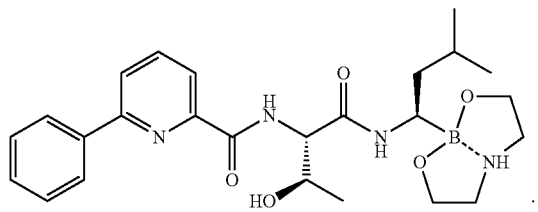

COMPOUND B

5. The method of claim 1, wherein the COMPOUND A is administered once per week.

6. The method of claim 1, wherein the COMPOUND A is administered twice per week.

7. The method of claim 1, wherein the COMPOUND A is administered subcutaneously.

8. The method of claim 1, wherein the COMPOUND A is administered at a dose of about 0.5 mg/m$^2$ to about 5 mg/m$^2$.

9. The method of claim 1, wherein the COMPOUND A is administered at a dose of about 1 mg/m$^2$ to about 3 mg/m$^2$.

10. The method of claim 1, wherein the COMPOUND A is administered at a dose of about 2 mg/m$^2$.

* * * * *